(12) United States Patent
Banner et al.

(10) Patent No.: US 8,815,881 B2
(45) Date of Patent: Aug. 26, 2014

(54) 1,4,5,6-TETRAHYDRO-PYRIMIDIN-2-YLAMINE COMPOUNDS

(75) Inventors: David Banner, Basel (CH); Emanuele Gabellieri, Siena (IT); Wolfgang Guba, Muellheim (DE); Hans Hilpert, Muenchenstein (CH); Benoit Hornsperger, Altkirch (FR); Roland Humm, Auggen (DE); Harald Mauser, Birsfelden (CH); Alexander V. Mayweg, Basel (CH); Robert Narquizian, Zaessingue (FR); Emmanuel Pinard, Linsdorf (FR); Mark Rogers-Evans, Bottmingen (CH); Thomas Woltering, Freiburg (DE); Wolfgang Wostl, Grenzach-Wyhlen (DE)

(73) Assignees: Hoffmann-La Roche Inc., Nutley, NJ (US); Siena Biotech S.p.A., Siena (IT)

(*) Notice: Subject to any disclaimer, the term of this patent is extended or adjusted under 35 U.S.C. 154(b) by 129 days.

(21) Appl. No.: 13/196,933

(22) Filed: Aug. 3, 2011

(65) Prior Publication Data
US 2012/0035195 A1 Feb. 9, 2012

(30) Foreign Application Priority Data
Aug. 9, 2010 (EP) ................................. 10172299

(51) Int. Cl.
*C07D 239/22* (2006.01)
*A61K 31/513* (2006.01)

(52) U.S. Cl.
CPC .............. *C07D 239/22* (2013.01); *A61K 31/513* (2013.01)
USPC ........................................... 514/272; 544/321

(58) Field of Classification Search
CPC ............................ C07D 239/22; A61K 31/513
USPC ........................................... 544/321; 514/272
See application file for complete search history.

(56) References Cited

U.S. PATENT DOCUMENTS

| 7,348,326 | B2 * | 3/2008 | DeSimone et al. | 514/248 |
| 7,348,338 | B2 * | 3/2008 | Arnold et al. | 514/300 |
| 7,348,341 | B2 * | 3/2008 | Sanganee et al. | 514/318 |
| 7,348,342 | B2 * | 3/2008 | Lohray et al. | 514/334 |
| 8,461,160 | B2 * | 6/2013 | Banner et al. | 514/252.02 |
| 2011/0237576 | A1 * | 9/2011 | Yonezawa et al. | 514/230.5 |

FOREIGN PATENT DOCUMENTS

| WO | 2006009653 | 1/2006 |
| WO | 2006041404 | 4/2006 |
| WO | 2006041405 | 4/2006 |
| WO | 2008/019124 | 2/2008 |
| WO | 2009/005677 | 1/2009 |
| WO | 2010/027567 | 3/2010 |
| WO | WO 2010/047372 | * 4/2010 |
| WO | WO 2010/128058 | * 11/2010 |

OTHER PUBLICATIONS

Kuhn et al., "Journal of Biological Chemistry" 282(16):11982-11995 (2007).
Akpinar et al., "Cell Metabolism" 2:385-397 (2005).
Tang et al., "Journal of Organic Chemistry" 64:12-13 (1999).
Vogt et al., "Synthetic Commun." 31(5):679-684 (2001).
Zimmet et al., "Nature" 414:782-787 (2001).
Prentki et al., "Journal of Clinical Investigation" 116(7):1802-1812 (2006).
Wild et al., "Diabetes Care" 27(5):1047-1053 (2004).
Finzi et al., "Ultrastructure Pathology" 32(6):246-251 (2008).
Hussain et al., "Molecular and Cellular Neuroscience" 16:609-619 (2000).
Baggio et al., "Annual Review of Medicine" 57:265-281 (2006).
Meinwald et al., "Tetrahedron" 18:815-820 (1962).
Bunce et al., "Journal of Organic Chemistry" 60(9):2748-2752 (1995).
Fukui et al., "Cell Metabolism" 2:373-384 (2005).
Kousik et al., "Journal of American Chemistry Society" 127:16042-16043 (2005).
Gassen et al., "Journal of Fluorine Chemistry" 49(1):127-139 (1990).
The English translation of the Japanese Office Action, issued on Jun. 3, 2014, in the corresponding Japanese application No. 2013-523573.

* cited by examiner

Primary Examiner — Deepak Rao

(57) ABSTRACT

This invention relates to compounds of the formula

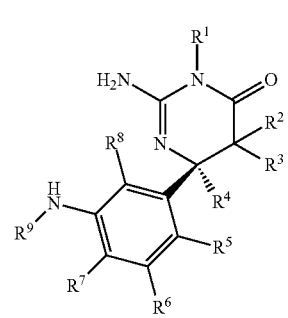

wherein $R^1$ to $R^9$ are as described below, or to pharmaceutically acceptable salts thereof. These compounds are BACE2 inhibitors and can be used as medicaments for the therapeutic and/or prophylactic treatment of diseases such as diabetes, particularly type 2 diabetes, and other metabolic disorders.

14 Claims, No Drawings

1,4,5,6-TETRAHYDRO-PYRIMIDIN-2-YLAMINE COMPOUNDS

PRIORITY TO RELATED APPLICATIONS

This application claims the benefit of European Patent Application No. 10172299.9, filed Aug. 9, 2010, which is hereby incorporated by reference in its entirety.

FIELD OF THE INVENTION

The present invention is concerned with 1,4,5,6-tetrahydro-pyrimidin-2-ylamine compounds having BACE2 inhibitory properties, their manufacture, pharmaceutical compositions containing them and their use as therapeutically active substances.

The compounds of the invention have BACE2 inhibitory activity and can therefore be used in the therapeutic and/or prophylactic treatment of diseases and disorders such as type 2 diabetes and other metabolic disorders.

BACKGROUND OF THE INVENTION

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors with enhanced therapeutic and pharmacological properties compared to the compounds already known in the art. Such compounds are useful as therapeutically active substances, particularly in the treatment and/or prevention of diseases which are associated with the inhibition of BACE2 such as type 2 diabetes.

DETAILED DESCRIPTION OF THE INVENTION

Objects of the present invention are thus novel compounds of formula I having BACE2 inhibitory properties, their manufacture, medicaments comprising the compounds of the present invention, the production of such medicaments as well as the use of the compounds of formula I in the treatment or prevention of diseases such as type 2 diabetes.

Unless otherwise indicated, the following definitions are set forth to illustrate and define the meaning and scope of the various terms used to describe the invention.

The term "halogen" refers to fluoro, chloro, bromo and iodo, with fluoro, chloro and bromo being of particular interest. More particularly, halogen refers to fluoro and chloro.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, in particular methyl and ethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy.

The term "cycloalkyl" or "$C_{3-7}$-cycloalkyl" denotes a saturated carbocyclic group containing from 3 to 7 carbon atoms, such as monocyclic groups such as cyclopropyl, cyclobutyl, cyclopentyl, cyclohexyl or cycloheptyl, but also bicyclic groups such bicyclo[2.2.1]heptyl or bicyclo[3.1.0]hexyl. In particular, cycloalkyl means cyclopropyl, cyclobutyl and cyclopentyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, more particularly fluoro. Among the lower halogenalkyl groups are trifluoromethyl, difluoromethyl, trifluoroethyl, 2,2-difluoroethyl, fluoromethyl and chloromethyl, with trifluoromethyl or difluoromethyl being of particular interest.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, more particularly fluoro. Among the halogenated lower alkoxy groups are trifluoromethoxy, 2,2,2-trifluoroethoxy, difluoromethoxy, fluormethoxy and chloromethoxy, with trifluoromethoxy and 2,2,2-trifluoroethoxy being of particular interest.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the lower hydroxyalkyl groups are hydroxymethyl or hydroxyethyl.

The term "lower hydroxyhalogenalkyl" or "hydroxy-halogen-$C_{1-7}$-alkyl" refers to lower alkyl groups as defined above wherein at least one of the hydrogen atoms of the lower alkyl group is replaced by a hydroxy group and at least one of the hydrogen atoms of the lower alkyl group is replaced by a halogen group. Among the particular interesting lower hydroxyhalogenalkyl groups is 3,3,3-trifluoro-2-hydroxy-2-propyl.

The term "lower alkoxy-lower halogenalkyl" or "$C_{1-7}$-alkoxy-halogen-$C_{1-7}$-alkyl" refers to lower alkyl groups as defined above wherein at least one of the hydrogen atoms of the lower alkyl group is replaced by a lower alkoxy group, in particular methoxy, and at least one of the hydrogen atoms of the lower alkyl group is replaced by a halogen group.

The term "oxo" means the group "=O" bound to a ring atom.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups or particular interest are carboxylmethyl (—$CH_2$—COOH) and carboxylethyl (—$CH_2$—$CH_2$—COOH).

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A lower alkoxycarbonylalkyl group of particular interest is —$CH_2$—$COOCH_3$.

The term "lower alkylcarbonyl" or "$C_{1-7}$-alkylcarbonyl" refers to the group —CO—R, wherein R is a lower alkyl group as defined herein before, in particular methyl.

"Lower alkylcarbonyloxy" or "$C_{1-7}$-alkylcarbonyloxy" refers to the group —O—CO—R, wherein R is a lower alkyl group as defined herein before, in particular methyl.

The term "aryl" refers to an aromatic monocyclic or multicyclic ring system having 6 to 14 carbon atoms, in particular 6 to 10 carbon atoms. Exemplary aryl groups are phenyl and naphthyl. In particular, aryl means phenyl.

The term "heteroaryl" refers to an aromatic or partly unsaturated 5- or 6-membered ring which comprises at least one heteroatom selected from nitrogen, oxygen and/or sulphur, and can in addition comprise one or three atoms selected from nitrogen, oxygen and/or sulphur, such as pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, pyrrolo[2,3-b]pyridinyl, thieno[3,2-b]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl. In particular, heteroaryl groups are thienyl, oxazolyl, isoxazolyl, thiazolyl, pyrazolyl, imidazolyl, pyridyl, pyrimidinyl, pyrazinyl, 6-oxo-1,6-dihydropyridazinyl, 5-oxo-4,5-dihydropyrazinyl, imidazo[1,2-a]pyridyl, benzo[b]thienyl, pyrrolo[2,3-b]pyridinyl, thieno[3,2-b]pyridyl, thieno[2,3-c]pyridyl, quinolinyl and isoquinolinyl, more particularly oxazolyl, pyrazolyl, pyridyl and pyrimidinyl and most particularly pyridyl.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Preferably, the pharmaceutically acceptable salts of the compounds of formula I are the acid addition salts with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the acid addition salts such as the hydrochloride salts, the formate salts or trifluoroacetate salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The invention relates to compounds of the formula

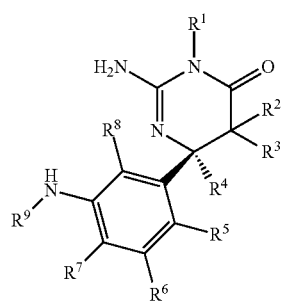

I wherein
$R^1$ is selected from the group consisting of hydrogen, $C_{1-7}$-alkyl, $C_{3-7}$-cycloalkyl, $C_{3-7}$-cycloalkyl-$C_{1-7}$-alkyl and benzyl;
$R^2$ is selected from the group consisting of hydrogen, $C_{1-7}$-alkyl and $C_{3-7}$-cycloalkyl;
$R^3$ is selected from the group consisting of hydrogen, $C_{1-7}$-alkyl and $C_{3-7}$-cycloalkyl; or $R^2$ and $R^3$ together with the C atom they are attached to form a $C_{3-7}$-cycloalkyl ring;
$R^4$ is $C_{1-7}$-alkyl or $C_{3-7}$-cycloalkyl;
$R^5$ is selected from the group consisting of hydrogen, $C_{1-7}$-alkyl, halogen, cyano and $C_{1-7}$-alkoxy;
or $R^4$ and $R^5$ together are —$(CH_2)_m$— with m being 2 or 3 and thus form a ring;
$R^6$, $R^7$ and $R^8$ independently from each other are selected from hydrogen and halogen; and
$R^9$ is —(CO)—$R^{10}$ or —$R^{11}$, wherein
$R^{10}$ is selected from the group consisting of
$C_{1-7}$-alkyl,
—$(CHR^{12})_m$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, benzyl and phenyl, said phenyl being unsubstituted or substituted by halogen, $R^{12}$ is hydrogen or $C_{1-7}$-alkyl, and m is 0, 1 or 2,
halogen-$C_{1-7}$-alkyl,
hydroxy-halogen-$C_{1-7}$-alkyl,
$C_{1-7}$-alkoxy-halogen-$C_{1-7}$-alkyl, —(CHR$^{13}$)$_n$-heterocyclyl, wherein heterocyclyl is unsubstituted or substituted by one, two or three groups selected from the group consisting of C$_{1-7}$-alkyl, halogen, halogen-C$_{1-7}$-alkyl, hydroxy, cyano, benzyl and phenyl, said phenyl being unsubstituted or substituted by halogen, R$^{13}$ is hydrogen or C$_{1-7}$-alkyl, and n is 0, 1 or 2, and —CH(OH)-phenyl, wherein phenyl is unsubstituted or substituted by halogen; and R$^{11}$ is selected from the group consisting of C$_{1-7}$-alkyl, —(CHR$^{14}$)$_p$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyloxy, benzyl and phenyl, said phenyl being unsubstituted or substituted by halogen, R$^{14}$ is hydrogen or C$_{1-7}$-alkyl, and p is 0, 1 or 2, halogen-C$_{1-7}$-alkyl, indanyl, being unsubstituted or substituted by one, two or three groups selected from the group consisting of C$_{1-7}$-alkyl, C$_{1-7}$-alkoxy, carboxyl, carboxyl-C$_{1-7}$-alkyl and halogen, tetrahydronaphtalenyl, being unsubstituted or substituted by one, two or three groups selected from C$_{1-7}$-alkyl and halogen, 6,7-dihydro-5H-cyclopenta[b]pyridinyl, being unsubstituted or substituted by one, two or three groups selected from C$_{1-7}$-alkyl and halogen, hydroxy-halogen-C$_{1-7}$-alkyl, C$_{1-7}$-alkoxy-halogen-C$_{1-7}$-alkyl, —(CHR$^{15}$)$_q$-heterocyclyl, wherein heterocyclyl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyl, C$_{1-7}$-alkylcarbonyloxy, oxo, C$_{3-7}$-cycloalkyl, imidazolyl, benzyl, phenylsulfanyl and phenyl, said phenyl being unsubstituted or substituted by halogen, R$^{15}$ is hydrogen or C$_{1-7}$-alkyl, and q is 0, 1 or 2;

—(CHR$^{16}$)$_s$-aryl, wherein aryl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, —SO$_2$—C$_{1-7}$-alkyl, phenylsulfanyl and phenyl, said phenyl being unsubstituted or substituted by halogen, R$^{16}$ is hydrogen or C$_{1-7}$-alkyl, and s is 0, 1 or 2; and —(CHR$^{17}$)$_t$-heteroaryl, wherein heteroaryl is unsubstituted or substituted by one, two or three groups selected from the group consisting of C$_{1-7}$-alkyl, halogen, halogen-C$_{1-7}$-alkyl, hydroxy, C$_{1-7}$-alkoxy, halogen-C$_{1-7}$-alkoxy, cyano, hydroxy-C$_{1-7}$-alkyl, carboxyl, C$_{1-7}$-alkoxycarbonyl, C$_{1-7}$-alkyl-carbonyl, oxo, C$_{3-7}$-cycloalkyl, imidazolyl, benzyl, phenylsulfanyl and phenyl, said phenyl being unsubstituted or substituted by halogen, R$^{17}$ is hydrogen or C$_{1-7}$-alkyl and t is 0, 1 or 2;

or pharmaceutically acceptable salts thereof.

In a certain embodiment the invention relates to compounds of formula I as defined herein, wherein R$^1$ is selected from the group consisting of hydrogen, C$_{1-7}$-alkyl, C$_{3-7}$-cycloalkyl, C$_{3-7}$-cycloalkyl-C$_{1-7}$-alkyl and benzyl;

R$^2$ is selected from the group consisting of hydrogen, C$_{1-7}$-alkyl and C$_{3-7}$-cycloalkyl;

R$^3$ is selected from the group consisting of hydrogen, C$_{1-7}$-alkyl and C$_{3-7}$-cycloalkyl;

or R$^2$ and R$^3$ together with the C atom they are attached to form a C$_{3-7}$-cycloalkyl ring;

R$^4$ is C$_{1-7}$-alkyl or C$_{3-7}$-cycloalkyl;

R$^5$ is selected from the group consisting of hydrogen, C$_{1-7}$-alkyl, halogen, cyano and C$_{1-7}$-alkoxy;

or R$^4$ and R$^5$ together are —(CH$_2$)$_m$— with m being 2 or 3 and thus form a ring;

R$^6$, R$^7$ and R$^8$ independently from each other are selected from hydrogen and halogen; and R$^9$ is —(CO)—R$^{10}$ or —R$^{11}$, wherein R$^{10}$ is selected from the group consisting of —(CHR$^{12}$)$_m$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, benzyl and phenyl, said phenyl being unsubstituted or substituted by halogen, R$^{12}$ is hydrogen or C$_{1-7}$-alkyl, and m is 0, 1 or 2, halogen-C$_{1-7}$-alkyl, hydroxy-halogen-C$_{1-7}$-alkyl, C$_{1-7}$-alkoxy-halogen-C$_{1-7}$-alkyl, —(CHR$^{13}$)$_n$-heterocyclyl, wherein heterocyclyl is unsubstituted or substituted by one, two or three groups selected from the group consisting of C$_{1-7}$-alkyl, halogen, halogen-C$_{1-7}$-alkyl, hydroxy, cyano, benzyl and phenyl, said phenyl being unsubstituted or substituted by halogen, R$^{13}$ is hydrogen or C$_{1-7}$-alkyl, R$^{13}$ is hydrogen or C$_{1-7}$-alkyl, and n is 0, 1 or 2, and —CH(OH)-phenyl, wherein phenyl is unsubstituted or substituted by halogen; and R$^{11}$ is selected from the group consisting of C$_{1-7}$-alkyl, —(CHR$^{14}$)$_p$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyloxy, benzyl and phenyl, said phenyl being unsubstituted or substituted by halogen, R$^{14}$ is hydrogen or C$_{1-7}$-alkyl, and p is 0, 1 or 2, halogen-C$_{1-7}$-alkyl, indanyl, being unsubstituted or substituted by one, two or three groups selected from the group consisting of C$_{1-7}$-alkyl, C$_{1-7}$-alkoxy, carboxyl, carboxyl-C$_{1-7}$-alkyl and halogen, tetrahydronaphtalenyl, being unsubstituted or substituted by one, two or three groups selected from C$_{1-7}$-alkyl or halogen, 6,7-dihydro-5H-cyclopenta[b]pyridinyl, being unsubstituted or substituted by one, two or three groups selected from C$_{1-7}$-alkyl and halogen, hydroxy-halogen-C$_{1-7}$-alkyl, C$_{1-7}$-alkoxy-halogen-C$_{1-7}$-alkyl, —(CHR$^{15}$)$_q$-heterocyclyl, wherein heterocyclyl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyl, C$_{1-7}$-alkylcarbonyloxy, oxo, C$_{3-7}$-cycloalkyl, imidazolyl, benzyl, phenylsulfanyl and phenyl, said phenyl being unsubstituted or substituted by halogen, R$^{15}$ is hydrogen or C$_{1-7}$-alkyl, and q is 0, 1 or 2;

—(CHR$^{16}$)$_s$-aryl, wherein aryl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —(CHR$^{17}$)$_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2;

or pharmaceutically acceptable salts thereof.

In a certain embodiment the invention relates to compounds of formula I as defined herein, wherein $R^1$ is $C_{1-7}$-alkyl or $C_{3-7}$-cycloalkyl-$C_{1-7}$-alkyl.

In a certain embodiment the invention relates to compounds of formula I as defined herein, wherein $R^1$ is $C_{1-7}$-alkyl.

In a certain embodiment the invention relates to compounds of formula I as defined herein, wherein $R^1$ is methyl.

In a certain embodiment the invention relates to compounds of formula I as defined herein, wherein $R^2$ and $R^3$ are independently from each other selected from hydrogen or $C_{1-7}$-alkyl.

In a certain embodiment the invention relates to compounds of formula I as defined herein, wherein $R^2$ and $R^3$ are $C_{1-7}$-alkyl.

In a certain embodiment the invention relates to compounds of formula I as defined herein, wherein $R^2$ and $R^3$ are methyl.

In a certain embodiment the invention relates to compounds of formula I as defined herein, wherein $R^4$ is $C_{1-7}$-alkyl.

In a certain embodiment the invention relates to compounds of formula I as defined herein, wherein $R^4$ is methyl.

In a certain embodiment the invention relates to compounds of formula I as defined herein, wherein $R^5$ is hydrogen or halogen.

In a certain embodiment the invention relates to compounds of formula I as defined herein, wherein $R^5$ is halogen.

In a certain embodiment the invention relates to compounds of formula I as defined herein, wherein $R^5$ is fluoro.

In a certain embodiment the invention relates to compounds of formula I as defined herein, wherein $R^6$, $R^7$ and $R^8$ are hydrogen.

In a certain embodiment the invention relates to compounds of formula I as defined herein, wherein $R^9$ is —(CO)—$R^{10}$ and $R^{10}$ is selected from the group consisting of —(CHR$^{12}$)$_m$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, benzyl and phenyl, said phenyl being unsubstituted or substituted by halogen, $R^{12}$ is hydrogen or $C_{1-7}$-alkyl, and m is 0, 1 or 2, halogen-$C_{1-7}$-alkyl, hydroxy-halogen-$C_{1-7}$-alkyl, $C_{1-7}$-alkoxy-halogen-$C_{1-7}$-alkyl, —(CHR$^{13}$)$_n$-heterocyclyl, wherein heterocyclyl is unsubstituted or substituted by one, two or three groups selected from the group consisting of $C_{1-7}$-alkyl, halogen, halogen-$C_{1-7}$-alkyl, cyano, benzyl and phenyl, said phenyl being unsubstituted or substituted by halogen, $R^{13}$ is hydrogen or $C_{1-7}$-alkyl, $R^{13}$ is hydrogen or $C_{1-7}$-alkyl, and n is 0, 1 or 2, and —CH(OH)-phenyl, wherein phenyl is unsubstituted or substituted by halogen.

In a certain embodiment the invention relates to compounds of formula I as defined herein, wherein $R^{10}$ is —(CHR$^{12}$)$_m$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, benzyl and phenyl, said phenyl being unsubstituted or substituted by halogen, $R^{12}$ is hydrogen or $C_{1-7}$-alkyl, and m is 0, 1 or 2.

In a certain embodiment the invention relates to compounds of formula I as defined herein, wherein $R^{10}$ is selected from the group consisting of halogen-$C_{1-7}$-alkyl, hydroxy-halogen-$C_{1-7}$-alkyl, and $C_{1-7}$-alkoxy-halogen-$C_{1-7}$-alkyl.

In a certain embodiment the invention relates to compounds of formula I as defined herein, wherein $R^{10}$ is selected from the group consisting of —(CHR$^{12}$)$_m$—$C_{3-7}$-cycloalkyl, wherein cycloalkyl is unsubstituted or substituted by one or two halogen-$C_{1-7}$-alkyl groups, and m is 0, and hydroxy-halogen-$C_{1-7}$-alkyl.

In a certain embodiment the invention relates to compounds of formula I as defined herein, wherein $R^{10}$ is 1-trifluoromethyl-cyclopropanyl, 2,2,2-trifluoro-1-hydroxy-ethyl or 1,1,1-trifluoro-2-hydroxy-2-methyl-ethyl.

In a certain embodiment the invention relates to compounds of formula I as defined herein, wherein $R^9$ is $R^{11}$ and $R^{11}$ is selected from the group consisting of $C_{1-7}$-alkyl, —(CHR$^{14}$)$_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, halogen-$C_{1-7}$-alkyl, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, hydroxy-halogen-$C_{1-7}$-alkyl, $C_{1-7}$-alkoxy-halogen-$C_{1-7}$-alkyl, —(CHR$^{15}$)$_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—(CHR$^{16}$)$_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —(CHR$^{17}$)$_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2.

In a certain embodiment the invention relates to compounds of formula I as defined herein, wherein $R^{11}$ is selected from the group consisting of —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—$(CHR^{16})_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{17}$ is hydrogen or $C_{1-7}$-alkyl, and t is 0, 1 or 2.

In a certain embodiment the invention relates to compounds of formula I as defined herein, wherein $R^{11}$ is —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2.

In a certain embodiment the invention relates to compounds of formula I as defined herein, wherein $R^{11}$ is selected from the group consisting of indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl and halogen, 6,7-dihydro-5H-cyclopenta[b]pyridinyl, being unsubstituted or substituted by one, two or three groups selected from $C_{1-7}$-alkyl and halogen, and —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2.

In a certain embodiment the invention relates to compounds of formula I as defined herein, wherein $R^{11}$ is —$(CHR^{16})_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2.

In a certain embodiment the invention relates to compounds of formula I as defined herein, wherein $R^{11}$ is —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{17}$ is hydrogen or $C_{1-7}$-alkyl and t is 0, 1 or 2.

In a certain embodiment the invention relates to compounds of formula I as defined herein, wherein $R^{11}$ is selected from the group consisting of $C_{1-7}$-alkyl, halogen-$C_{1-7}$-alkyl, hydroxy-halogen-$C_{1-7}$-alkyl and $C_{1-7}$-alkoxy-halogen-$C_{1-7}$-alkyl.

In a certain embodiment the invention relates to compounds of formula I as defined herein, wherein $R^{11}$ is selected from the group consisting of —$(CHR^{14})_p$—$C_{3-7}$-cycloalkyl, wherein cycloalkyl is unsubstituted or substituted by one or two groups selected from the group consisting of hydroxy, halogen and cyano, $R^{14}$ is hydrogen, and p is 0 or 1, —$(CHR^{15})_q$-heterocyclyl, wherein heterocyclyl is unsubstituted, $R^{15}$ is hydrogen, and q is 0 or 1;

—$(CHR^{16})_s$-aryl, wherein aryl is unsubstituted or substituted by one or two groups selected from the group consisting of halogen-$C_{1-7}$-alkyl, and $C_{1-7}$-alkoxy, and s is 0; and —$(CHR^{17})_t$-heteroaryl, wherein heteroaryl is unsubstituted or substituted by one or two groups selected from the group consisting of $C_{1-7}$-alkyl, halogen, halogen-$C_{1-7}$-alkyl, $C_{1-7}$-alkoxy, and oxo, $R^{17}$ is hydrogen or $C_{1-7}$-alkyl, and t is 0 or 1.

In a certain embodiment the invention relates to compounds of formula I as defined herein, wherein $R^{11}$ is selected from the group consisting of: tetrahydro-furyl, tetrahydro-pyranyl, 2,2-difluoro-cyclopropyl-methyl, 3-chloro-6,7-dihydro-5H-cyclopenta[b]pyridinyl, tetrahydro-furyl-methyl, 4-chloro-1-methyl-1H-pyrazolyl-methyl, 1-methyl-1H-pyrazolyl, 5-hydroxybicyclo[2.2.1]heptanyl, 5-methyl-isoxazol-3-yl-methyl, pyridinyl, 1-(2H-pyrazolyl)-ethyl, 2-methoxy-5-(trifluoromethyl)phenyl, 1-(5-methyl-2H-pyrazolyl)-ethyl, 4-chloro-2H-pyrazolyl, cyano-cyclopentyl and 1,1-dioxo-2,3-dihydro-1H-1-benzo[b]thiophenyl.

In a certain embodiment the invention relates to compounds of formula I as defined herein, selected from the group consisting of
- salt of 1-Cyano-cyclopropanecarboxylic acid [3-((R)-2-amino-1,4,5,5-tetramethyl-6-oxo-1,4,5,6-tetrahydro-pyrimidin-4-yl)-phenyl]-amide with trifluoro-acetic acid,
- (1S,2S)-2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile,
- (1S,3R,5R,6S)-2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylic acid,
- (1S,3R,5R,6S)-ethyl 2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylate,
- (6S)-2-Amino-6-(2-fluoro-5-(1-(4-fluorophenyl)pyrrolidin-3-ylamino)phenyl)-3,5,5,6-tetramethyl-5,6-dihydropyrimidin-4(3H)-one,
- (6S)-2-Amino-6-(2-fluoro-5-(2-methyltetrahydrofuran-3-ylamino)phenyl)-3,5,5,6-tetramethyl-5,6-dihydropyrimidin-4(3H)-one,
- (6S)-2-Amino-6-(2-fluoro-5-(3-phenylcyclopentylamino)phenyl)-3,5,5,6-tetramethyl-5,6-dihydropyrimidin-4(3H)-one,
- (6S)-2-Amino-6-(2-fluoro-5-(5-fluoro-2,3-dihydro-1H-inden-1-ylamino)phenyl)-3,5,5,6-tetramethyl-5,6-dihydropyrimidin-4(3H)-one,
- (6S)-2-Amino-6-(2-fluoro-5-(5-fluoro-2-methyl-2,3-dihydro-1H-inden-1-ylamino)phenyl)-3,5,5,6-tetramethyl-5,6-dihydropyrimidin-4(3H)-one,
- (6S)-2-Amino-6-(2-fluoro-5-(5-hydroxybicyclo[2.2.1]heptan-2-ylamino)phenyl)-3,5,5,6-tetramethyl-5,6-dihydropyrimidin-4(3H)-one,
- (6S)-2-Amino-6-(2-fluoro-5-(7-fluoro-2,3-dihydro-1H-inden-1-ylamino)phenyl)-3,5,5,6-tetramethyl-5,6-dihydropyrimidin-4(3H)-one,
- (6S)-2-Amino-6-(2-fluoro-5-(7-methyl-2,3-dihydro-1H-inden-1-ylamino)phenyl)-3,5,5,6-tetramethyl-5,6-dihydropyrimidin-4(3H)-one,
- (6S)-2-amino-6-(5-((2R,6S)-2,6-dimethyltetrahydro-2H-pyran-4-ylamino)-2-fluorophenyl)-3,5,5,6-tetramethyl-5,6-dihydropyrimidin-4(3H)-one,
- (6S)-2-Amino-6-(5-(1-benzylpyrrolidin-3-ylamino)-2-fluorophenyl)-3,5,5,6-tetramethyl-5,6-dihydropyrimidin-4(3H)-one,
- (6S)-2-amino-6-(5-(2,3-dihydrobenzofuran-3-ylamino)-2-fluorophenyl)-3,5,5,6-tetramethyl-5,6-dihydropyrimidin-4(3H)-one,
- (6S)-2-Amino-6-(5-(2-chlorocyclopentylamino)-2-fluorophenyl)-3,5,5,6-tetramethyl-5,6-dihydropyrimidin-4(3H)-one,
- (6S)-2-Amino-6-(5-(3,3-dimethyl-2,3-dihydro-1H-inden-1-ylamino)-2-fluorophenyl)-3,5,5,6-tetramethyl-5,6-dihydropyrimidin-4(3H)-one,
- (6S)-2-Amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one,
- (6S)-2-Amino-6-(5-(5-chloro-3,3-dimethyl-2,3-dihydro-1H-inden-1-ylamino)-2-fluorophenyl)-3,5,5,6-tetramethyl-5,6-dihydropyrimidin-4(3H)-one,
- salt of (R)-2,2-Difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid,
- salt of (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoroacetic acid,
- (S)-2-(3-(2-Amino-1,4,5,5-tetramethyl-6-oxo-1,4,5,6-tetrahydropyrimidin-4-yl)-4-fluorophenylamino)benzonitrile,
- salt of (S)-2,2-difluoro-cyclopropanecarboxylic acid [3-((S)-2-amino-1,4,5,5-tetramethyl-6-oxo-1,4,5,6-tetrahydropyrimidin-4-yl)-4-fluoro-phenyl]-amide with trifluoroacetic acid,
- (S)-2-Amino-6-(2-fluoro-5-((1S,2S)-2-hydroxycyclopentylamino)phenyl)-3,5,5,6-tetramethyl-5,6-dihydropyrimidin-4(3H)-one,
- (S)-2-Amino-6-(2-fluoro-5-(2-(trifluoromethoxy)phenylamino)phenyl)-3,5,5,6-tetramethyl-5,6-dihydropyrimidin-4(3H)-one,
- (S)-2-Amino-6-(2-fluoro-5-(2,2,2-trifluoroethylamino)phenyl)-3,5,5,6-tetramethyl-5,6-dihydropyrimidin-4(3H)-one,
- (S)-2-Amino-6-(2-fluoro-5-(2,4,5-trimethylphenyl-amino)phenyl)-3,5,5,6-tetramethyl-5,6-dihydro-pyrimidin-4(3H)-one,
- (S)-2-Amino-6-(2-fluoro-5-(2-fluorophenylamino)phenyl)-3,5,5,6-tetramethyl-5,6-dihydropyrimidin-4(3H)-one,
- (S)-2-Amino-6-(2-fluoro-5-(2-methoxy-5-(trifluoromethyl)phenylamino)phenyl)-3,5,5,6-tetramethyl-5,6-dihydropyrimidin-4(3H)-one,
- (S)-2-Amino-6-(2-fluoro-5-(2-methoxyphenylamino)phenyl)-3,5,5,6-tetramethyl-5,6-dihydropyrimidin-4(3H)-one,
- (S)-2-Amino-6-(2-fluoro-5-(3,3,3-trifluoropropylamino)phenyl)-3,5,5,6-tetramethyl-5,6-dihydropyrimidin-4(3H)-one,
- (S)-2-Amino-6-(2-fluoro-5-(3-methoxyphenylamino)phenyl)-3,5,5,6-tetramethyl-5,6-dihydropyrimidin-4(3H)-one,
- (S)-2-amino-6-(2-fluoro-5-(4-(methylsulfonyl)phenylamino)phenyl)-3,5,5,6-tetramethyl-5,6-dihydropyrimidin-4(3H)-one,
- (S)-2-amino-6-(2-fluoro-5-(4-(trifluoromethyl)cyclohexylamino)phenyl)-3,5,5,6-tetramethyl-5,6-dihydropyrimidin-4(3H)-one,
- (S)-2-Amino-6-(2-fluoro-5-(4-fluoro-2-methoxyphenylamino)phenyl)-3,5,5,6-tetramethyl-5,6-dihydropyrimidin-4(3H)-one,
- (S)-2-Amino-6-(2-fluoro-5-(4-methoxyphenylamino)phenyl)-3,5,5,6-tetramethyl-5,6-dihydropyrimidin-4(3H)-one,
- (S)-2-amino-6-(2-fluoro-5-(5-(trifluoromethyl)pyridin-3-ylamino)phenyl)-3,5,5,6-tetramethyl-5,6-dihydropyrimidin-4(3H)-one,
- (S)-2-Amino-6-(2-fluoro-5-(5-fluoro-2-methoxyphenylamino)phenyl)-3,5,5,6-tetramethyl-5,6-dihydropyrimidin-4(3H)-one,
- (S)-2-amino-6-(2-fluoro-5-(5-fluoropyridin-3-ylamino)phenyl)-3,5,5,6-tetramethyl-5,6-dihydropyrimidin-4(3H)-one,
- (S)-2-amino-6-(2-fluoro-5-(6-(2,2,2-trifluoroethoxy)pyridin-3-ylamino)phenyl)-3,5,5,6-tetramethyl-5,6-dihydropyrimidin-4(3H)-one,
- (S)-2-amino-6-(2-fluoro-5-(6-(trifluoromethyl)pyridin-3-ylamino)phenyl)-3,5,5,6-tetramethyl-5,6-dihydropyrimidin-4(3H)-one,
- (S)-2-amino-6-(2-fluoro-5-(6-methoxypyridin-3-ylamino)phenyl)-3,5,5,6-tetramethyl-5,6-dihydropyrimidin-4(3H)-one, (S)-2-amino-6-(2-fluoro-5-(6-methylpyridin-3-ylamino)
phenyl)-3,5,5,6-tetramethyl-5,6-dihydropyrimidin-4
(3H)-one,
(S)-2-Amino-6-(2-fluoro-5-(neopentylamino)phenyl)-3,5,5,
6-tetramethyl-5,6-dihydropyrimidin-4(3H)-one,
(S)-2-Amino-6-(2-fluoro-5-(o-tolylamino)phenyl)-3,5,5,6-
tetramethyl-5,6-dihydropyrimidin-4(3H)-one,
(S)-2-amino-6-(2-fluoro-5-(phenylamino)phenyl)-3,5,5,6-
tetramethyl-5,6-dihydropyrimidin-4(3H)-one,
(S)-2-Amino-6-(2-fluoro-5-(p-tolylamino)phenyl)-3,5,5,6-
tetramethyl-5,6-dihydropyrimidin-4(3H)-one,
(S)-2-Amino-6-(2-fluoro-5-(pyridin-2-ylamino)phenyl)-3,5,
5,6-tetramethyl-5,6-dihydropyrimidin-4(3H)-one,
(S)-2-Amino-6-(2-fluoro-5-(pyridin-3-ylamino)phenyl)-3,5,
5,6-tetramethyl-5,6-dihydropyrimidin-4(3H)-one,
(S)-2-amino-6-(5-((4-chloro-1-(difluoromethyl)-1H-pyra-
zol-3-yl)methylamino)-2-fluorophenyl)-3,5,5,6-tetram-
ethyl-5,6-dihydropyrimidin-4(3H)-one,
(S)-2-Amino-6-(5-(1-benzyl-1H-pyrazol-5-ylamino)-2-
fluorophenyl)-3,5,5,6-tetramethyl-5,6-dihydropyrimidin-
4(3H)-one,
(S)-2-Amino-6-(5-(2-(difluoromethoxy)phenylamino)-2-
fluorophenyl)-3,5,5,6-tetramethyl-5,6-dihydropyrimidin-
4(3H)-one,
(S)-2-amino-6-(5-(2,2-dimethyl-2,3-dihydrobenzofuran-7-
ylamino)-2-fluorophenyl)-3,5,5,6-tetramethyl-5,6-dihy-
dropyrimidin-4(3H)-one,
(S)-2-amino-6-(5-(2,3-dihydrobenzofuran-7-ylamino)-2-
fluorophenyl)-3,5,5,6-tetramethyl-5,6-dihydropyrimidin-
4(3H)-one,
(S)-2-Amino-6-(5-(2,4-difluorophenylamino)-2-fluorophe-
nyl)-3,5,5,6-tetramethyl-5,6-dihydropyrimidin-4(3H)-
one,
(S)-2-Amino-6-(5-(2,4-dimethoxyphenylamino)-2-fluo-
rophenyl)-3,5,5,6-tetramethyl-5,6-dihydropyrimidin-4
(3H)-one,
(S)-2-Amino-6-(5-(2-chlorophenylamino)-2-fluorophenyl)-
3,5,5,6-tetramethyl-5,6-dihydropyrimidin-4(3H)-one,
(S)-2-amino-6-(5-(4-chloro-2-methoxy-5-methylpheny-
lamino)-2-fluorophenyl)-3,5,5,6-tetramethyl-5,6-dihy-
dropyrimidin-4(3H)-one,
(S)-2-amino-6-(5-(5-chloro-2-methoxyphenylamino)-2-
fluorophenyl)-3,5,5,6-tetramethyl-5,6-dihydropyrimidin-
4(3H)-one,
(S)-2-Amino-6-(5-(5-chloro-2-methylphenylamino)-2-fluo-
rophenyl)-3,5,5,6-tetramethyl-5,6-dihydropyrimidin-4
(3H)-one,
(S)-2-Amino-6-(5-(6-chloropyridin-3-ylamino)-2-fluo-
rophenyl)-3,5,5,6-tetramethyl-5,6-dihydropyrimidin-4
(3H)-one,
(S)-2-Amino-6-(5-(C-cyclopropylmethylamino)-2-fluo-
rophenyl)-3,5,5,6-tetramethyl-5,6-dihydropyrimidin-4
(3H)-one,
(S)-2-Amino-6-(5-(cyclopentylamino)-2-fluorophenyl)-3,5,
5,6-tetramethyl-5,6-dihydropyrimidin-4(3H)-one,
(S)-2-Amino-6-(5-ethylamino-2-fluoro-phenyl)-3,5,5,6-tet-
ramethyl-5,6-dihydro-3H-pyrimidin-4-one,
(S)-2-Amino-6-[2-fluoro-5-(1-methyl-1H-pyrazol-3-
ylamino)-phenyl]-3,5,5,6-tetramethyl-5,6-dihydro-3H-
pyrimidin-4-one,
(S)-2-Amino-6-[2-fluoro-5-(1-phenyl-ethylamino)-phenyl]-
3,5,5,6-tetramethyl-5,6-dihydro-3H-pyrimidin-4-one,
(S)-2-Amino-6-[2-fluoro-5-(1-phenyl-ethylamino)-phenyl]-
3,5,5,6-tetramethyl-5,6-dihydro-3H-pyrimidin-4-one,
(S)-2-Amino-6-[2-fluoro-5-(1-pyrimidin-2-yl-ethylamino)-
phenyl]-3,5,5,6-tetramethyl-5,6-dihydro-3H-pyrimidin-
4-one,
(S)-2-Amino-6-[2-fluoro-5-(2,2,2-trifluoro-1-methyl-ethy-
lamino)-phenyl]-3,5,5,6-tetramethyl-5,6-dihydro-3H-py-
rimidin-4-one,
(S)-2-Amino-6-[2-fluoro-5-(2-hydroxy-4,4-dimethyl-cyclo-
pentylamino)-phenyl]-3,5,5,6-tetramethyl-5,6-dihydro-
3H-pyrimidin-4-one,
(S)-2-Amino-6-[2-fluoro-5-(2-methoxy-(4-trifluorom-
ethyl)-phenylamino)-phenyl]-3,5,5,6-tetramethyl-5,6-di-
hydro-3H-pyrimidin-4-one,
(S)-2-Amino-6-[2-fluoro-5-(2-methyl-2H-pyrazol-3-
ylamino)-phenyl]-3,5,5,6-tetramethyl-5,6-dihydro-3H-
pyrimidin-4-one,
(S)-2-Amino-6-[2-fluoro-5-(2-methyl-cyclopentylamino)-
phenyl]-3,5,5,6-tetramethyl-5,6-dihydro-3H-pyrimidin-
4-one,
(S)-2-Amino-6-[2-fluoro-5-(3,3,3-trifluoro-2-methyl-pro-
pylamino)-phenyl]-3,5,5,6-tetramethyl-5,6-dihydro-3H-
pyrimidin-4-one,
(S)-2-Amino-6-[2-fluoro-5-(3,3,6-trimethyl-indan-1-
ylamino)-phenyl]-3,5,5,6-tetramethyl-5,6-dihydro-3H-
pyrimidin-4-one,
(S)-2-Amino-6-[2-fluoro-5-(3-fluoro-phenylamino)-phe-
nyl]-3,5,5,6-tetramethyl-5,6-dihydro-3H-pyrimidin-4-
one,
(S)-2-Amino-6-[2-fluoro-5-(3-methyl-cyclopentylamino)-
phenyl]-3,5,5,6-tetramethyl-5,6-dihydro-3H-pyrimidin-
4-one,
(S)-2-Amino-6-[2-fluoro-5-(4-fluoro-phenylamino)-phe-
nyl]-3,5,5,6-tetramethyl-5,6-dihydro-3H-pyrimidin-4-
one,
(S)-2-Amino-6-[2-fluoro-5-(4-methoxy-indan-1-ylamino)-
phenyl]-3,5,5,6-tetramethyl-5,6-dihydro-3H-pyrimidin-
4-one,
(S)-2-Amino-6-[2-fluoro-5-(7-fluoro-chroman-4-ylamino)-
phenyl]-3,5,5,6-tetramethyl-5,6-dihydro-3H-pyrimidin-
4-one,
(S)-2-Amino-6-[2-fluoro-5-(oxetan-3-ylamino)-phenyl]-3,
5,5,6-tetramethyl-5,6-dihydro-3H-pyrimidin-4-one,
(S)-2-Amino-6-[2-fluoro-5-(tetrahydro-furan-3-ylamino)-
phenyl]-3,5,5,6-tetramethyl-5,6-dihydro-3H-pyrimidin-
4-one,
(S)-2-Amino-6-[2-fluoro-5-(tetrahydro-pyran-3-ylamino)-
phenyl]-3,5,5,6-tetramethyl-5,6-dihydro-3H-pyrimidin-
4-one,
(S)-2-Amino-6-[2-fluoro-5-(tetrahydro-pyran-4-ylamino)-
phenyl]-3,5,5,6-tetramethyl-5,6-dihydro-3H-pyrimidin-
4-one,
(S)-2-Amino-6-[5-(1,1-dioxo-2,3-dihydro-1H-1-benzo[b]
thiophen-3-ylamino)-2-fluoro-phenyl]-3,5,5,6-tetram-
ethyl-5,6-dihydro-3H-pyrimidin-4-one,
(S)-2-Amino-6-[5-(1-benzothiazol-2-yl-ethylamino)-2-
fluoro-phenyl]-3,5,5,6-tetramethyl-5,6-dihydro-3H-pyri-
midin-4-one,
(S)-2-Amino-6-[5-(1-benzyl-piperidin-3-ylamino)-2-fluoro-
phenyl]-3,5,5,6-tetramethyl-5,6-dihydro-3H-pyrimidin-
4-one,
(S)-2-Amino-6-[5-(1-benzyl-piperidin-4-ylamino)-2-fluoro-
phenyl]-3,5,5,6-tetramethyl-5,6-dihydro-3H-pyrimidin-
4-one,
(S)-2-Amino-6-[5-(1-cyclopropyl-ethylamino)-2-fluoro-
phenyl]-3,5,5,6-tetramethyl-5,6-dihydro-3H-pyrimidin-
4-one,
(S)-2-Amino-6-[5-(2,5-difluoro-phenylamino)-2-fluoro-
phenyl]-3,5,5,6-tetramethyl-5,6-dihydro-3H-pyrimidin-
4-one, (S)-2-Amino-6-[5-(2,5-dimethoxy-phenylamino)-2-fluoro-phenyl]-3,5,5,6-tetramethyl-5,6-dihydro-3H-pyrimidin-4-one, (S)-2-Amino-6-[5-(2,5-dimethyl-2H-pyrazol-3-ylamino)-2-fluoro-phenyl]-3,5,5,6-tetramethyl-5,6-dihydro-3H-pyrimidin-4-one, (S)-2-Amino-6-[5-(3-ethyl-indan-1-ylamino)-2-fluoro-phenyl]-3,5,5,6-tetramethyl-5,6-dihydro-3H-pyrimidin-4-one, (S)-2-Amino-6-[5-(4,5-difluoro-2-methoxy-phenylamino)-2-fluoro-phenyl]-3,5,5,6-tetramethyl-5,6-dihydro-3H-pyrimidin-4-one, (S)-2-Amino-6-[5-(5-chloro-indan-1-ylamino)-2-fluoro-phenyl]-3,5,5,6-tetramethyl-5,6-dihydro-3H-pyrimidin-4-one, (S)-2-Amino-6-[5-(6-chloro-2,3-dihydro-benzofuran-3-ylamino)-2-fluoro-phenyl]-3,5,5,6-tetramethyl-5,6-dihydro-3H-pyrimidin-4-one, (S)-2-Amino-6-[5-(7-chloro-indan-1-ylamino)-2-fluoro-phenyl]-3,5,5,6-tetramethyl-5,6-dihydro-3H-pyrimidin-4-one, (S)-2-Amino-6-[5-(C-cyclobutylmethyl-amino)-2-fluoro-phenyl]-3,5,5,6-tetramethyl-5,6-dihydro-3H-pyrimidin-4-one, (S)-2-Amino-6-{2-fluoro-5-[((1R,2R)-2-phenyl-cyclopropylmethyl)-amino]-phenyl}-3,5,5,6-tetramethyl-5,6-dihydro-3H-pyrimidin-4-one, (S)-2-Amino-6-{2-fluoro-5-[(1H-pyrazol-3-ylmethyl)-amino]-phenyl}-3,5,5,6-tetramethyl-5,6-dihydro-3H-pyrimidin-4-one, (S)-2-Amino-6-{2-fluoro-5-[(1-methyl-1H-pyrazol-3-ylmethyl)-amino]-phenyl}-3,5,5,6-tetramethyl-5,6-dihydro-3H-pyrimidin-4-one, (S)-2-Amino-6-{2-fluoro-5-[(1-phenyl-cyclopropylmethyl)-amino]-phenyl}-3,5,5,6-tetramethyl-5,6-dihydro-3H-pyrimidin-4-one, (S)-2-Amino-6-{2-fluoro-5-[(1-trifluoromethyl-cyclopropylmethyl)-amino]-phenyl}-3,5,5,6-tetramethyl-5,6-dihydro-3H-pyrimidin-4-one, (S)-2-Amino-6-{2-fluoro-5-[(2-methyl-3H-imidazol-4-ylmethyl)-amino]-phenyl}-3,5,5,6-tetramethyl-5,6-dihydro-3H-pyrimidin-4-one, (S)-2-Amino-6-{2-fluoro-5-[(2-methyl-oxazol-4-ylmethyl)-amino]-phenyl}-3,5,5,6-tetramethyl-5,6-dihydro-3H-pyrimidin-4-one, (S)-2-Amino-6-{2-fluoro-5-[(3-methyl-oxetan-3-ylmethyl)-amino]-phenyl}-3,5,5,6-tetramethyl-5,6-dihydro-3H-pyrimidin-4-one, (S)-2-Amino-6-{2-fluoro-5-[(3-methyl-oxetan-3-ylmethyl)-amino]-phenyl}-3,5,5,6-tetramethyl-5,6-dihydro-3H-pyrimidin-4-one, (S)-2-Amino-6-{2-fluoro-5-[(4-methyl-2H-pyrazol-3-ylmethyl)-amino]-phenyl}-3,5,5,6-tetramethyl-5,6-dihydro-3H-pyrimidin-4-one, (S)-2-Amino-6-{2-fluoro-5-[(4-methyl-thiazol-5-ylmethyl)-amino]-phenyl}-3,5,5,6-tetramethyl-5,6-dihydro-3H-pyrimidin-4-one, (S)-2-Amino-6-{2-fluoro-5-[(5-methyl-isoxazol-3-ylmethyl)-amino]-phenyl}-3,5,5,6-tetramethyl-5,6-dihydro-3H-pyrimidin-4-one, (S)-2-Amino-6-{2-fluoro-5-[(isoxazol-3-ylmethyl)-amino]-phenyl}-3,5,5,6-tetramethyl-5,6-dihydro-3H-pyrimidin-4-one, (S)-2-Amino-6-{2-fluoro-5-[(pyridin-2-ylmethyl)-amino]-phenyl}-3,5,5,6-tetramethyl-5,6-dihydro-3H-pyrimidin-4-one, (S)-2-Amino-6-{2-fluoro-5-[(pyrimidin-2-ylmethyl)-amino]-phenyl}-3,5,5,6-tetramethyl-5,6-dihydro-3H-pyrimidin-4-one, (S)-2-Amino-6-{2-fluoro-5-[(tetrahydro-furan-3-ylmethyl)-amino]-phenyl}-3,5,5,6-tetramethyl-5,6-dihydro-3H-pyrimidin-4-one, (S)-2-Amino-6-{2-fluoro-5-[(tetrahydro-pyran-3-ylmethyl)-amino]-phenyl}-3,5,5,6-tetramethyl-5,6-dihydro-3H-pyrimidin-4-one, (S)-2-Amino-6-{2-fluoro-5-[1-(2H-pyrazol-3-yl)-ethylamino]-phenyl}-3,5,5,6-tetramethyl-5,6-dihydro-3H-pyrimidin-4-one, (S)-2-Amino-6-{2-fluoro-5-[1-(2-methyl-5-trifluoromethyl-oxazol-4-yl)-ethylamino]-phenyl}-3,5,5,6-tetramethyl-5,6-dihydro-3H-pyrimidin-4-one, (S)-2-Amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one, (S)-2-Amino-6-{2-fluoro-5-[2-(4-fluoro-phenyl)-1-methyl-ethylamino]-phenyl}-3,5,5,6-tetramethyl-5,6-dihydro-3H-pyrimidin-4-one, (S)-2-Amino-6-{5-[(2,2-difluoro-1-methyl-cyclopropylmethyl)-amino]-2-fluoro-phenyl}-3,5,5,6-tetramethyl-5,6-dihydro-3H-pyrimidin-4-one, (S)-2-Amino-6-{5-[(2,2-difluoro-cyclopropylmethyl)-amino]-2-fluoro-phenyl}-3,5,5,6-tetramethyl-5,6-dihydro-3H-pyrimidin-4-one, (S)-2-Amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one, (S)-2-Amino-6-{5-[(4-chloro-2H-pyrazol-3-ylmethyl)-amino]-2-fluoro-phenyl}-3,5,5,6-tetramethyl-5,6-dihydro-3H-pyrimidin-4-one, (S)-2-Amino-6-{5-[1-(4,5-dimethyl-thiazol-2-yl)-ethylamino]-2-fluoro-phenyl}-3,5,5,6-tetramethyl-5,6-dihydro-3H-pyrimidin-4-one, (S)-3-(3-(2-amino-1,4,5,5-tetramethyl-6-oxo-1,4,5,6-tetrahydropyrimidin-4-yl)-4-fluorophenylamino)-4-methoxybenzoic acid, (S)-3-(3-(2-amino-1,4,5,5-tetramethyl-6-oxo-1,4,5,6-tetrahydropyrimidin-4-yl)-4-fluorophenylamino)-4-fluorobenzonitrile, (S)-4-(3-(2-Amino-1,4,5,5-tetramethyl-6-oxo-1,4,5,6-tetrahydropyrimidin-4-yl)-4-fluorophenylamino)-3-methoxybenzoic acid, (S)-4-(3-(2-amino-1,4,5,5-tetramethyl-6-oxo-1,4,5,6-tetrahydropyrimidin-4-yl)-4-fluorophenylamino)-2-methylbenzonitrile, (S)-4-(3-(2-amino-1,4,5,5-tetramethyl-6-oxo-1,4,5,6-tetrahydropyrimidin-4-yl)-4-fluorophenylamino)-3-fluorobenzonitrile, (S)-4-(3-(2-amino-1,4,5,5-tetramethyl-6-oxo-1,4,5,6-tetrahydropyrimidin-4-yl)-4-fluorophenylamino)benzonitrile, (S)-4-(3-(2-amino-1,4,5,5-tetramethyl-6-oxo-1,4,5,6-tetrahydropyrimidin-4-yl)-4-fluorophenylamino)-3-(trifluoromethoxy)benzonitrile, (S)-4-(3-(2-amino-1,4,5,5-tetramethyl-6-oxo-1,4,5,6-tetrahydropyrimidin-4-yl)-4-fluorophenylamino)-3-(trifluoromethyl)benzonitrile, (S)-4-(3-(2-amino-1,4,5,5-tetramethyl-6-oxo-1,4,5,6-tetrahydropyrimidin-4-yl)-4-fluorophenylamino)-2,5-difluorobenzonitrile, (S)-6-(5-(1H-Pyrazol-5-ylamino)-2-fluorophenyl)-2-amino-3,5,5,6-tetramethyl-5,6-dihydropyrimidin-4(3H)-one hydrochloride, (S)-6-[5-(1-Acetyl-6-fluoro-2,3-dihydro-1H-indol-3-ylamino)-2-fluoro-phenyl]-2-amino-3,5,5,6-tetramethyl-5,6-dihydro-3H-pyrimidin-4-one, (S)-Methyl 3-(3-(2-amino-1,4,5,5-tetramethyl-6-oxo-1,4,5,6-tetrahydropyrimidin-4-yl)-4-fluorophenylamino)-4-methoxybenzoate, (S)-Methyl-4-(3-(2-amino-1,4,5,5-tetramethyl-6-oxo-1,4,5,6-tetrahydropyrimidin-4-yl)-4-fluorophenylamino)-3-methoxybenzoate, salt of (S)—N-(2'-Amino-1'-methyl-6'-oxo-2,3,5',6'-tetrahydro-1'H-spiro[indene-1,4'-pyrimidine]-6-yl)-1-(trifluoromethyl)-cyclopropanecarboxamide with trifluoro-acetic acid, salt of (S)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoro-acetic acid, salt of (S)—N-(3-(2-Amino-1,4,5,5-tetramethyl-6-oxo-1,4,5,6-tetrahydropyrimidin-4-yl)-4-fluorophenyl)-2-fluoro-2-methylpropanamide with trifluoro-acetic acid, salt of (S)—N-(3-(2-Amino-1,4,5,5-tetramethyl-6-oxo-1,4,5,6-tetrahydropyrimidin-4-yl)-4-fluorophenyl)cyclopropanecarboxamide with trifluoro-acetic acid, salt of (S)—N-(3-(2-Amino-1,4,5,5-tetramethyl-6-oxo-1,4,5,6-tetrahydropyrimidin-4-yl)-4-fluorophenyl)-1-methylcyclopropanecarboxamide with trifluoro-acetic acid, (S)—N-(3-(2-amino-1,4,5,5-tetramethyl-6-oxo-1,4,5,6-tetrahydropyrimidin-4-yl)-4-fluorophenyl)-2-cyclopentylacetamide, (S)—N-(3-(2-amino-1,4,5,5-tetramethyl-6-oxo-1,4,5,6-tetrahydropyrimidin-4-yl)-4-fluorophenyl)-2-cyclobutylacetamide, (S)—N-(3-(2-amino-1,4,5,5-tetramethyl-6-oxo-1,4,5,6-tetrahydropyrimidin-4-yl)-4-fluorophenyl)-2-cyclopropylacetamide, (S)—N-(3-(2-amino-1,4,5,5-tetramethyl-6-oxo-1,4,5,6-tetrahydropyrimidin-4-yl)-4-fluorophenyl)-1-hydroxycyclobutanecarboxamide 2,2,2-trifluoroacetate, (S)—N-(3-(2-amino-1,4,5,5-tetramethyl-6-oxo-1,4,5,6-tetrahydropyrimidin-4-yl)-4-fluorophenyl)-3,3,3-trifluoro-2-hydroxy-2-(trifluoromethyl)propanamide 2,2,2-trifluoroacetate, {3-[3-((S)-2-Amino-1,4,5,5-tetramethyl-6-oxo-1,4,5,6-tetrahydro-pyrimidin-4-yl)-4-fluoro-phenylamino]-cyclopentyl}-acetic acid methyl ester, {3-[3-((S)-2-Amino-1,4,5,5-tetramethyl-6-oxo-1,4,5,6-tetrahydro-pyrimidin-4-yl)-4-fluoro-phenylamino]-2,2-dimethyl-cyclopentyl}-acetic acid ethyl ester, 1-[3-((S)-2-Amino-1,4,5,5-tetramethyl-6-oxo-1,4,5,6-tetrahydro-pyrimidin-4-yl)-4-fluoro-phenylamino]-indan-4-carboxylic acid, 1-Hydroxy-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide, salt of 1-Trifluoromethyl-cyclobutanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid, salt of 1-Trifluoromethyl-cyclopropanecarboxylic acid [3-((4S,5R)-2-amino-5-ethyl-1,4-dimethyl-6-oxo-1,4,5,6-tetrahydro-pyrimidin-4-yl)-phenyl]-amide with trifluoro-acetic acid, salt of 1-Trifluoromethyl-cyclopropanecarboxylic acid [3-((R)-2-amino-1,4,5,5-tetramethyl-6-oxo-1,4,5,6-tetrahydro-pyrimidin-4-yl)-phenyl]-amide with trifluoro-acetic acid, salt of 1-Trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid, salt of 1-Trifluoromethyl-cyclopropanecarboxylic acid [3-((S)-2-amino-1,4-dimethyl-6-oxo-1,4,5,6-tetrahydro-pyrimidin-4-yl)-phenyl]-amide with trifluoro-acetic acid, salt of 1-Trifluoromethyl-cyclopropanecarboxylic acid [3-((S)-2-amino-1-c-cyclopropylmethyl-4-methyl-6-oxo-1,4,5,6-tetrahydro-pyrimidin-4-yl)-phenyl]-amide with trifluoro-acetic acid, salt of 1-Trifluoromethyl-cyclopropanecarboxylic acid [3-((S)-2-amino-1-methyl-6-oxo-4-propyl-1,4,5,6-tetrahydro-pyrimidin-4-yl)-phenyl]-amide; with trifluoro-acetic acid, 2-(3-(3-((S)-2-Amino-1,4,5,5-tetramethyl-6-oxo-1,4,5,6-tetrahydropyrimidin-4-yl)-4-fluorophenylamino)-2,3-dihydro-1H-inden-1-yl)acetic acid, 2-(3-(3-((S)-2-Amino-1,4,5,5-tetramethyl-6-oxo-1,4,5,6-tetrahydropyrimidin-4-yl)-4-fluorophenylamino)cyclopentyl)acetic acid, 2-(3-(3-((S)-2-Amino-1,4,5,5-tetramethyl-6-oxo-1,4,5,6-tetrahydropyrimidin-4-yl)-4-fluorophenylamino)-2,2-dimethylcyclopentyl)acetic acid, 2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile, 3-[3-((S)-2-Amino-1,4,5,5-tetramethyl-6-oxo-1,4,5,6-tetrahydro-pyrimidin-4-yl)-4-fluoro-phenylamino]-pyrrolidine-1-carboxylic acid ethyl ester, 3-[3-((S)-2-Amino-1,4,5,5-tetramethyl-6-oxo-1,4,5,6-tetrahydro-pyrimidin-4-yl)-4-fluoro-phenylamino]-benzonitrile, 4-[3-((S)-2-Amino-1,4,5,5-tetramethyl-6-oxo-1,4,5,6-tetrahydro-pyrimidin-4-yl)-4-fluoro-phenylamino]-3-chloro-benzonitrile, 5-[3-((S)-2-Amino-1,4,5,5-tetramethyl-6-oxo-1,4,5,6-tetrahydro-pyrimidin-4-yl)-4-fluoro-phenylamino]-2-methyl-benzonitrile, Acetic acid 5-[3-((S)-2-amino-1,4,5,5-tetramethyl-6-oxo-1,4,5,6-tetrahydro-pyrimidin-4-yl)-4-fluoro-phenylamino]-bicyclo[2.2.1]hept-2-yl ester, salt of N-(3-((S)-2-Amino-1,4,5,5-tetramethyl-6-oxo-1,4,5,6-tetrahydropyrimidin-4-yl)-4-fluorophenyl)-2,2-dimethylcyclopropanecarboxamide with trifluoro-acetic acid, salt of N-(3-((S)-2-Amino-1,4,5,5-tetramethyl-6-oxo-1,4,5,6-tetrahydropyrimidin-4-yl)-4-fluorophenyl)-2,3,3,3-tetrafluoro-2-methoxypropanamide with trifluoro-acetic acid, salt of N-[3-((S)-2-Amino-1,4,5,5-tetramethyl-6-oxo-1,4,5,6-tetrahydro-pyrimidin-4-yl)-4-fluoro-phenyl]-3,3,3-trifluoro-propionamide with trifluoro-acetic acid, salt of N-[3-((S)-2-Amino-1,4,5,5-tetramethyl-6-oxo-1,4,5,6-tetrahydro-pyrimidin-4-yl)-4-fluoro-phenyl]-2,2,3,3,3-pentafluoro-propionamide with trifluoro-acetic acid, salt of N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-trifluoromethyl-propionamide with trifluoro-acetic acid, salt of N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-hydroxy-propionamide with trifluoro-acetic acid, N-[3-((S)-2-Amino-1,4,5,5-tetramethyl-6-oxo-1,4,5,6-tetrahydro-pyrimidin-4-yl)-4-fluoro-phenyl]-2-hydroxy-2-phenyl-propionamide, N-[3-((S)-2-Amino-1,4,5,5-tetramethyl-6-oxo-1,4,5,6-tetrahydro-pyrimidin-4-yl)-4-fluoro-phenyl]-2-(4-chlorophenyl)-2-hydroxy-propionamide, and salt of N-[3-((S)-2-Amino-1,4,5,5-tetramethyl-6-oxo-1,4,5,6-tetrahydro-pyrimidin-4-yl)-4-fluoro-phenyl]-isobutyramide with trifluoro-acetic acid.

In a certain embodiment the invention relates to compounds of formula I as defined herein, selected from the group consisting of 1-cyano-cyclopropanecarboxylic acid [3-((R)-2-amino-1,4,5,5-tetramethyl-6-oxo-1,4,5,6-tetrahydro-pyrimidin-4-yl)-phenyl]-amide, 1-trifluoromethyl-cyclopropanecarboxylic acid [3-((R)-2-amino-1,4,5,5-tetramethyl-6-oxo-1,4,5,6-tetrahydro-pyrimidin-4-yl)-phenyl]-amide, N-[3-((S)-2-amino-1,4,5,5-tetramethyl-6-oxo-1,4,5,6-tetrahydro-pyrimidin-4-yl)-4-fluoro-phenyl]-3,3,3-trifluoropropionamide, 1-trifluoromethyl-cyclobutanecarboxylic acid [3-((S)-2-amino-1,4,5,5-tetramethyl-6-oxo-1,4,5,6-tetrahydro-pyrimidin-4-yl)-4-fluoro-phenyl]-amide, 1-trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide, N-[3-((S)-2-amino-1,4,5,5-tetramethyl-6-oxo-1,4,5,6-tetrahydro-pyrimidin-4-yl)-4-fluoro-phenyl]-2,2,3,3,3-pentafluoro-propionamide, N-[3-((S)-2-amino-1,4,5,5-tetramethyl-6-oxo-1,4,5,6-tetrahydro-pyrimidin-4-yl)-4-fluoro-phenyl]-3,3,3-trifluoro-2-trifluoromethyl-propionamide, N-[3-((S)-2-amino-1,4,5,5-tetramethyl-6-oxo-1,4,5,6-tetrahydro-pyrimidin-4-yl)-4-fluoro-phenyl]-3,3,3-trifluoro-2-hydroxy-propionamide, (R)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide, (S)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide, 1-trifluoromethyl-cyclopropanecarboxylic acid [3-((4S,5R)-2-amino-5-ethyl-1,4-dimethyl-6-oxo-1,4,5,6-tetrahydropyrimidin-4-yl)-phenyl]-amide, 1-trifluoromethyl-cyclopropanecarboxylic acid [3-((S)-2-amino-1,4-dimethyl-6-oxo-1,4,5,6-tetrahydro-pyrimidin-4-yl)-phenyl]-amide, 1-trifluoromethyl-cyclopropanecarboxylic acid [3-((S)-2-amino-1-c-cyclopropylmethyl-4-methyl-6-oxo-1,4,5,6-tetrahydro-pyrimidin-4-yl)-phenyl]-amide, 1-trifluoromethyl-cyclopropanecarboxylic acid [3-((S)-2-amino-1-methyl-6-oxo-4-propyl-1,4,5,6-tetrahydro-pyrimidin-4-yl)-phenyl]-amide, (S)—N-(2'-amino-1'-methyl-6'-oxo-2,3,5',6'-tetrahydro-1'H-spiro[indene-1,4'-pyrimidine]-6-yl)-1-(trifluoromethyl)cyclopropanecarboxamide, (S)—N-(3-(2-amino-1,4,5,5-tetramethyl-6-oxo-1,4,5,6-tetrahydropyrimidin-4-yl)-4-fluorophenyl)-2-fluoro-2-methylpropanamide, (S)—N-(3-(2-amino-1,4,5,5-tetramethyl-6-oxo-1,4,5,6-tetrahydropyrimidin-4-yl)-4-fluorophenyl)cyclopropanecarboxamide, (S)—N-(3-(2-amino-1,4,5,5-tetramethyl-6-oxo-1,4,5,6-tetrahydropyrimidin-4-yl)-4-fluorophenyl)-1-methylcyclopropanecarboxamide, N-(3-((S)-2-amino-1,4,5,5-tetramethyl-6-oxo-1,4,5,6-tetrahydropyrimidin-4-yl)-4-fluorophenyl)-2,2-dimethylcyclopropanecarboxamide, N-(3-((S)-2-amino-1,4,5,5-tetramethyl-6-oxo-1,4,5,6-tetrahydropyrimidin-4-yl)-4-fluorophenyl)-2,3,3,3-tetrafluoro-2-methoxypropanamide, (S)-2-amino-6-(5-(cyclopentylamino)-2-fluorophenyl)-3,5,5,6-tetramethyl-5,6-dihydropyrimidin-4(3H)-one, (S)-2-amino-6-[2-fluoro-5-(tetrahydro-furan-3-ylamino)-phenyl]-3,5,5,6-tetramethyl-5,6-dihydro-3H-pyrimidin-4-one, 3-[3-((S)-2-amino-1,4,5,5-tetramethyl-6-oxo-1,4,5,6-tetrahydro-pyrimidin-4-yl)-4-fluoro-phenylamino]-pyrrolidine-1-carboxylic acid ethyl ester, (S)-2-amino-6-[2-fluoro-5-(3-methyl-cyclopentylamino)-phenyl]-3,5,5,6-tetramethyl-5,6-dihydro-3H-pyrimidin-4-one, (S)-2-amino-6-[2-fluoro-5-(2-methyl-cyclopentylamino)-phenyl]-3,5,5,6-tetramethyl-5,6-dihydro-3H-pyrimidin-4-one, (S)—N-(3-(2-amino-1,4,5,5-tetramethyl-6-oxo-1,4,5,6-tetrahydropyrimidin-4-yl)-4-fluorophenyl)-2-cyclopentylacetamide, (S)—N-(3-(2-amino-1,4,5,5-tetramethyl-6-oxo-1,4,5,6-tetrahydropyrimidin-4-yl)-4-fluorophenyl)-2-cyclobutylacetamide, (S)—N-(3-(2-amino-1,4,5,5-tetramethyl-6-oxo-1,4,5,6-tetrahydropyrimidin-4-yl)-4-fluorophenyl)-2-cyclopropylacetamide, (S)-2-amino-6-[5-(5-chloro-indan-1-ylamino)-2-fluoro-phenyl]-3,5,5,6-tetramethyl-5,6-dihydro-3H-pyrimidin-4-one, (6S)-2-amino-6-(5-(2-chlorocyclopentylamino)-2-fluorophenyl)-3,5,5,6-tetramethyl-5,6-dihydropyrimidin-4(3H)-one, (6S)-2-amino-6-(2-fluoro-5-(1-(4-fluorophenyl)pyrrolidin-3-ylamino)phenyl)-3,5,5,6-tetramethyl-5,6-dihydropyrimidin-4(3H)-one, (6S)-2-amino-6-(5-(1-benzylpyrrolidin-3-ylamino)-2-fluorophenyl)-3,5,5,6-tetramethyl-5,6-dihydropyrimidin-4(3H)-one, (6S)-2-amino-6-(2-fluoro-5-(3-phenylcyclopentylamino)phenyl)-3,5,5,6-tetramethyl-5,6-dihydropyrimidin-4(3H)-one, (6S)-2-amino-6-(2-fluoro-5-(2-methyltetrahydrofuran-3-ylamino)phenyl)-3,5,5,6-tetramethyl-5,6-dihydropyrimidin-4(3H)-one, (6S)-2-amino-6-(2-fluoro-5-(5-fluoro-2,3-dihydro-1H-inden-1-ylamino)phenyl)-3,5,5,6-tetramethyl-5,6-dihydropyrimidin-4(3H)-one, (S)-2-amino-6-[2-fluoro-5-(2-methyl-2H-pyrazol-3-ylamino)-phenyl]-3,5,5,6-tetramethyl-5,6-dihydro-3H-pyrimidin-4-one, (S)-2-amino-6-[5-(1-cyclopropyl-ethylamino)-2-fluoro-phenyl]-3,5,5,6-tetramethyl-5,6-dihydro-3H-pyrimidin-4-one, (S)-2-amino-6-[2-fluoro-5-(1-phenyl-ethylamino)-phenyl]-3,5,5,6-tetramethyl-5,6-dihydro-3H-pyrimidin-4-one, (S)-2-amino-6-[5-(2,5-dimethyl-2H-pyrazol-3-ylamino)-2-fluoro-phenyl]-3,5,5,6-tetramethyl-5,6-dihydro-3H-pyrimidin-4-one, (S)-2-amino-6-[2-fluoro-5-(1-phenyl-ethylamino)-phenyl]-3,5,5,6-tetramethyl-5,6-dihydro-3H-pyrimidin-4-one, (S)-2-amino-6-(2-fluoro-5-(4-(trifluoromethyl)cyclohexylamino)phenyl)-3,5,5,6-tetramethyl-5,6-dihydropyrimidin-4(3H)-one, (S)-2-amino-6-{2-fluoro-5-[2-(4-fluoro-phenyl)-1-methyl-ethylamino]-phenyl}-3,5,5,6-tetramethyl-5,6-dihydro-3H-pyrimidin-4-one, (S)-2-amino-6-[5-(1-benzyl-piperidin-4-ylamino)-2-fluoro-phenyl]-3,5,5,6-tetramethyl-5,6-dihydro-3H-pyrimidin-4-one, (S)-2-amino-6-[5-(1-benzyl-piperidin-3-ylamino)-2-fluoro-phenyl]-3,5,5,6-tetramethyl-5,6-dihydro-3H-pyrimidin-4-one, (S)-2-amino-6-[2-fluoro-5-(tetrahydro-pyran-3-ylamino)-phenyl]-3,5,5,6-tetramethyl-5,6-dihydro-3H-pyrimidin-4-one, (S)-2-amino-6-[2-fluoro-5-(3,3,6-trimethyl-indan-1-ylamino)-phenyl]-3,5,5,6-tetramethyl-5,6-dihydro-3H-pyrimidin-4-one, (S)-2-amino-6-[2-fluoro-5-(4-methoxy-indan-1-ylamino)-phenyl]-3,5,5,6-tetramethyl-5,6-dihydro-3H-pyrimidin-4-one, (S)-2-amino-6-(2-fluoro-5-(phenylamino)phenyl)-3,5,5,6-tetramethyl-5,6-dihydropyrimidin-4(3H)-one, (S)-2-amino-6-[5-(7-chloro-indan-1-ylamino)-2-fluoro-phenyl]-3,5,5,6-tetramethyl-5,6-dihydro-3H-pyrimidin-4-one, (S)-2-amino-6-[2-fluoro-5-(tetrahydro-pyran-4-ylamino)-phenyl]-3,5,5,6-tetramethyl-5,6-dihydro-3H-pyrimidin-4-one, (6S)-2-amino-6-(5-(2,3-dihydrobenzofuran-3-ylamino)-2-fluorophenyl)-3,5,5,6-tetramethyl-5,6-dihydropyrimidin-4(3H)-one, (S)-2-amino-6-(5-(C-cyclopropylmethylamino)-2-fluorophenyl)-3,5,5,6-tetramethyl-5,6-dihydropyrimidin-4(3H)-one (S)-2-amino-6-{2-fluoro-5-[(1-phenyl-cyclopropylmethyl)-amino]-phenyl}-3,5,5,6-tetramethyl-5,6-dihydro-3H-pyrimidin-4-one (S)-2-amino-6-(2-fluoro-5-(3,3,3-trifluoropropylamino)phenyl)-3,5,5,6-tetramethyl-5,6-dihydropyrimidin-4(3H)-one, (S)-2-amino-6-(2-fluoro-5-(o-tolylamino)phenyl)-3,5,5,6-tetramethyl-5,6-dihydropyrimidin-4(3H)-one, (S)-2-amino-6-(2-fluoro-5-(2-methoxyphenylamino)phenyl)-3,5,5,6-tetramethyl-5,6-dihydropyrimidin-4(3H)-one, (S)-2-amino-6-(2-fluoro-5-(neopentylamino)phenyl)-3,5,5,6-tetramethyl-5,6-dihydropyrimidin-4(3H)-one, (S)-2-amino-6-{5-[(2,2-difluoro-cyclopropylmethyl)-amino]-2-fluoro-phenyl}-3,5,5,6-tetramethyl-5,6-dihydro-3H-pyrimidin-4-one, (S)-2-amino-6-{2-fluoro-5-[(pyridin-2-ylmethyl)-amino]-phenyl}-3,5,5,6-tetramethyl-5,6-dihydro-3H-pyrimidin-4-one, (S)-2-amino-6-{2-fluoro-5-[(1-methyl-1H-pyrazol-3-ylmethyl)-amino]-phenyl}-3,5,5,6-tetramethyl-5,6-dihydro-3H-pyrimidin-4-one, (S)-2-amino-6-{2-fluoro-5-[(1H-pyrazol-3-ylmethyl)-amino]-phenyl}-3,5,5,6-tetramethyl-5,6-dihydro-3H-pyrimidin-4-one, (6S)-2-amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one, (6S)-2-amino-6-(2-fluoro-5-(7-fluoro-2,3-dihydro-1H-inden-1-ylamino)phenyl)-3,5,5,6-tetramethyl-5,6-dihydropyrimidin-4(3H)-one, (S)-2-amino-6-[2-fluoro-5-(2,2,2-trifluoro-1-methyl-ethylamino)-phenyl]-3,5,5,6-tetramethyl-5,6-dihydro-3H-pyrimidin-4-one, 2-(3-(3-((S)-2-amino-1,4,5,5-tetramethyl-6-oxo-1,4,5,6-tetrahydropyrimidin-4-yl)-4-fluorophenylamino)-2,3-dihydro-1H-inden-1-yl)acetic acid, (S)-2-amino-6-(2-fluoro-5-(p-tolylamino)phenyl)-3,5,5,6-tetramethyl-5,6-dihydropyrimidin-4(3H)-one, (6S)-2-amino-6-(2-fluoro-5-(7-methyl-2,3-dihydro-1H-inden-1-ylamino)phenyl)-3,5,5,6-tetramethyl-5,6-dihydropyrimidin-4(3H)-one, (S)-2-amino-6-{5-[(2,2-difluoro-1-methyl-cyclopropylmethyl)-amino]-2-fluoro-phenyl}-3,5,5,6-tetramethyl-5,6-dihydro-3H-pyrimidin-4-one, (S)-2-amino-6-(2-fluoro-5-(2-fluorophenylamino)phenyl)-3,5,5,6-tetramethyl-5,6-dihydropyrimidin-4(3H)-one, (S)-2-amino-6-[5-(C-cyclobutylmethyl-amino)-2-fluoro-phenyl]-3,5,5,6-tetramethyl-5,6-dihydro-3H-pyrimidin-4-one, (S)-2-amino-6-{2-fluoro-5-[(3-methyl-oxetan-3-ylmethyl)-amino]-phenyl}-3,5,5,6-tetramethyl-5,6-dihydro-3H-pyrimidin-4-one, (S)-2-amino-6-(2-fluoro-5-(4-methoxyphenylamino)phenyl)-3,5,5,6-tetramethyl-5,6-dihydropyrimidin-4(3H)-one, (S)-2-amino-6-(5-(2-(difluoromethoxy)phenylamino)-2-fluorophenyl)-3,5,5,6-tetramethyl-5,6-dihydropyrimidin-4(3H)-one, (S)-2-amino-6-(2-fluoro-5-(2-(trifluoromethoxy)phenylamino)phenyl)-3,5,5,6-tetramethyl-5,6-dihydropyrimidin-4(3H)-one, (S)-2-amino-6-(2-fluoro-5-(2,2,2-trifluoroethylamino)phenyl)-3,5,5,6-tetramethyl-5,6-dihydropyrimidin-4(3H)-one, (S)-2-amino-6-{2-fluoro-5-[(tetrahydro-furan-3-ylmethyl)-amino]-phenyl}-3,5,5,6-tetramethyl-5,6-dihydro-3H-pyrimidin-4-one, (S)-2-amino-6-{2-fluoro-5-[(2-methyl-3H-imidazol-4-ylmethyl)-amino]-phenyl}-3,5,5,6-tetramethyl-5,6-dihydro-3H-pyrimidin-4-one, (S)-2-amino-6-{2-fluoro-5-[(4-methyl-thiazol-5-ylmethyl)-amino]-phenyl}-3,5,5,6-tetramethyl-5,6-dihydro-3H-pyrimidin-4-one, (S)-2-amino-6-(2-fluoro-5-(3-methoxyphenylamino)phenyl)-3,5,5,6-tetramethyl-5,6-dihydropyrimidin-4(3H)-one, (S)-2-amino-6-[2-fluoro-5-(1-pyrimidin-2-yl-ethylamino)-phenyl]-3,5,5,6-tetramethyl-5,6-dihydro-3H-pyrimidin-4-one, (S)-2-amino-6-(5-(2,4-difluorophenylamino)-2-fluorophenyl)-3,5,5,6-tetramethyl-5,6-dihydropyrimidin-4(3H)-one, (S)-2-amino-6-(2-fluoro-5-(4-fluoro-2-methoxyphenylamino)phenyl)-3,5,5,6-tetramethyl-5,6-dihydropyrimidin-4(3H)-one, (S)-2-amino-6-[2-fluoro-5-(3,3,3-trifluoro-2-methyl-propylamino)-phenyl]-3,5,5,6-tetramethyl-5,6-dihydro-3H-pyrimidin-4-one, (S)-2-amino-6-(2-fluoro-5-(5-fluoro-2-methoxyphenylamino)phenyl)-3,5,5,6-tetramethyl-5,6-dihydropyrimidin-4(3H)-one, (S)-2-amino-6-{2-fluoro-5-[(pyrimidin-2-ylmethyl)-amino]-phenyl}-3,5,5,6-tetramethyl-5,6-dihydro-3H-pyrimidin-4-one, (S)-2-amino-6-{2-fluoro-5-[(isoxazol-3-ylmethyl)-amino]-phenyl}-3,5,5,6-tetramethyl-5,6-dihydro-3H-pyrimidin-4-one, (S)-2-amino-6-{2-fluoro-5-[(1-trifluoromethyl-cyclopropylmethyl)-amino]-phenyl}-3,5,5,6-tetramethyl-5,6-dihydro-3H-pyrimidin-4-one, (S)-2-amino-6-[2-fluoro-5-(3-fluoro-phenylamino)-phenyl]-3,5,5,6-tetramethyl-5,6-dihydro-3H-pyrimidin-4-one, (S)-2-amino-6-[2-fluoro-5-(4-fluoro-phenylamino)-phenyl]-3,5,5,6-tetramethyl-5,6-dihydro-3H-pyrimidin-4-one,
(S)-2-amino-6-{2-fluoro-5-[(tetrahydro-pyran-3-ylmethyl)-amino]-phenyl}-3,5,5,6-tetramethyl-5,6-dihydro-3H-pyrimidin-4-one,
(S)-2-amino-6-(5-ethylamino-2-fluoro-phenyl)-3,5,5,6-tetramethyl-5,6-dihydro-3H-pyrimidin-4-one,
(S)-2-amino-6-(2-fluoro-5-((1S,2S)-2-hydroxycyclopentylamino)phenyl)-3,5,5,6-tetramethyl-5,6-dihydropyrimidin-4(3H)-one,
acetic acid 5-[3-((S)-2-amino-1,4,5,5-tetramethyl-6-oxo-1,4,5,6-tetrahydro-pyrimidin-4-yl)-4-fluoro-phenylamino]-bicyclo[2.2.1]hept-2-yl ester,
(S)-2-amino-6-[2-fluoro-5-(2-methoxy-(4-trifluoromethyl)-phenylamino)-phenyl]-3,5,5,6-tetramethyl-5,6-dihydro-3H-pyrimidin-4-one,
{3-[3-((S)-2-amino-1,4,5,5-tetramethyl-6-oxo-1,4,5,6-tetrahydro-pyrimidin-4-yl)-4-fluoro-phenylamino]-cyclopentyl}-acetic acid methyl ester,
(S)-2-amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one,
(S)-2-amino-6-{2-fluoro-5-[((1R,2R)-2-phenyl-cyclopropylmethyl)-amino]-phenyl}-3,5,5,6-tetramethyl-5,6-dihydro-3H-pyrimidin-4-one,
{3-[3-((S)-2-amino-1,4,5,5-tetramethyl-6-oxo-1,4,5,6-tetrahydro-pyrimidin-4-yl)-4-fluoro-phenylamino]-2,2-dimethyl-cyclopentyl}-acetic acid ethyl ester,
(S)-2-amino-6-[2-fluoro-5-(1-methyl-1H-pyrazol-3-ylamino)-phenyl]-3,5,5,6-tetramethyl-5,6-dihydro-3H-pyrimidin-4-one,
(1S,3R,5R,6S)-ethyl 2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylate,
(S)-2-amino-6-(2-fluoro-5-(5-hydroxybicyclo[2.2.1]heptan-2-ylamino)phenyl)-3,5,5,6-tetramethyl-5,6-dihydropyrimidin-4(3H)-one,
(S)-2-amino-6-[5-(4,5-difluoro-2-methoxy-phenylamino)-2-fluoro-phenyl]-3,5,5,6-tetramethyl-5,6-dihydro-3H-pyrimidin-4-one,
(S)-2-(3-(2-amino-1,4,5,5-tetramethyl-6-oxo-1,4,5,6-tetrahydropyrimidin-4-yl)-4-fluorophenylamino)benzonitrile,
(S)-2-amino-6-{2-fluoro-5-[(5-methyl-isoxazol-3-ylmethyl)-amino]-phenyl}-3,5,5,6-tetramethyl-5,6-dihydro-3H-pyrimidin-4-one,
(S)-2-amino-6-(2-fluoro-5-(pyridin-2-ylamino)phenyl)-3,5,5,6-tetramethyl-5,6-dihydropyrimidin-4(3H)-one,
(S)-2-amino-6-(5-(3,3-dimethyl-2,3-dihydro-1H-inden-1-ylamino)-2-fluorophenyl)-3,5,5,6-tetramethyl-5,6-dihydropyrimidin-4(3H)-one,
(S)-2-amino-6-(5-(1-benzyl-1H-pyrazol-5-ylamino)-2-fluorophenyl)-3,5,5,6-tetramethyl-5,6-dihydropyrimidin-4(3H)-one,
(S)-2-amino-6-(5-(2,4-dimethoxyphenylamino)-2-fluorophenyl)-3,5,5,6-tetramethyl-5,6-dihydropyrimidin-4(3H)-one,
(S)-2-amino-6-{2-fluoro-5-[(2-methyl-oxazol-4-ylmethyl)-amino]-phenyl}-3,5,5,6-tetramethyl-5,6-dihydro-3H-pyrimidin-4-one,
(S)-2-amino-6-{2-fluoro-5-[(4-methyl-2H-pyrazol-3-ylmethyl)-amino]-phenyl}-3,5,5,6-tetramethyl-5,6-dihydro-3H-pyrimidin-4-one,
(S)-2-amino-6-{2-fluoro-5-[1-(2H-pyrazol-3-yl)-ethylamino]-phenyl}-3,5,5,6-tetramethyl-5,6-dihydro-3H-pyrimidin-4-one,
(S)-2-amino-6-(5-(5-chloro-3,3-dimethyl-2,3-dihydro-1H-inden-1-ylamino)-2-fluorophenyl)-3,5,5,6-tetramethyl-5,6-dihydropyrimidin-4(3H)-one,
(S)-2-amino-6-[5-(3-ethyl-indan-1-ylamino)-2-fluoro-phenyl]-3,5,5,6-tetramethyl-5,6-dihydro-3H-pyrimidin-4-one,
(S)-2-amino-6-(2-fluoro-5-(5-fluoro-2-methyl-2,3-dihydro-1H-inden-1-ylamino)phenyl)-3,5,5,6-tetramethyl-5,6-dihydropyrimidin-4(3H)-one,
2-(3-(3-((S)-2-amino-1,4,5,5-tetramethyl-6-oxo-1,4,5,6-tetrahydropyrimidin-4-yl)-4-fluorophenylamino)cyclopentyl)acetic acid,
2-(3-(3-((S)-2-amino-1,4,5,5-tetramethyl-6-oxo-1,4,5,6-tetrahydropyrimidin-4-yl)-4-fluorophenylamino)-2,2-dimethylcyclopentyl)acetic acid,
(1S,3R,5R,6S)-2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylic acid,
(S)-2-amino-6-(5-(5-chloro-2-methylphenylamino)-2-fluorophenyl)-3,5,5,6-tetramethyl-5,6-dihydropyrimidin-4(3H)-one,
(S)-2-amino-6-(5-(2-chlorophenylamino)-2-fluorophenyl)-3,5,5,6-tetramethyl-5,6-dihydropyrimidin-4(3H)-one,
(S)-2-amino-6-[5-(2,5-dimethoxy-phenylamino)-2-fluoro-phenyl]-3,5,5,6-tetramethyl-5,6-dihydro-3H-pyrimidin-4-one,
(S)-2-amino-6-(2-fluoro-5-(2-methoxy-5-(trifluoromethyl)phenylamino)phenyl)-3,5,5,6-tetramethyl-5,6-dihydropyrimidin-4(3H)-one,
(S)-methyl 3-(3-(2-amino-1,4,5,5-tetramethyl-6-oxo-1,4,5,6-tetrahydropyrimidin-4-yl)-4-fluorophenylamino)-4-methoxybenzoate,
(S)-methyl-4-(3-(2-amino-1,4,5,5-tetramethyl-6-oxo-1,4,5,6-tetrahydropyrimidin-4-yl)-4-fluorophenylamino)-3-methoxybenzoate,
(S)-6-(5-(1H-pyrazol-5-ylamino)-2-fluorophenyl)-2-amino-3,5,5,6-tetramethyl-5,6-dihydropyrimidin-4(3H)-one,
(S)-2-amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one,
(S)-2-amino-6-{5-[1-(4,5-dimethyl-thiazol-2-yl)-ethylamino]-2-fluoro-phenyl}-3,5,5,6-tetramethyl-5,6-dihydro-3H-pyrimidin-4-one,
(S)-2-amino-6-[5-(1-benzothiazol-2-yl-ethylamino)-2-fluoro-phenyl]-3,5,5,6-tetramethyl-5,6-dihydro-3H-pyrimidin-4-one,
(S)-2-amino-6-{5-[(4-chloro-2H-pyrazol-3-ylmethyl)-amino]-2-fluoro-phenyl}-3,5,5,6-tetramethyl-5,6-dihydro-3H-pyrimidin-4-one,
(S)-3-(3-(2-amino-1,4,5,5-tetramethyl-6-oxo-1,4,5,6-tetrahydropyrimidin-4-yl)-4-fluorophenylamino)-4-methoxybenzoic acid,
(S)-4-(3-(2-amino-1,4,5,5-tetramethyl-6-oxo-1,4,5,6-tetrahydropyrimidin-4-yl)-4-fluorophenylamino)-3-methoxybenzoic acid,
(S)-2-amino-6-{2-fluoro-5-[(3-methyl-oxetan-3-ylmethyl)-amino]-phenyl}-3,5,5,6-tetramethyl-5,6-dihydro-3H-pyrimidin-4-one,
(S)-2-amino-6-[2-fluoro-5-(oxetan-3-ylamino)-phenyl]-3,5,5,6-tetramethyl-5,6-dihydro-3H-pyrimidin-4-one,
(S)-2-amino-6-[5-(6-chloro-2,3-dihydro-benzofuran-3-ylamino)-2-fluoro-phenyl]-3,5,5,6-tetramethyl-5,6-dihydro-3H-pyrimidin-4-one,
1-hydroxy-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide, 2-[3-((S)-2-amino-1,4,5,5-tetramethyl-6-oxo-1,4,5,6-tetrahydro-pyrimidin-4-yl)-4-fluoro-phenylamino]-cyclopentanecarbonitrile, 1-[3-((S)-2-amino-1,4,5,5-tetramethyl-6-oxo-1,4,5,6-tetrahydro-pyrimidin-4-yl)-4-fluoro-phenylamino]-indan-4-carboxylic acid, (S)-6-[5-(1-acetyl-6-fluoro-2,3-dihydro-1H-indol-3-ylamino)-2-fluoro-phenyl]-2-amino-3,5,5,6-tetramethyl-5,6-dihydro-3H-pyrimidin-4-one, (S)-2-amino-6-(2-fluoro-5-(pyridin-3-ylamino)phenyl)-3,5,5,6-tetramethyl-5,6-dihydropyrimidin-4(3H)-one, N-[3-((S)-2-amino-1,4,5,5-tetramethyl-6-oxo-1,4,5,6-tetrahydro-pyrimidin-4-yl)-4-fluoro-phenyl]-2-hydroxy-2-phenyl-propionamide, (S)-2-amino-6-[2-fluoro-5-(7-fluoro-chroman-4-ylamino)-phenyl]-3,5,5,6-tetramethyl-5,6-dihydro-3H-pyrimidin-4-one, N-[3-((S)-2-amino-1,4,5,5-tetramethyl-6-oxo-1,4,5,6-tetrahydro-pyrimidin-4-yl)-4-fluoro-phenyl]-2-(4-chlorophenyl)-2-hydroxy-propionamide, (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide, (S)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide, (S)-2-amino-6-[5-(1,1-dioxo-2,3-dihydro-1H-1-benzo[b]thiophen-3-ylamino)-2-fluoro-phenyl]-3,5,5,6-tetramethyl-5,6-dihydro-3H-pyrimidin-4-one, (S)-2-amino-6-[5-(2,5-difluoro-phenylamino)-2-fluoro-phenyl]-3,5,5,6-tetramethyl-5,6-dihydro-3H-pyrimidin-4-one, (S)-2-amino-6-(2-fluoro-5-(2,4,5-trimethylphenylamino)phenyl)-3,5,5,6-tetramethyl-5,6-dihydropyrimidin-4(3H)-one, and pharmaceutically acceptable salts thereof.

In a certain embodiment the invention relates to compounds of formula I as defined herein, selected from the group consisting of salt of 1-Trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid, (6S)-2-Amino-6-(2-fluoro-5-(5-hydroxybicyclo[2.2.1]heptan-2-ylamino)phenyl)-3,5,5,6-tetramethyl-5,6-dihydropyrimidin-4(3H)-one, (6S)-2-Amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one, salt of (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoro-acetic acid, (S)-2-Amino-6-(2-fluoro-5-(2-methoxy-5-(trifluoromethyl)phenylamino)phenyl)-3,5,5,6-tetramethyl-5,6-dihydropyrimidin-4(3H)-one, (S)-2-Amino-6-(2-fluoro-5-(pyridin-2-ylamino)phenyl)-3,5,5,6-tetramethyl-5,6-dihydropyrimidin-4(3H)-one, (S)-2-Amino-6-[2-fluoro-5-(1-methyl-1H-pyrazol-3-ylamino)-phenyl]-3,5,5,6-tetramethyl-5,6-dihydro-3H-pyrimidin-4-one, (S)-2-Amino-6-[2-fluoro-5-(tetrahydro-furan-3-ylamino)-phenyl]-3,5,5,6-tetramethyl-5,6-dihydro-3H-pyrimidin-4-one, (S)-2-Amino-6-[2-fluoro-5-(tetrahydro-pyran-3-ylamino)-phenyl]-3,5,5,6-tetramethyl-5,6-dihydro-3H-pyrimidin-4-one, (S)-2-Amino-6-[2-fluoro-5-(tetrahydro-pyran-4-ylamino)-phenyl]-3,5,5,6-tetramethyl-5,6-dihydro-3H-pyrimidin-4-one, (S)-2-Amino-6-[5-(1,1-dioxo-2,3-dihydro-1H-1-benzo[b]thiophen-3-ylamino)-2-fluoro-phenyl]-3,5,5,6-tetramethyl-5,6-dihydro-3H-pyrimidin-4-one, (S)-2-Amino-6-{2-fluoro-5-[(5-methyl-isoxazol-3-ylmethyl)-amino]-phenyl}-3,5,5,6-tetramethyl-5,6-dihydro-3H-pyrimidin-4-one, (S)-2-Amino-6-{2-fluoro-5-[(tetrahydro-furan-3-ylmethyl)-amino]-phenyl}-3,5,5,6-tetramethyl-5,6-dihydro-3H-pyrimidin-4-one, (S)-2-Amino-6-{2-fluoro-5-[1-(2H-pyrazol-3-yl)-ethylamino]-phenyl}-3,5,5,6-tetramethyl-5,6-dihydro-3H-pyrimidin-4-one, (S)-2-Amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one, (S)-2-Amino-6-{5-[(2,2-difluoro-cyclopropylmethyl)-amino]-2-fluoro-phenyl}-3,5,5,6-tetramethyl-5,6-dihydro-3H-pyrimidin-4-one, (S)-2-Amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one, (S)-2-Amino-6-{5-[(4-chloro-2H-pyrazol-3-ylmethyl)-amino]-2-fluoro-phenyl}-3,5,5,6-tetramethyl-5,6-dihydro-3H-pyrimidin-4-one, 2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile, and salt of N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-hydroxy-propionamide with trifluoro-acetic acid.

A certain embodiment of present invention is concerned with compounds of the formula

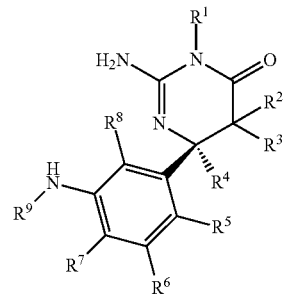

wherein $R^1$ is selected from the group consisting of hydrogen, $C_{1-7}$-alkyl, $C_{3-7}$-cycloalkyl, $C_{3-7}$-cycloalkyl-$C_{1-7}$-alkyl and benzyl;

$R^2$ is selected from the group consisting of hydrogen, $C_{1-7}$-alkyl and $C_{3-7}$-cycloalkyl;

$R^3$ is selected from the group consisting of hydrogen, $C_{1-7}$-alkyl and $C_{3-7}$-cycloalkyl;

or $R^2$ and $R^3$ together with the C atom they are attached to form a $C_{3-7}$-cycloalkyl ring;

$R^4$ is $C_{1-7}$-alkyl or $C_{3-7}$-cycloalkyl;

$R^5$ is selected from the group consisting of hydrogen, $C_{1-7}$-alkyl, halogen, cyano and $C_{1-7}$-alkoxy;

or $R^4$ and $R^5$ together are —$(CH_2)_m$— with m being 2 or 3 and thus form a ring;

$R^6$, $R^7$ and $R^8$ independently from each other are selected from hydrogen and halogen; and
$R^9$ is —(CO)—$R^{10}$ or —$R^{11}$, wherein
$R^{10}$ is selected from the group consisting of
—(CHR$^{12}$)$_m$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, benzyl and phenyl, said phenyl being unsubstituted or substituted by halogen, $R^{12}$ is hydrogen or C$_{1-7}$-alkyl, and m is 0, 1 or 2,
halogen-C$_{1-7}$-alkyl,
hydroxy-halogen-C$_{1-7}$-alkyl,
C$_{1-7}$-alkoxy-halogen-C$_{1-7}$-alkyl,
—(CHR$^{13}$)$_n$-heterocyclyl, wherein heterocyclyl is unsubstituted or substituted by one, two or three groups selected from the group consisting of C$_{1-7}$-alkyl, halogen, halogen-C$_{1-7}$-alkyl, cyano, benzyl and phenyl, said phenyl being unsubstituted or substituted by halogen, $R^{13}$ is hydrogen or C$_{1-7}$-alkyl, and n is 0, 1 or 2, and
—CH(OH)-phenyl, wherein phenyl is unsubstituted or substituted by halogen; and
$R^{11}$ is selected from the group consisting of
C$_{1-7}$-alkyl,
—(CHR$^{14}$)$_p$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyloxy, benzyl and phenyl, said phenyl being unsubstituted or substituted by halogen, $R^{14}$ is hydrogen or C$_{1-7}$-alkyl, and p is 0, 1 or 2,
halogen-C$_{1-7}$-alkyl,
indanyl, being unsubstituted or substituted by one, two or three groups selected from the group consisting of C$_{1-7}$-alkyl, C$_{1-7}$-alkoxy, carboxyl, carboxyl-C$_{1-7}$-alkyl and halogen,
tetrahydronaphtalenyl, being unsubstituted or substituted by one, two or three groups selected from C$_{1-7}$-alkyl and halogen,
6,7-dihydro-5H-cyclopenta[b]pyridinyl, being unsubstituted or substituted by one, two or three groups selected from C$_{1-7}$-alkyl and halogen,
hydroxy-halogen-C$_{1-7}$-alkyl,
C$_{1-7}$-alkoxy-halogen-C$_{1-7}$-alkyl,
—(CHR$^{15}$)$_q$-heterocyclyl, wherein heterocyclyl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyl, C$_{1-7}$-alkylcarbonyloxy, oxo, C$_{3-7}$-cycloalkyl, imidazolyl, benzyl, phenylsulfanyl and phenyl, said phenyl being unsubstituted or substituted by halogen, $R^{15}$ is hydrogen or C$_{1-7}$-alkyl, and q is 0, 1 or 2;
—(CHR$^{16}$)$_s$-aryl, wherein aryl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, $R^{16}$ is hydrogen or C$_{1-7}$-alkyl, and s is 0, 1 or 2;
—(CHR$^{17}$)$_t$-heteroaryl, wherein heteroaryl is unsubstituted or substituted by one, two or three groups selected from the group consisting of C$_{1-7}$-alkyl, halogen, halogen-C$_{1-7}$-alkyl, hydroxy, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, and t is 0, 1 or 2;
or pharmaceutically acceptable salts thereof.

The present invention thus relates to compounds of formula I as defined above, wherein $R^1$ is C$_{1-7}$-alkyl or C$_{3-7}$-cycloalkyl-C$_{1-7}$-alkyl. In particular, the invention relates to compounds of formula I, wherein $R^1$ is C$_{1-7}$-alkyl, more particularly methyl.

Compounds of formula I according to the invention are further those, wherein $R^2$ and $R^3$ are independently from each other selected from hydrogen and C$_{1-7}$-alkyl. In particular, the invention relates to compounds of formula I, wherein $R^2$ and $R^3$ are C$_{1-7}$-alkyl, more particularly $R^2$ and $R^3$ are methyl. The invention also relates to compounds of formula I, wherein $R^2$ and $R^3$ are hydrogen.

The invention further relates to compounds of formula I, wherein $R^4$ is C$_{1-7}$-alkyl. More particularly, $R^4$ is methyl or ethyl.

Another group of compounds of formula I of the present invention are those, wherein $R^4$ and $R^5$ together are —(CH$_2$)$_m$— with m being 2 or 3 and thus form a ring. In particular, m is 2.

The invention further relates to compounds of formula I, wherein $R^5$ is hydrogen or halogen. In particular, $R^5$ is halogen, more particularly fluoro.

$R^6$, $R^7$ and $R^8$ are selected from hydrogen or halogen. In particular, the invention refers to compounds of formula I, wherein $R^6$, $R^7$ and $R^8$ are hydrogen.

Compounds of formula I according to the present invention are further those, wherein $R^9$ is —(CO)—$R^{10}$ and $R^{10}$ is selected from the group consisting of
—(CHR$^{12}$)$_m$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, benzyl and phenyl, said phenyl being unsubstituted or substituted by halogen, $R^{12}$ is hydrogen or C$_{1-7}$-alkyl, and m is 0, 1 or 2,
halogen-C$_{1-7}$-alkyl,
hydroxy-halogen-C$_{1-7}$-alkyl,
C$_{1-7}$-alkoxy-halogen-C$_{1-7}$-alkyl,
—(CHR$^{13}$)$_n$-heterocyclyl, wherein heterocyclyl is unsubstituted or substituted by one, two or three groups selected from the group consisting of C$_{1-7}$-alkyl, halogen, halogen-C$_{1-7}$-alkyl, cyano, benzyl and phenyl, said phenyl being unsubstituted or substituted by halogen, $R^{13}$ is hydrogen or C$_{1-7}$-alkyl, $R^{13}$ is hydrogen or C$_{1-7}$-alkyl, and n is 0, 1 or 2, and
—CH(OH)-phenyl, wherein phenyl is unsubstituted or substituted by halogen.

Furthermore, the invention relates to compounds of formula I, wherein $R^9$ is —(CO)—$R^{10}$ and $R^{10}$ is selected from the group consisting of
—(CHR$^{12}$)$_m$—C$_{3-7}$-cycloalkyl, wherein cycloalkyl is unsubstituted or substituted by one, two or three groups selected from the group consisting of C$_{1-7}$-alkyl, hydroxy, halogen, halogen-C$_{1-7}$-alkyl, cyano, benzyl and phenyl, said phenyl being unsubstituted or substituted by halogen, $R^{12}$ is hydrogen or C$_{1-7}$-alkyl, and m is 0, 1 or 2,
—(CHR$^{13}$)$_n$-heterocyclyl, wherein heterocyclyl is unsubstituted or substituted by one, two or three groups selected from the group consisting of C$_{1-7}$-alkyl, halogen, halogen-C$_{1-7}$-alkyl, cyano, benzyl and phenyl, said phenyl being unsubstituted or substituted by halogen, $R^{13}$ is hydrogen or C$_{1-7}$-alkyl, and n is 0, 1 or 2, and
—CH(OH)-phenyl, wherein phenyl is unsubstituted or substituted by halogen.

A particular group of compounds of formula I according to the invention are those, wherein $R^{10}$ is —$(CHR^{12})_m$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, benzyl and phenyl, said phenyl being unsubstituted or substituted by halogen, $R^{12}$ is hydrogen or $C_{1-7}$-alkyl, and m is 0, 1 or 2. More particularly, cycloalkyl is selected from cyclopropyl, cyclobutyl and cyclopentyl. In particular, m is 0 or 1.

Another group of compounds of formula I according to the invention are those, wherein $R^{10}$ is selected from the group consisting of halogen-$C_{1-7}$-alkyl, hydroxy-halogen-$C_{1-7}$-alkyl, and $C_{1-7}$-alkoxy-halogen-$C_{1-7}$-alkyl.

A further group of compounds of formula I according to the invention are those, wherein $R^9$ is $R^{11}$ and $R^{11}$ is selected from the group consisting of $C_{1-7}$-alkyl, —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, halogen-$C_{1-7}$-alkyl, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, hydroxy-halogen-$C_{1-7}$-alkyl, $C_{1-7}$-alkoxy-halogen-$C_{1-7}$-alkyl, —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—$(CHR^{16})_s$-aryl, wherein aryl being unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2.

The invention thus also relates to a group of compounds of formula I, wherein $R^9$ is $R^{11}$ and $R^{11}$ is selected from the group consisting of —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—$(CHR^{16})_s$-aryl, wherein aryl being unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2.

In particular, the invention relates to compounds of formula I, wherein $R^9$ is $R^{11}$ and $R^{11}$ is —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, in particular hydrogen, and p is 0, 1 or 2. In particular, p is 0 or 1. More particularly, cycloalkyl is selected from the group consisting of cyclopropyl, cyclobutyl, cyclopentyl, cyclohexyl, bicyclo[2.2.1]heptyl and bicyclo[3.1.0]hexyl.

The invention also relates to compounds of formula I, wherein $R^9$ is $R^{11}$ and $R^{11}$ is selected from the group consisting of indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl and halogen, 6,7-dihydro-5H-cyclopenta[b]pyridinyl, being unsubstituted or substituted by one, two or three groups selected from $C_{1-7}$-alkyl and halogen, and —(CHR$^{15}$)$_q$-heterocyclyl, wherein heterocyclyl is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyl, C$_{1-7}$-alkylcarbonyloxy, oxo, C$_{3-7}$-cycloalkyl, imidazolyl, benzyl, phenylsulfanyl and phenyl, said phenyl being unsubstituted or substituted by halogen, R$^{15}$ is hydrogen or C$_{1-7}$-alkyl, and q is 0, 1 or 2.

In particular, R$^{11}$ is —(CHR$^{15}$)$_q$-heterocyclyl, wherein heterocyclyl is selected from the group consisting of oxetanyl, tetrahydrofuranyl, tetrahydropyranyl, pyrrolidinyl, piperidinyl, 2,3-dihydrobenzofuranyl, 2,3-dihydro-1H-indolyl, chromanyl and 2,3-dihydro-1H-benzo[b]thienyl and is unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, carboxyl-C$_{1-7}$-alkyl, C$_{1-7}$-alkoxycarbonyl-C$_{1-7}$-alkyl, C$_{1-7}$-alkylcarbonyl, C$_{1-7}$-alkylcarbonyloxy, oxo, C$_{3-7}$-cycloalkyl, imidazolyl, benzyl, phenylsulfanyl and phenyl, said phenyl being unsubstituted or substituted by halogen, R$^{15}$ is hydrogen or C$_{1-7}$-alkyl, and q is 0 or 1.

Furthermore, the invention relates to compounds of formula I, wherein R$^9$ is R$^{11}$ and R$^{11}$ is —(CHR$^{16}$)$_s$-aryl, wherein aryl being unsubstituted or substituted by one, two or three groups selected from the group consisting of C$_{1-7}$-alkyl, hydroxy, halogen, halogen-C$_{1-7}$-alkyl, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, R$^{16}$ is hydrogen or C$_{1-7}$-alkyl, and s is 0, 1 or 2.

Further compounds of formula I according to the invention are those, wherein R$^9$ is R$^{11}$ and R$^{11}$ is —(CHR$^{17}$)$_t$-heteroaryl, wherein heteroaryl is unsubstituted or substituted by one, two or three groups selected from the group consisting of C$_{1-7}$-alkyl, halogen, halogen-C$_{1-7}$-alkyl, hydroxy, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, and t is 0, 1 or 2.

In particular, R$^{11}$ is —(CHR$^{17}$)$_t$-heteroaryl, wherein heteroaryl is selected from the group consisting of pyrazolyl, imdazolyl, ozazolyl, thiazolyl, pyridyl, pyrimidinyl and benzothiazolyl and is unsubstituted or substituted by one, two or three groups selected from the group consisting of C$_{1-7}$-alkyl, halogen, halogen-C$_{1-7}$-alkyl, hydroxy, C$_{1-7}$-alkoxy, halogen-C$_{1-7}$-alkoxy, cyano, hydroxy-C$_{1-7}$-alkyl, carboxyl, C$_{1-7}$-alkoxycarbonyl, oxo, C$_{3-7}$-cycloalkyl, imidazolyl, benzyl, phenylsulfanyl and phenyl, said phenyl being unsubstituted or substituted by halogen, and t is 0 or 1.

The invention also refers to compounds of formula I, wherein R$^9$ is R$^{11}$ and R$^{11}$ is selected from the group consisting of C$_{1-7}$-alkyl, halogen-C$_{1-7}$-alkyl, hydroxy-halogen-C$_{1-7}$-alkyl and C$_{1-7}$-alkoxy-halogen-C$_{1-7}$-alkyl.

The pharmaceutically acceptable salts of the compounds of formula I also individually constitute compounds of the present invention.

In particular, the invention relates to the salts of compounds of formula I with HCl, formic acid and trifluoroacetic acid (CF$_3$COOH), i.e. the chloride salts, the formate salts and trifluoroacetate salts.

For example, the invention relates to the following pharmaceutically acceptable salts:

salt of 1-cyano-cyclopropanecarboxylic acid [3-((R)-2-amino-1,4,5,5-tetramethyl-6-oxo-1,4,5,6-tetrahydro-pyrimidin-4-yl)-phenyl]-amide with trifluoroacetic acid, salt of 1-trifluoromethyl-cyclopropanecarboxylic acid [3-((R)-2-amino-1,4,5,5-tetramethyl-6-oxo-1,4,5,6-tetrahydro-pyrimidin-4-yl)-phenyl]-amide with trifluoroacetic acid, salt of N-[3-((S)-2-amino-1,4,5,5-tetramethyl-6-oxo-1,4,5,6-tetrahydro-pyrimidin-4-yl)-4-fluoro-phenyl]-3,3,3-trifluoro-propionamide and with trifluoroacetic acid, salt of 1-trifluoromethyl-cyclobutanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoroacetic acid, salt of 1-trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoroacetic acid, salt of N-[3-((S)-2-amino-1,4,5,5-tetramethyl-6-oxo-1,4,5,6-tetrahydro-pyrimidin-4-yl)-4-fluoro-phenyl]-2,2,3,3,3-pentafluoro-propionamide with trifluoroacetic acid, salt of N-[3-((S)-2-amino-1,4,5,5-tetramethyl-6-oxo-1,4,5,6-tetrahydro-pyrimidin-4-yl)-4-fluoro-phenyl]-3,3,3-trifluoro-2-trifluoromethyl-propionamide with trifluoroacetic acid, salt of N-[3-((S)-2-amino-1,4,5,5-tetramethyl-6-oxo-1,4,5,6-tetrahydro-pyrimidin-4-yl)-4-fluoro-phenyl]-3,3,3-trifluoro-2-hydroxy-propionamide with trifluoroacetic acid, salt of (R)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoroacetic acid, salt of (S)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoroacetic acid, salt of 1-trifluoromethyl-cyclopropanecarboxylic acid [3-((4S,5R)-2-amino-5-ethyl-1,4-dimethyl-6-oxo-1,4,5,6-tetrahydro-pyrimidin-4-yl)-phenyl]-amide with trifluoroacetic acid, salt of 1-trifluoromethyl-cyclopropanecarboxylic acid [3-((S)-2-amino-1,4-dimethyl-6-oxo-1,4,5,6-tetrahydro-pyrimidin-4-yl)-phenyl]-amide with trifluoroacetic acid, salt of 1-trifluoromethyl-cyclopropanecarboxylic acid [3-((S)-2-amino-1-c-cyclopropylmethyl-4-methyl-6-oxo-1,4,5,6-tetrahydro-pyrimidin-4-yl)-phenyl]-amide with trifluoroacetic acid, salt of 1-trifluoromethyl-cyclopropanecarboxylic acid [3-((S)-2-amino-1-methyl-6-oxo-4-propyl-1,4,5,6-tetrahydro-pyrimidin-4-yl)-phenyl]-amide with trifluoroacetic acid, salt of (S)—N-(2'-amino-1'-methyl-6'-oxo-2,3,5',6'-tetrahydro-1'H-spiro[indene-1,4'-pyrimidine]-6-yl)-1-(trifluoromethyl)cyclopropanecarboxamide with trifluoroacetic acid, salt of (S)—N-(3-(2-amino-1,4,5,5-tetramethyl-6-oxo-1,4,5,6-tetrahydropyrimidin-4-yl)-4-fluorophenyl)-2-fluoro-2-methylpropanamide with trifluoroacetic acid, salt of (S)—N-(3-(2-amino-1,4,5,5-tetramethyl-6-oxo-1,4,5,6-tetrahydropyrimidin-4-yl)-4-fluorophenyl)cyclopropanecarboxamide with trifluoroacetic acid, salt of (S)—N-(3-(2-amino-1,4,5,5-tetramethyl-6-oxo-1,4,5,6-tetrahydropyrimidin-4-yl)-4-fluorophenyl)-1-methylcyclopropanecarboxamide with trifluoroacetic acid, salt of N-(3-((S)-2-amino-1,4,5,5-tetramethyl-6-oxo-1,4,5,6-tetrahydropyrimidin-4-yl)-4-fluorophenyl)-2,2-dimethylcyclopropanecarboxamide with trifluoroacetic acid, salt of N-(3-((S)-2-amino-1,4,5,5-tetramethyl-6-oxo-1,4,5,6-tetrahydropyrimidin-4-yl)-4-fluorophenyl)-2,3,3,3-tetrafluoro-2-methoxypropanamide with trifluoroacetic acid, (S)-6-(5-(1H-pyrazol-5-ylamino)-2-fluorophenyl)-2-amino-3,5,5,6-tetramethyl-5,6-dihydropyrimidin-4(3H)-one hydrochloride, salt of (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoroacetic acid, and salt of (S)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoroacetic acid.

More particularly, the invention relates to the following compounds:

salt of 1-trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid, salt of N-[3-((S)-2-amino-1,4,5,5-tetramethyl-6-oxo-1,4,5,6-tetrahydro-pyrimidin-4-yl)-4-fluoro-phenyl]-3,3,3-trifluoro-2-hydroxy-propionamide with trifluoro-acetic acid, salt of (S)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid, (S)-2-amino-6-[2-fluoro-5-(tetrahydro-furan-3-ylamino)-phenyl]-3,5,5,6-tetramethyl-5,6-dihydro-3H-pyrimidin-4-one, (S)-2-amino-6-[2-fluoro-5-(tetrahydro-pyran-3-ylamino)-phenyl]-3,5,5,6-tetramethyl-5,6-dihydro-3H-pyrimidin-4-one, (S)-2-amino-6-[2-fluoro-5-(tetrahydro-pyran-4-ylamino)-phenyl]-3,5,5,6-tetramethyl-5,6-dihydro-3H-pyrimidin-4-one, (S)-2-amino-6-{5-[(2,2-difluoro-cyclopropylmethyl)-amino]-2-fluoro-phenyl}-3,5,5,6-tetramethyl-5,6-dihydro-3H-pyrimidin-4-one, (S)-2-amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one, (S)-2-amino-6-{2-fluoro-5-[(tetrahydro-furan-3-ylmethyl)-amino]-phenyl}-3,5,5,6-tetramethyl-5,6-dihydro-3H-pyrimidin-4-one, (S)-2-amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one, (S)-2-amino-6-[2-fluoro-5-(1-methyl-1H-pyrazol-3-ylamino)-phenyl]-3,5,5,6-tetramethyl-5,6-dihydro-3H-pyrimidin-4-one, (6S)-2-amino-6-(2-fluoro-5-(5-hydroxybicyclo[2.2.1]heptan-2-ylamino)phenyl)-3,5,5,6-tetramethyl-5,6-dihydropyrimidin-4(3H)-one, (S)-2-amino-6-{2-fluoro-5-[(5-methyl-isoxazol-3-ylmethyl)-amino]-phenyl}-3,5,5,6-tetramethyl-5,6-dihydro-3H-pyrimidin-4-one, (S)-2-amino-6-(2-fluoro-5-(pyridin-2-ylamino)phenyl)-3,5,5,6-tetramethyl-5,6-dihydropyrimidin-4(3H)-one, (S)-2-amino-6-{2-fluoro-5-[1-(2H-pyrazol-3-yl)-ethylamino]-phenyl}-3,5,5,6-tetramethyl-5,6-dihydro-3H-pyrimidin-4-one, (S)-2-amino-6-(2-fluoro-5-(2-methoxy-5-(trifluoromethyl)phenylamino)phenyl)-3,5,5,6-tetramethyl-5,6-dihydropyrimidin-4(3H)-one, (S)-2-amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one, (S)-2-amino-6-{5-[(4-chloro-2H-pyrazol-3-ylmethyl)-amino]-2-fluoro-phenyl}-3,5,5,6-tetramethyl-5,6-dihydro-3H-pyrimidin-4-one, 2-[3-((S)-2-amino-1,4,5,5-tetramethyl-6-oxo-1,4,5,6-tetrahydro-pyrimidin-4-yl)-4-fluoro-phenylamino]-cyclopentanecarbonitrile, salt of (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoroacetic acid, and (S)-2-amino-6-[5-(1,1-dioxo-2,3-dihydro-1H-1-benzo[b]thiophen-3-ylamino)-2-fluoro-phenyl]-3,5,5,6-tetramethyl-5,6-dihydro-3H-pyrimidin-4-one.

The skilled person in the art will recognize that the compounds of formula I can exist in tautomeric forms, e.g. in the following tautomeric form:

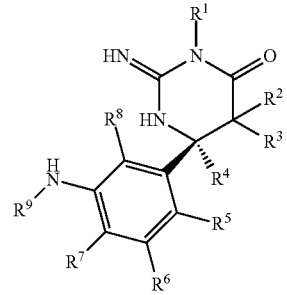

I-Tautomer all tautomeric forms are encompassed in the present invention.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting an amine of the formula II

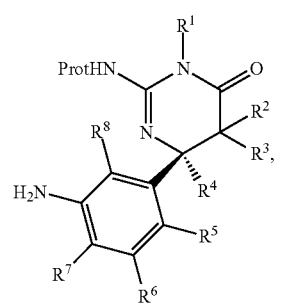

II wherein $R^1$ to $R^8$ are as defined herein before and Prot is an amino protecting group, with a carboxylic acid of the formula III

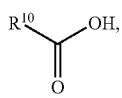

wherein $R^{10}$ is as defined herein before, in the presence of a coupling reagent under basic conditions to obtain a compound of the formula IV

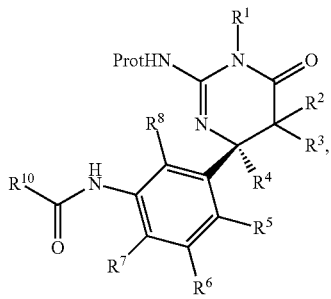

and deprotecting the compound of formula IV with the help of an acid to obtain a compound of the formula

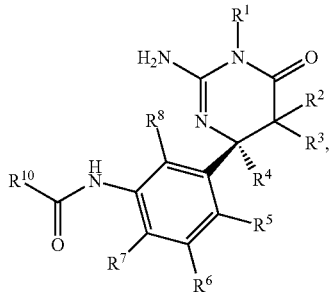

wherein $R^1$ to $R^8$ and $R^{10}$ are as defined herein before, or b) reacting an amine of the formula V

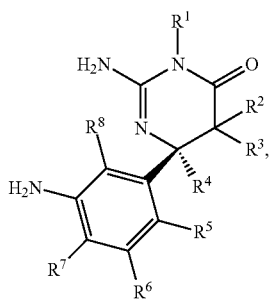

wherein $R^1$ to $R^8$ are as defined herein before, with a carbonyl compound of the formula VI

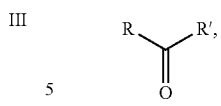

wherein R and R' together with the carbon atom of the carbonyl function correspond to the residue $R^{11}$, in the presence of a borohydride and an acid to obtain a compound of the formula Ib

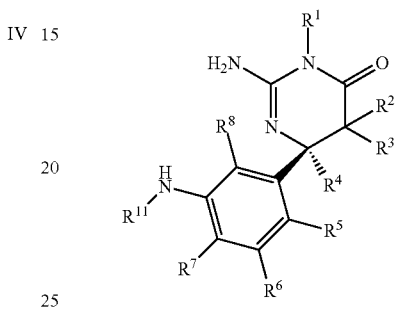

wherein $R^1$ to $R^8$ and $R^{11}$ are as defined herein before, or c) coupling a bromide of the formula VII

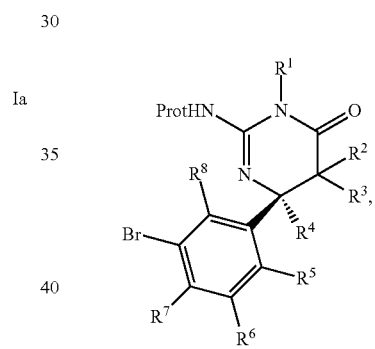

wherein $R^1$ to $R^8$ are as defined in claim 1 and Prot is an amino protecting group, with an amine of the formula

$R^{11}$—$NH_2$  VIII, wherein $R^{11}$ is as defined in claim 1, with a Pd catalyst in the presence of a base to obtain a compound of the formula IX

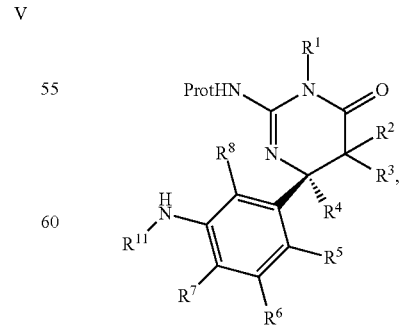

and deprotecting the compound of formula IX with the help of an acid to obtain a compound of the formula

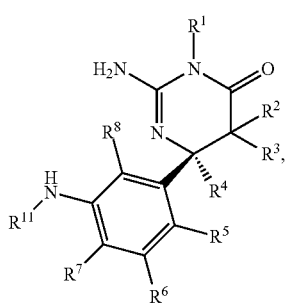

wherein R¹ to R⁸ and R¹¹ are as defined in claim 1.

The term "amino protecting group" as used herein refers to a substituent commonly employed to block or protect the amino functionality while reacting other functional groups on the compound. Suitable amino protecting groups are selected from the group consisting of formyl, benzyl and ester groups such as benzyloxycarbonyl ("Cbz"), 9-fluorenylmethoxycarbonyl ("FMOC"), tert-butoxycarbonyl ("BOC") and allyloxycarbonyl, and arylsulfonyl derivatives such as para-toluenesulfonyl, benzylsulfonyl and phenylsulfonyl. The selection and use (addition and subsequent removal) of amino protecting groups is well known to the skilled in the art and for instance described in T. W. Greene and P. G. M. Wuts, Protective Groups in Organic Synthesis, 3ʳ edition, John Wiley and Sons, New York, N.Y., 1999. A particular suitable amino protecting group is BOC.

Appropriate coupling reagents are carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU) and 1-[bis(dimethylamino)methylene]-1H-1,2,3-triazolo[4,5-b]pyridinium-3-oxide hexafluorophosphate (HATU). The term "under basic conditions" means the presence of a base, preferably an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF) or dimethylacetamide (DMAc), at temperatures between 0° C. and ambient temperature.

Acids suitable for the deprotection are mineral acids such as sulfuric acid or hydrochloric acid, in particular hydrochloric acid in a solvent such as an ether, preferably diethyl ether or 1,4-dioxane, or carbonic acids such as neat trifluoroacetic acid.

"In the presence of a borohydride" means that the reductive amination in process alternative b) as defined above can be accomplished with a borohydride such as sodium borohydride or sodium cyanoborohydride (optionally modified with Zn Cl₂) or particularly sodium triacetoxyborohydride or decaborane in the presence of an acid, e.g. a carbonic acid such as acetic acid, in a solvent such as THF or dichloroethane. Usually, temperatures between 20° C. and 50° C. are used.

The Pd catalyst used in process alternative c) as defined above an be selected from the group consisting of Pd(OAc)₂ or Pd₂(dba)₃ and a ligand, e.g. 2-dicyclohexylphosphino-2',4',6'-triisopropylbiphenyl (XPhos), 4,5-bis(diphenylphosphino)-9,9-dimethylxanthene (Xantphos), rac-2,2'-bis(diphenylphosphino)-1,1'-binaphthyl (BINAP), preferably 2-di-tert-butylphosphino-2',4',6'-triisopropylbiphenyl (tBuXphos) or 2-dicyclohexylphosphino-2'-(N,N-dimethylamino)biphenyl (Davephos). The coupling is carried in the presence of a base such as Cs₂CO₃, K₂CO₃, K₃PO₄, NaOPh, or particularly, t-BuONa and heating to temperatures between 100° C. and 110° C. Suitable solvents include 1,4-dioxane, dimethoxyethane, tBuOH and in particular toluene.

The invention further relates to compounds of formula I as defined above obtainable according to a process as defined above.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In more detail, compounds of formula I according to the present invention can be prepared by the methods and procedures given below.

Sulfinyl imines of general formula A can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium (IV) alkoxyde, more preferably titanium(IV) ethoxide in a solvent such as an ether, e.g. diethyl ether or more preferably THF.

The conversion of the sulfinyl imine A to the sulfinamide ester B proceeds stereoselectively by the chiral directing group as described by Tang & Ellman. The sulfinyl imine A can be reacted with a titanium enolate generated from e.g. an alkyl acetate, preferably methyl acetate, LDA and chlorotriisopropoxytitanium at low temperature, preferably at −78° C. in a solvent such as an ether, e.g. diethyl ether or more preferably THF.

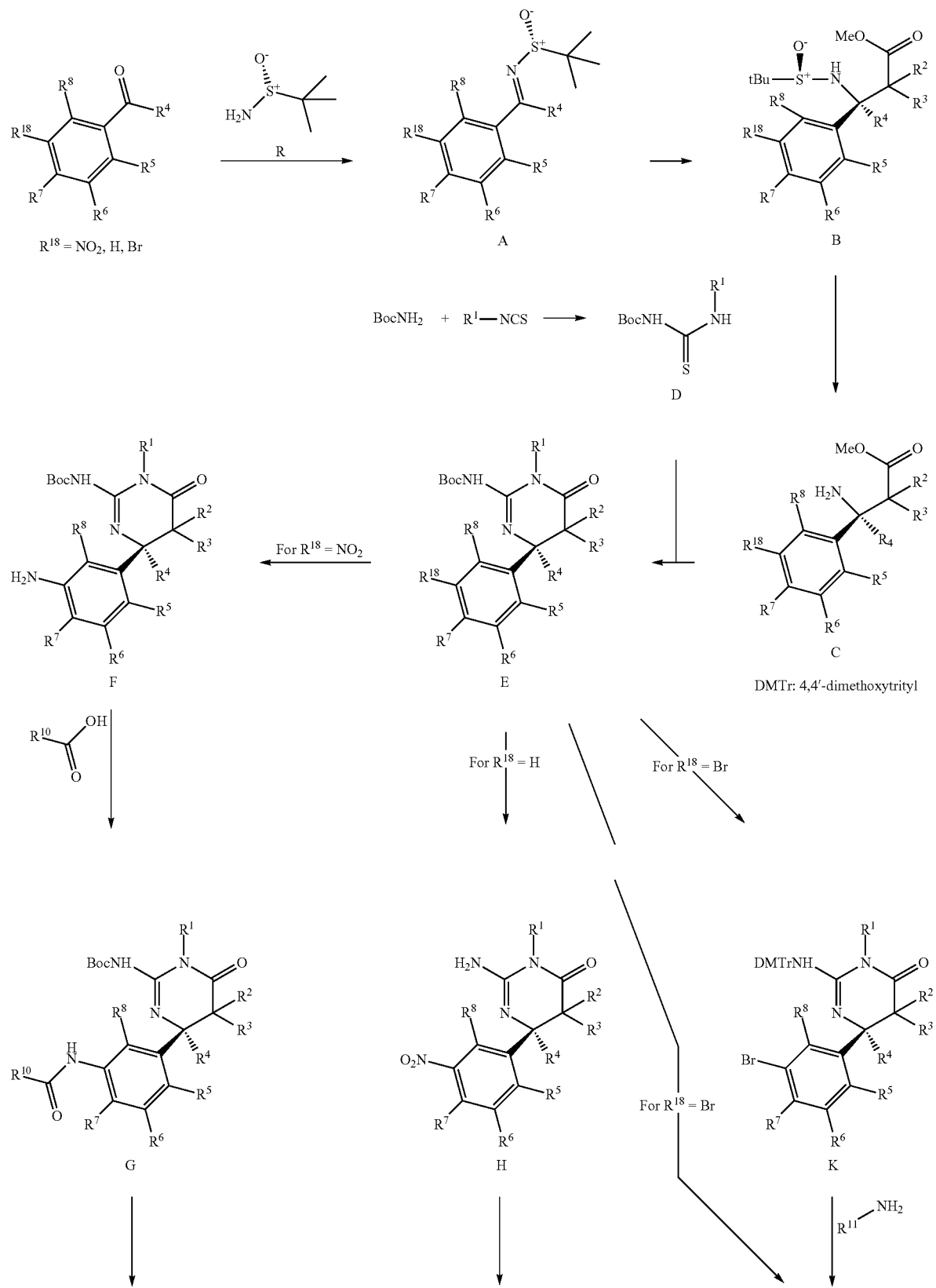

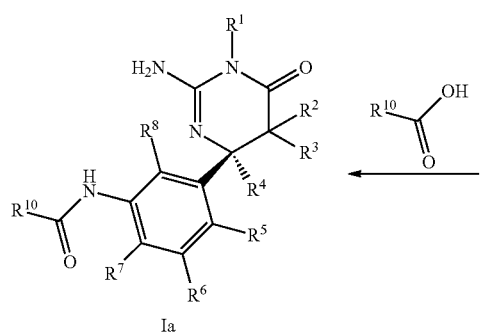 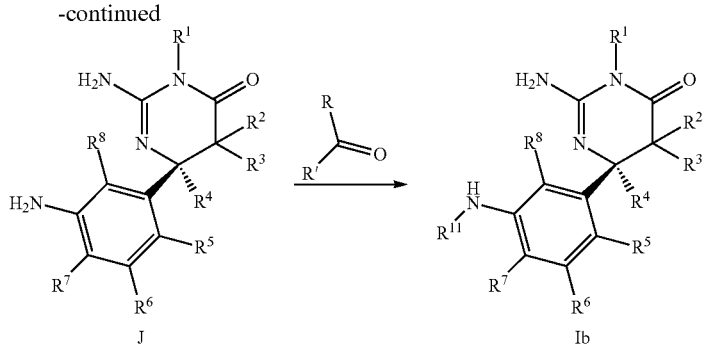

Ia J Ib

Hydrolysis of the chiral directing group in the sulfinamide ester B to give the amino ester C can be accomplished with a mineral acid, e.g. sulfuric acid or preferably hydrochloric acid in a solvent such as an ether, e.g. diethyl ether or more preferably 1,4-dioxane.

Thioureas D can be prepared by the deprotonation of tert-butylcarbamate with an alkali hydride, preferably sodium hydride followed by the reaction with an alkyl isothiacyanate in a solvent such as an ether, e.g. diethyl ether or more preferably THF.

The reaction of the amino ester C and the thiourea D to give the aminodihydropyrimidinone E can be effected with a carbodiimide, e.g. DCC or more preferably EDCI and an alkylamine, e.g. TEA or more preferably DIEA, in a solvent such as an alkyl formamide, preferably DMF.

The reduction of the nitro group in the aminodihydropyrimidinone E ($R^{18}$=NO2) to the aniline F can be accomplished by hydrogenation using a catalyst such as Pd/C in protic solvents, such as alcohols, preferably ethanol or methanol.

Coupling of the aniline F and a carboxylic acid to give the amide G can be effected with carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI) or O-(benzotriazol-1-yl)-N,N,N',N'-tetramethyluronium tetrafluoroborate (TBTU), preferably 1-[bis(dimethylamino)methylene]-1H-1,2,3-triazolo[4,5-b]pyridinium-3-oxide hexafluorophosphate (HATU) and an alkylamine, e.g. triethylamine or more preferably diisopropylethylamine in a solvent such as an alkyl formamide, preferably dimethlyformamide. Deprotection of the tert-butyloxycarbonyl group in G to give the final amide Ia is effected with a mineral acid, e.g. sulfuric acid or preferably hydrochloric acid in a solvent such as an ether, e.g. diethyl ether or more preferably 1,4-dioxane or in neat trifluoroacetic acid.

The nitration of the aminodihydropyrimidinone E ($R^{18}$=H) to give the intermediate H follows a standard procedure involving neat sulfuric acid and fuming nitric acid without using a solvent.

The reduction of the nitro group in the intermediate H to give the diamine I can be accomplished by hydrogenation using a catalyst such as Pd/C in protic solvents, such as alcohols, preferably ethanol or methanol.

Coupling of the diamine I and a carboxylic acid to give the amide Ia was best accomplished with DMTMM in a protic solvent such as an alcohol, preferably methanol.

The reductive amination of the aniline I and an aldehyde or ketone to give the final aniline Ib can be accomplished with a borohydride, e.g. sodium borohydride or sodium cyanoborohydride or preferably sodium triacetoxyborohydride or decaborane in the presence of an acid, e.g. a carbonic acid, preferably acetic acid in a solvent such as THF or preferably dichloroethane.

Exchange of the Boc-protecting group in E ($R^{18}$=Br) for the dimethoxytrityl protecting group K can be accomplished by a two step procedure involving the deprotection of the Boc-protecting group with a mineral acid, e.g. hydrochloric acid or a carbonic acid, preferrably trifluoro acetic acid followed by reprotection with a trityl chloride, preferrably 4,4'-dimethoxytrityl chloride and a base, e.g. an alkyl amine, preferably triethyl amine.

Coupling of the bromide K and an amine to give the final aniline Ib can be accomplished with a catalyst, e.g. Pd(OAc)$_2$, or preferably Pd$_2$(dba)$_3$ and a ligand, e.g. 2-dicyclohexylphosphino-2',4',6'-triisopropylbiphenyl (XPhos), 4,5-bis(diphenylphosphino)-9,9-dimethylxanthene (Xantphos), rac-2,2'-bis(diphenylphosphino)-1,1'-binaphthyl (BINAP), preferably 2-di-tert-butylphosphino-2',4',6'-triisopropylbiphenyl (tBuXphos) or 2-dicyclohexylphosphino-2'-(N,N-dimethylamino)biphenyl (Davephos) in the presence of a base, e.g. Cs$_2$CO$_3$, K$_2$CO$_3$, K$_3$PO$_4$ or NaOPh, preferrably t-BuONa and a solvent, e.g. 1,4-dioxane, dimethoxyethane, tBuOH or preferrably toluene.

In a further aspect, the present invention relates to a compound of formula I, as defined herein before, for use as therapeutically active substance or medicament.

The present invention relates to a compound of formula I for use as inhibitor of BACE2 activity. Thus, the invention is concerned with compounds of formula I, as defined in any of the paragraphs before, for the use in inhibition of BACE2 activity. In another aspect, the invention refers to compounds of formula I, as defined in any of the paragraphs before, for the use in inhibition of BACE2 activity. In yet another aspect, the invention relates to compounds of formula I, as defined in any of the paragraphs before, for the use in inhibition of BACE2 activity.

As described herein before, the compounds of formula I of the present invention can be used for the therapeutic and/or prophylactic treatment of diseases which can be ameliorated with the inhibition of BACE2 activity. As defined below, such diseases include diseases and disorders such as diabetes, particularly type 2 diabetes, and other metabolic disorders. The use for the therapeutic and/or prophylactic treatment of type 2 diabetes is of particular interest.

In another aspect of the invention, the compounds of formula I of the present invention can be used for the therapeutic and/or prophylactic treatment of diseases which can be ameliorated with the inhibition of BACE2 activity.

As described herein before, the compounds of formula I of the invention will be useful in preserving and restoring beta-cell function and stimulating insulin secretion in diabetic patients and in non-diabetic patients who have impaired glucose tolerance or who are in a pre-diabetic condition. They may be useful in treating type 1 diabetes or in delaying or preventing a patient with type 2 diabetes from needing insulin therapy. The compounds of formula I are further useful to ameliorate hyperinsulinemia, which often occurs in diabetic or pre-diabetic patients and in reducing the risks associated with metabolic syndrome, they may also be useful in treating vascular diseases such as hypertension.

Thus, the expression 'diseases which can be ameliorated with the inhibition of BACE2 activity' means diseases such as metabolic and cardiovascular diseases, in particular diabetes, more particularly type 2 diabetes, gestational diabetes, impaired fasting glucose, impaired glucose tolerance, insulin resistance, pre-diabetes, metabolic syndrome, diabetes type 1, complications of diabetes including diabetic nephropathy, diabetic retinopathy and diabetic neuropathy, chronic kidney disease, dyslipidemia, atherosclerosis, myocardial infarction, hypertension and further metabolic and cardiovascular disorders.

In particular, the expression 'diseases which can be ameliorated with the inhibition of BACE2 activity' relates to diabetes, particularly type 2 diabetes, impaired glucose tolerance, pre-diabetes, metabolic syndrome and hypertension. More particularly, the expression 'diseases which are associated with the inhibition of BACE2 activity' relates to diabetes, particularly type 2 diabetes.

In particular, the present invention relates to a compound of formula I, as defined in any of the paragraphs before, for the use as therapeutically active substance for the therapeutic and/or prophylactic treatment of type 2 diabetes.

The invention also relates to pharmaceutical compositions comprising a compound of formula I as defined above as an active ingredient and a pharmaceutically acceptable carrier and/or a pharmaceutically acceptable auxiliary substance. More specifically, the invention relates to pharmaceutical compositions comprising a compound of formula I useful for the therapeutic and/or prophylactic treatment of diseases which can be ameliorated with the inhibition of BACE2 activity.

The invention further relates to the use of a compound of formula I as defined herein before for the manufacture of a medicament for the therapeutic and/or prophylactic treatment of diseases which can be ameliorated with the inhibition of BACE2 activity, in particular for the therapeutic and/or prophylactic treatment of diseases and disorders such as diabetes, particularly type 2 diabetes, and other metabolic disorders.

In another aspect, the invention is concerned with the use of a compound of formula I for the manufacture of a medicament for the therapeutic and/or prophylactic treatment of diseases which can be ameliorated with the inhibition of BACE2 activity. In particular, the invention relates to use of a compound of formula I for the manufacture of a medicament for the therapeutic and/or prophylactic treatment of diabetes, particularly type 2 diabetes.

In another aspect, the invention relates to a method for the therapeutic and/or prophylactic treatment of diseases which can be ameliorated with the inhibition of BACE2 activity, which method comprises administering a therapeutically active amount of a compound of formula I to a human being or animal. In particular, such method relates to the therapeutic and/or prophylactic treatment of diseases and disorders such as diabetes, particularly type 2 diabetes, and other metabolic disorders.

The invention further relates to the use of compounds of formula I as defined above for the therapeutic and/or prophylactic treatment of diseases which can be ameliorated with the inhibition of BACE2 activity.

Pharmacological Tests

The compounds of formula I and their pharmaceutically acceptable salts possess valuable pharmacological properties. It has been found that the compounds of the present invention are associated with inhibition of BACE2 activity. The inhibition of BACE2 activity has also been measured in accordance with the test given hereinafter.

a) Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

b) Fluorescent-Peptide Cleavage Assay for BACE2 Inhibition

BACE2 enzyme ectodomain (derived from plasmid "pET17b-T7-hu proBACE2") was prepared as described in Ostermann et al., "Crystal Structure of Human BACE2 in Complex with a Hydroxyethylamine Transition-state Inhibitor", Journal of Molecular Biology 2006, 355, 249-261. The pro-enzyme was stored at 4° C. at a concentration of 70 µg/ml.

A fluorescent peptide with the amino acid sequence WS EVNLD AEFRC-MR121 was synthesised and a stock solution of 1.5 mM in DMSO prepared and stored at −20° C. MR121 is a fluorophore with an excitation wavelength of 630 nm and emission wavelength of 695 nm. The MR121 fluorescence is quenched by the N-terminal tryptophan until the peptide is cleaved by BACE2.

Assays were all made in a Corning 384-well black polystyrene non-binding surface microtitre plate with clear flat bottom and using a Plate:Vision (Perkin Elmer) fluorescence reader. To perform the assay an 80 nM solution of BACE2 was prepared in assay buffer (assay buffer is 100 mM Na-acetate; 20 mM EDTA; 0.05% BSA; pH 4.5) and incubated at room temperature for 1 hour to activate the enzyme. 39 µl of the activated BACE2 was placed in each assay well, followed by 1 µl compound to be tested at an appropriate concentration in 100% DMSO. The plate was then mixed and incubated for 10 minutes at room temperature. To start the assay, 10 µl of a 1.5 µM solution fluorescent peptide in assay buffer was added and the fluorescence intensity in the assay mixture measured at 695 nm with an excitation wavelength of 630 nm for 30 minutes.

The assay readout is the rate of change of fluorescence intensity giving a relative measure of BACE2 activity. Small values correspond to high inhibition and larger values to low inhibition. To determine $IC_{50}$ values (i.e. the concentration inhibiting the enzyme activity by 50%) of the compound for BACE2, typically, 15 assays were made with a range of concentrations chosen empirically to give low, high and intermediate inhibition of the protease. $IC_{50}$ values were determined using these assay values generated for a range of inhibitor concentrations and the curve fitting software XLfit (IDBS) using the Sigmoidal Dose-Response Model.

The preferred compounds according to formula I have an inhibitory activity in the above assay ($IC_{50}$) preferably of 1 nM to 50 µM, more preferably of 1 nM to 1 µM.

For example, the following compounds showed the following $IC_{50}$ values in the assays described above under a) and b), respectively:

| Example | $IC_{50}$ [µM] |
| --- | --- |
| 1 | 0.057[a] |
| 2 | 0.082[a] |
| 3 | 0.011[a] |
| 4 | 0.085[a] |
| 5 | 0.011[a] |
| 6 | 0.350[a] |
| 7 | 1.010[a] |
| 8 | 0.009[a] |
| 9 | 0.025[a] |
| 10 | 0.002[a] |
| 11 | 0.014[a] |
| 12 | 0.023[a] |
| 13 | 0.190[a] |
| 14 | 0.120[a] |
| 15 | 0.007[a] |
| 16 | 0.009[a] |
| 17 | 0.360[a] |
| 18 | 0.023[a] |
| 19 | 0.074[a] |
| 20 | 0.066[a] |
| 21 | 0.014[a] |
| 22 | 0.005[a] |
| 23 | 0.007[a] |
| 24 | 0.039[a] |
| 25 | 0.004[a] |
| 26 | 0.274[a] |
| 27 | 0.157[a] |
| 28 | 0.043[a] |
| 29 | 0.032[a] |
| 30 | 0.033[a] |
| 31 | 0.037[a] |
| 32 | 0.032[a] |
| 33 | 0.029[a] |
| 34 | 0.008[a] |
| 35 | 0.084[a] |
| 36 | 0.535[a] |
| 37 | 0.039[a] |
| 38 | 0.048[a] |

-continued

| Example | $IC_{50}$ [µM] |
| --- | --- |
| 39 | 0.234[a] |
| 40 | 0.021[a] |
| 41 | 0.426[a] |
| 42 | 0.211[a] |
| 43 | 0.211[a] |
| 44 | 0.045[a] |
| 45 | 0.011[a] |
| 46 | 0.109[a] |
| 47 | 0.217[a] |
| 48 | 0.042[a] |
| 49 | 0.321[a] |
| 50 | 0.0218[a] |
| 51 | 0.073[a] |
| 52 | 0.007[a] |
| 53 | 0.153[a] |
| 54 | 0.076[a] |
| 55 | 0.115[a] |
| 56 | 0.015[a] |
| 57 | — |
| 58 | 0.01[a]3 |
| 59 | — |
| 60 | — |
| 61 | 0.059[a] |
| 62 | 0.001[a] |
| 63 | 0.021[a] |
| 64 | — |
| 65 | — |
| 66 | — |
| 67 | — |
| 68 | 0.003[a] |
| 69 | — |
| 70 | 0.016[a] |
| 71 | 0.014[a] |
| 72 | 0.201[a] |
| 73 | 0.135[a] |
| 74 | 0.076[a] |
| 75 | 0.012[a] |
| 76 | 0.015[a] |
| 77 | — |
| 78 | 0.156[a] |
| 79 | 0.044[a] |
| 80 | 0.044[a] |
| 81 | 0.223[a] |
| 82 | 0.135[a] |
| 83 | 0.012[a] |
| 84 | 0.069[a] |
| 85 | 0.101[a] |
| 86 | 0.236[a] |
| 87 | 0.119[a] |
| 88 | 0.795[a] |
| 89 | 1.140[a] |
| 90 | 0.467[a] |
| 91 | 0.322[a] |
| 92 | 0.279[a] |
| 93 | 0.025[a] |
| 94 | 0.704[a] |
| 95 | 0.406[a] |
| 96 | 0.001[a] |
| 97 | 0.242[a] |
| 98 | 0.057[a] |
| 99 | 0.006[a] |
| 100 | 0.001[a] |
| 101 | 0.001[a] |
| 102 | 0.217[a] |
| 103 | 0.001[a] |
| 104 | 0.004[a] |
| 105 | 0.012[a] |
| 106 | 0.002[a] |
| 107 | 0.002[a] |
| 108 | 0.178[a] |
| 109 | 0.045[a] |
| 110 | 0.391[a] |
| 111 | 0.046[a] |
| 112 | — |
| 113 | 0.036[a] |
| 114 | — |
| 115 | 0.977[a] |

-continued

| Example | IC$_{50}$ [μM] |
|---|---|
| 116 | 2.160$^{a)}$ |
| 117 | 0.226$^{a)}$ |
| 118 | 0.002$^{a)}$ |
| 119 | 0.016$^{a)}$ |
| 120 | — |
| 121 | 0.009$^{a)}$ |
| 122 | — |
| 123 | 0.046$^{a)}$ |
| 124 | 0.589$^{a)}$ |
| 125 | 0.028$^{a)}$ |
| 126 | 0.026$^{a)}$ |
| 127 | 0.073$^{a)}$ |
| 128 | — |
| 129 | 3.050$^{a)}$ |
| 130 | — |
| 131 | 0.256$^{a)}$ |
| 132 | 0.054$^{a)}$ |
| 133 | 0.041$^{a)}$ |
| 134 | 0.734$^{a)}$ |
| 135 | 0.001$^{a)}$ |
| 136 | 2.000$^{a)}$ |
| 137 | 0.124$^{a)}$ |
| 138 | 0.500$^{a)}$ |
| 139 | 0.031$^{a)}$ |
| 140 | 0.047$^{a)}$ |
| 141 | 0.332$^{a)}$ |
| 142 | 0.089$^{a)}$ |
| 143 | 0.044$^{a)}$ |
| 144 | 0.003$^{a)}$ |
| 145 | 0.014$^{a)}$ |
| 146 | 0.257$^{a)}$ |
| 147 | 0.269$^{a)}$ |
| 148 | 0.497$^{a)}$ |
| 149 | 0.081$^{a)}$ |
| 150 | 0.021$^{b)}$ |
| 151 | 0.100$^{b)}$ |
| 152 | 0.002$^{a)}$ |
| 153 | 0.130$^{b)}$ |
| 154 | 0.035$^{b)}$ |
| 155 | 0.123$^{a)}$ |
| 156 | 1.206$^{a)}$ |
| 157 | 0.654$^{a)}$ |
| 158 | 0.298$^{a)}$ |
| 159 | 0.024$^{a)}$ |
| 160 | 0.006$^{a)}$ |
| 161 | 0.013$^{b)}$ |
| 162 | 0.120$^{b)}$ |
| 163 | 0.062$^{b)}$ |
| 164 | 1.090$^{b)}$ |
| 165 | 0.039$^{b)}$ |
| 166 | 0.080$^{b)}$ |
| 167 | 0.073$^{b)}$ |
| 168 | 0.014$^{b)}$ |
| 169 | 0.180$^{b)}$ |
| 170 | 0.140$^{b)}$ |
| 171 | 1.800$^{b)}$ |
| 172 | 0.110$^{b)}$ |
| 173 | 0.400$^{b)}$ |
| 174 | 0.150$^{b)}$ |
| 175 | 0.250$^{b)}$ |
| 176 | 0.130$^{b)}$ |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day, especially from about 1 to 500 mg per day, of a compound of formula I or of the corresponding amount of a pharmaceutically acceptable salt thereof. Depending on severity of the disease and the precise pharmacokinetic profile of the compound, the daily dosage may be administered as single dose or in divided doses and, in addition, the upper limit can also be exceeded when this is found to be indicated.

The following examples illustrate the present invention without limiting it, but serve merely as representative thereof. Examples of compositions according to the invention are:

Example A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure:
1. Mix ingredients 1, 2, 3 and 4 and granulate with purified water.
2. Dry the granules at 50° C.

3. Pass the granules through suitable milling equipment.
4. Add ingredient 5 and mix for three minutes; compress on a suitable press.

Example B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure:
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc is added thereto and mixed thoroughly. The mixture is filled by machine into suitable capsules, e.g. hard gelatin capsules.

Example B-2

Soft Gelatin Capsules of the following composition are manufactured:

TABLE 3 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule | |
|---|---|---|
| Gelatin | 75 | |
| Glycerol 85% | 32 | |
| Karion 83 | 8 | (dry matter) |
| Titan dioxide | 0.4 | |
| Iron oxide yellow | 1.1 | |
| Total | 116.5 | |

Manufacturing Procedure
The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 5 possible suppository composition

| ingredient | mg/supp. |
|---|---|
| Compound of formula I | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

Example D

Injection solutions of the following composition are manufactured:

TABLE 6 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure
The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 7 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidone K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Abbreviations:

Boc=tert-butoxycarbonyl, DCC=N,N'-diisopropyl-carbodiimide, DIEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, tBU=tert-butyl, TEA=triethylamine, and THF=tetrahydrofuran.

The following examples are provided for illustration of the invention. They should not be considered as limiting the scope of the invention, but merely as being representative thereof.

Synthesis of the Intermediate Sulfinyl Imines A

General Procedure

To a solution of the (R)-(+)-tert-butylsulfinamide (66 mmole) in THF (350 ml) was added subsequently the ketone (72.6 mmole) and titanium(IV) ethoxide (132 mmole) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and evaporated. The residue was chromatographed on silica using cyclohexane/ethyl acetate (2:1) to give the pure sulfinyl imine A.

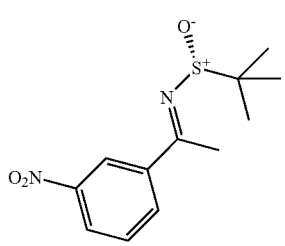

Intermediate A1

Starting from 1-(3-nitro-phenyl)-ethanone, the product (R)-2-methyl-propane-2-sulfinic acid [1-(3-nitro-phenyl)-(E)-ethylidene]-amide was obtained as a pale yellow solid. MS (ESI): m/z=269.2 [M+H]$^+$.

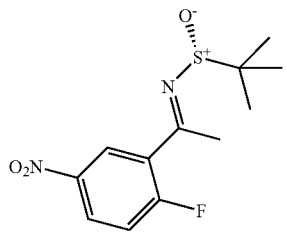

Intermediate A2

Starting from 1-(2-fluoro-5-nitro-phenyl)-ethanone, the product (R)-2-methyl-propane-2-sulfinic acid [1-(2-fluoro-5-nitro-phenyl)-(E)-ethylidene]-amide was obtained as a pale yellow solid. MS (ESI): m/z=287.0 [M+H]$^+$.

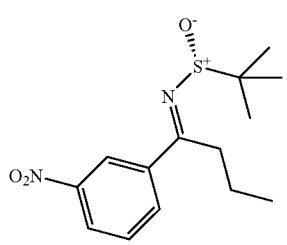

Intermediate A3

Starting from 1-(5-nitro-phenyl)-butanone, the product (R)-2-methyl-propane-2-sulfinic acid [1-(5-nitro-phenyl)-(E)-butylidene]-amide was obtained as a yellow oil. MS (ESI): m/z=297.4 [M+H]$^+$.

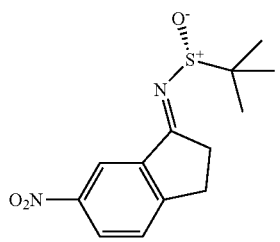

Intermediate A4

Starting from 6-nitro-indan-1-one, the product 2-methyl-propane-2-sulfinic acid [6-nitro-indan-(1E)-ylidene]-amide was obtained as a black solid. MS (ESI): m/z=280.1 [M]$^+$.

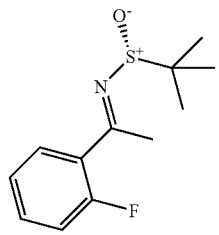

Intermediate A5

Starting from 1-(2-fluoro-phenyl)-ethanone, the product (R)-2-methyl-propane-2-sulfinic acid [1-(2-fluoro-phenyl)-(E)-ethylidene]-amide was obtained as a pale red liquid. MS (ESI): m/z=242.1 [M+H]$^+$.

Intermediate A6

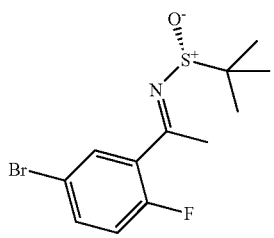

Starting from 1-(5-bromo-2-fluoro-phenyl)-ethanone, the product (R)-2-methyl-propane-2-sulfinic acid [1-(5-bromo-2-fluoro-phenyl)-(E)-ethylidene]-amide was obtained as a yellow solid. MS (ESI): m/z=320.0 and 322.0 [M+H]$^+$.

Synthesis of the Intermediate Sulfinamide Esters B

General Procedure

To a solution of diisopropylamide (21.9 ml) in THF (250 ml) was added at −78° C. n-butyllithium (1.6 M solution in hexane, 97.2 ml) and stirring was continued at −78° C. for 30 min. The solution was treated with methyl acetate (12.4 ml) and after 30 min a solution of chlorotriisopropoxytitanium (43.0 g) in THF (50 ml) was added and stirring was continued at −78° C. for 30 min. The mixture was treated with a solution of the sulfinyl imine A (47.1 mmole) in THF (25 ml) and stirring was continued at −78° C. for 3 h. The mixture was quenched with saturated aqueous NH$_4$Cl solution (300 ml) and the mixture was filtered over dicalite. The layers were separated, the aqueous layer was extracted with ethyl acetate, the combined organic layers were washed with water, dried and evaporated. The residue was chromatographed on silica using cyclohexane/ethyl acetate (1:2) to give the pure sulfinamide ester B.

Intermediate B1

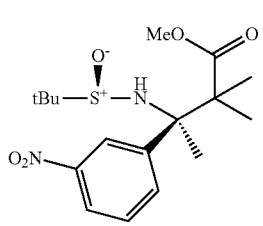

Starting from (R)-2-methyl-propane-2-sulfinic acid [1-(3-nitro-phenyl)-(E)-ethylidene]-amide and isobutyric acid methyl ester, the product (R)-3-(5-nitro-phenyl)-2,2-dimethyl-3-((R)-2-methyl-propane-2-sulfinylamino)-butyric acid methyl ester was obtained as a pale yellow solid. MS (ESI): m/z=371.3 [M+H]$^+$.

Intermediate B2

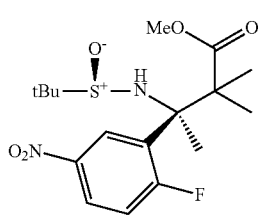

Starting from (R)-2-methyl-propane-2-sulfinic acid [1-(2-fluoro-5-nitro-phenyl)-(E)-ethylidene]-amide and isobutyric acid methyl ester, the product (S)-3-(2-fluoro-5-nitro-phenyl)-2,2-dimethyl-3-((R)-2-methyl-propane-2-sulfinylamino)-butyric acid methyl ester was obtained as a pale yellow oil. MS (ESI): m/z=389.3 [M+H]$^+$.

Intermediate B3

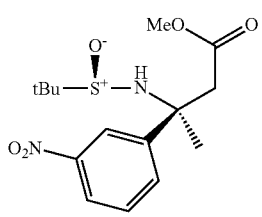

Starting from (R)-2-methyl-propane-2-sulfinic acid [1-(3-nitro-phenyl)-(E)-ethylidene]-amide and methyl acetate, the product (S)-3-(R)-2-methyl-propane-2-sulfinylamino)-3-(3-nitro-phenyl)-butyric acid methyl ester was obtained as a pale yellow oil. MS (ESI): m/z=343.1 [M+H]$^+$.

Intermediate B4

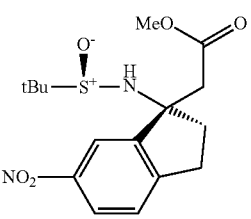

Starting from (R)-2-methyl-propane-2-sulfinic acid [1-(5-nitro-phenyl)-(E)-butylidene]-amide and methyl acetate, the product (S)-3-(R)-2-methyl-propane-2-sulfinylamino)-3-(3-nitro-phenyl)-hexanoic acid methyl ester was obtained as a white solid. MS (ESI): m/z=371.4 [M+H]$^+$.

Intermediate B5

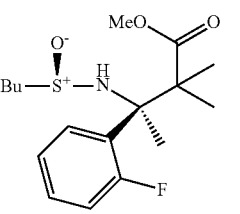

Starting from 2-methyl-propane-2-sulfinic acid [6-nitro-indan-(1E)-ylidene]-amide and methyl acetate, the product [(S)-1-((R)-2-methyl-propane-2-sulfinylamino)-6-nitro-indan-1-yl]-acetic acid methyl ester was obtained as a black oil. MS (ESI): m/z=355.5 [M+H]$^+$.

Intermediate B6

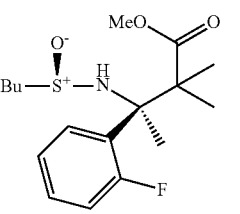

Starting from (R)-2-methyl-propane-2-sulfinic acid [1-(2-fluoro-phenyl)-(E)-ethylidene]-amide and isobutyric acid methyl ester, the product (S)-methyl 3-((S)-1,1-dimethylethylsulfinamido)-3-(2-fluorophenyl)-2,2-dimethylbutanoate was obtained as a pale yellow oil. MS (ESI): m/z=344.1 [M+H]⁺.

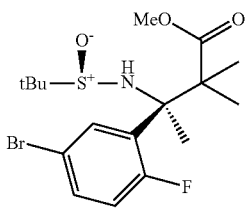

Intermediate B7

Starting from (R)-2-methyl-propane-2-sulfinic acid [1-(5-bromo-2-fluoro-phenyl)-(E)-ethylidene]-amide and isobutyric acid methyl ester, the product (S)-methyl 3-((S)-1,1-dimethylethylsulfinamido)-3-(5-bromo-2-fluoro-phenyl)-2,2-dimethylbutanoate was obtained as a pale yellow oil. MS (ESI): m/z=422.1 and 424.1 [M+H]⁺.

Synthesis of the Intermediate Amino Esters C
General Procedure

A solution of the sulfinamide ester B (42.2 mmole) in methanol (400 ml) was treated with a solution of HCl in 1,4-dioxane (4 M, 530 ml) and stirring was continued at 22° C. for 2 h. The mixture was evaporated and the residue was partitioned between dichloromethane and 1 M aqueous hydrochloric acid. The aqueous layer was separated, diluted with saturated aqueous Na₂CO₃ until the pH was ca. 10 and extracted with dichloromethane. The organic layer was dried and evaporated to give the pure aminoester C.

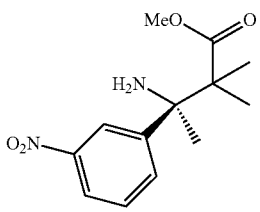

Intermediate C1

Starting from (R)-3-(5-nitro-phenyl)-2,2-dimethyl-3-((R)-2-methyl-propane-2-sulfinylamino)-butyric acid methyl ester, the product (R)-3-amino-2,2-dimethyl-3-(3-nitro-phenyl)-butyric acid methyl ester was obtained as a pale brown oil. MS (ESI): m/z=267.2 [M+H]⁺.

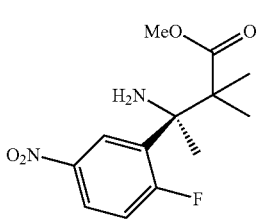

Intermediate C2

Starting from (S)-3-(2-fluoro-5-nitro-phenyl)-2,2-dimethyl-3-((R)-2-methyl-propane-2-sulfinylamino)-butyric acid methyl ester, the product (S)-3-amino-3-(2-fluoro-5-nitro-phenyl)-2,2-dimethyl-butyric acid methyl ester was obtained as a pale yellow oil. MS (ESI): m/z=285.3 [M+H]⁺.

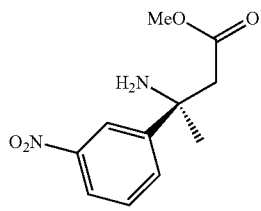

Intermediate C3

Starting from (S)-3-((R)-2-methyl-propane-2-sulfinylamino)-3-(3-nitro-phenyl)-butyric acid methyl ester, the product (S)-3-amino-3-(3-nitro-phenyl)-butyric acid methyl ester was obtained as a colourless oil. MS (ESI): m/z=239.1 [M+H]⁺.

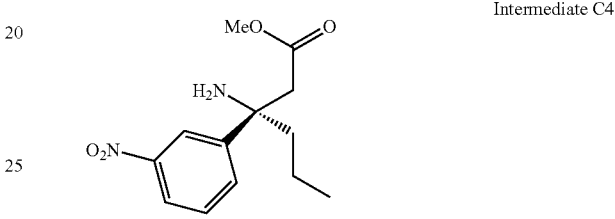

Intermediate C4

Starting from (S)-3-((R)-2-methyl-propane-2-sulfinylamino)-3-(3-nitro-phenyl)-hexanoic acid methyl ester, the product (S)-3-amino-3-(3-nitro-phenyl)-hexanoic acid methyl ester was obtained as a colourless oil. MS (ESI): m/z=267.3 [M+H]⁺.

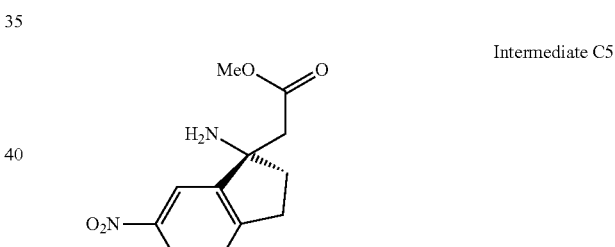

Intermediate C5

Starting from [(S)-1-((R)-2-methyl-propane-2-sulfinylamino)-6-nitro-indan-1-yl]-acetic acid methyl ester, the product ((S)-1-amino-6-nitro-indan-1-yl)-acetic acid methyl ester was obtained as a black oil. MS (ESI): m/z=251.2 [M+H]⁺.

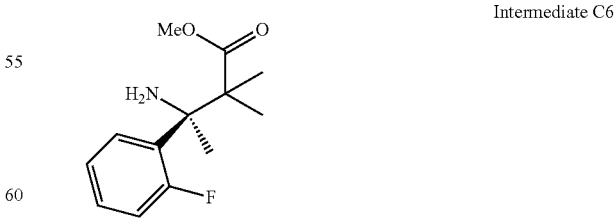

Intermediate C6

Starting from (S)-methyl 3-((S)-1,1-dimethylethylsulfinamido)-3-(2-fluorophenyl)-2,2-dimethylbutanoate, the product (S)-3-amino-3-(2-fluoro-phenyl)-2,2-dimethyl-butyric acid methyl ester was obtained as a colorless oil. MS (ESI): m/z=240.2 [M+H]⁺.

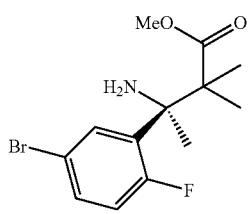

Intermediate C7

Starting from (S)-methyl 3-((S)-1,1-dimethylethylsulfinamido)-3-(5-bromo-2-fluoro-phenyl)-2,2-dimethylbutanoate, the product (S)-3-amino-3-(5-bromo-2-fluoro-phenyl)-2,2-dimethyl-butyric acid methyl ester was obtained as a pale yellow oil. MS (ESI): m/z=318.0 and 320.0 [M+H]⁺.

Synthesis of the Intermediate Thioureas D

General Procedure

To a solution of tert-butylcarbamate (5 mmole) in THF (5.0 ml) was added at 22° C. NaH (60% in oil, 5 mmole) in several portions and stirring was continued at 22° C. for 15 min until gas evolution ceased. The mixture was treated with a solution of the isothiacyanate (5.0 mmole) in THF (5.0 ml) and stirring was continued at 22° C. for 15 min. The mixture was poured into ice-water, extracted with diethylether, the organic layer was washed with water, dried, evaporated and the residue was chromatographed on silica using n-heptane/ethyl acetate or triturated with pentane to give the thiourea D.

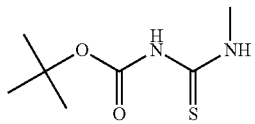

Intermediate D1

Starting from isothiocyanatomethane, the product tert-butyl [(methylamino) carbonothioyl]-carbamate was obtained as a colorless solid. MS (ESI): m/z=191.4 [M+H]⁺.

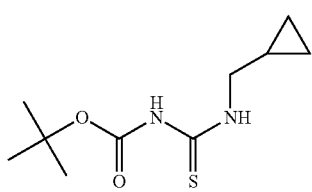

Intermediate D2

Starting from isothiocyanatomethyl-cyclopropane, the product tert-butyl [(cyclopropylmethyl-amino)carbonothioyl]carbamate was obtained as a white solid. MS (ESI): m/z=231.3 [M+H]⁺.

Synthesis of the Intermediate Aminodihydropyrimidinones E

General Procedure

To a solution of the amino ester C (21 mmole) in DMF (50 ml) was added subsequently the thiourea D (23.1 mmole), DIEA (84 mmole) and EDCI (29.4 mmole) and the mixture was stirred at 22° C. for 16 h. The mixture was partitioned between water and ethyl acetate, the organic layer was dried, evaporated and the residue was chromatographed on silica using cyclohexane/ethyl acetate (2:1) to give the pure aminodihydropyrimidinone E.

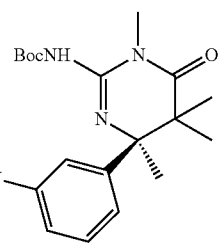

Intermediate E1

Starting from (R)-3-amino-2,2-dimethyl-3-(3-nitro-phenyl)-butyric acid methyl ester and tert-butyl [(methylamino)carbonothioyl]carbamate, the product [(R)-1,4,5,5-tetramethyl-4-(3-nitro-phenyl)-6-oxo-1,4,5,6-tetrahydro-pyrimidin-2-yl]-carbamic acid tert-butyl ester was obtained as a white solid. MS (ESI): m/z=391.3 [M+H]⁺.

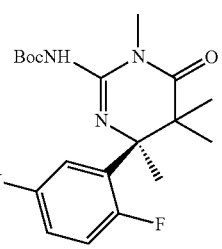

Intermediate E2

Starting from (S)-3-amino-3-(2-fluoro-5-nitro-phenyl)-2,2-dimethyl-butyric acid methyl ester and tert-butyl [(methylamino)carbonothioyl]carbamate, the product [(S)-4-(2-fluoro-5-nitro-phenyl)-1,4,5,5-tetramethyl-6-oxo-1,4,5,6-tetrahydro-pyrimidin-2-yl]-carbamic acid tert-butyl ester was obtained as pale yellow oil. MS (ESI): m/z=407.3 [M−H]⁻.

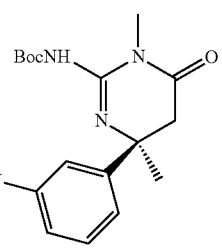

Intermediate E3

Starting from (S)-3-amino-3-(3-nitro-phenyl)-butyric acid methyl ester and tert-butyl [(methylamino)carbonothioyl]carbamate, the product [(S)-1,4-dimethyl-4-(3-nitro-phenyl)-6-oxo-1,4,5,6-tetrahydro-pyrimidin-2-yl]-carbamic acid tert-butyl ester was obtained as white solid. MS (ESI): m/z=361.4 [M−H]⁻.

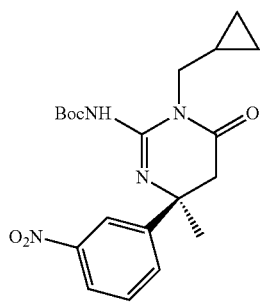

Intermediate E4

Starting from (S)-3-amino-3-(3-nitro-phenyl)-butyric acid methyl ester and tert-butyl [(c-cyclopropyl-methylamino)carbonothioyl]carbamate, the product [(S)-1-c-cyclopropyl-methyl-4-methyl-4-(3-nitro-phenyl)-6-oxo-1,4,5,6-tetrahydro-pyrimidin-2-yl]-carbamic acid tert-butyl ester was obtained as colorless oil solid. MS (ESI): m/z=401.3 [M−H]−.

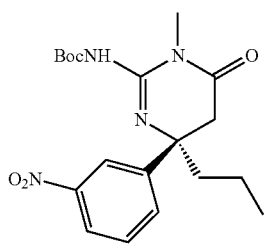

Intermediate E5

Starting from (S)-3-amino-3-(3-nitro-phenyl)-hexanoic acid methyl ester and tert-butyl [(methylamino)carbonothioyl]carbamate, the product [(S)-1-methyl-4-(3-nitro-phenyl)-6-oxo-4-propyl-1,4,5,6-tetrahydro-pyrimidin-2-yl]-carbamic acid tert-butyl ester was obtained as an amorphous solid. MS (ESI): m/z=389.3 [M−H]−.

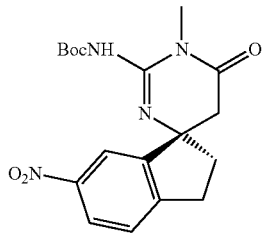

Intermediate E6

Starting from ((S)-1-amino-6-nitro-indan-1-yl)-acetic acid methyl ester and tert-butyl [(methylamino)carbonothioyl]carbamate, the product tert-butyl [(1S)-1'-methyl-6-nitro-6'-oxo-2,3,5',6'-tetrahydro-1'H-spiro[indene-1,4'-pyrimidin]-2'-yl]carbamate was obtained as pale brown solid. MS (ESI): m/z=373.1 [M−H]−.

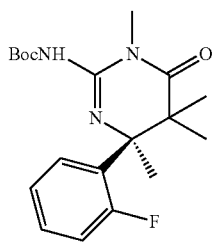

Intermediate E7

Starting from (S)-3-amino-3-(2-fluoro-phenyl)-2,2-dimethyl-butyric acid methyl ester and tert-butyl [(methylamino)carbonothioyl]carbamate, the product [(S)-4-(2-fluoro-phenyl)-1,4,5,5-tetramethyl-6-oxo-1,4,5,6-tetrahydro-pyrimidin-2-yl]-carbamic acid tert-butyl ester was obtained as a white solid. MS (ESI): m/z=364.2 [M+H]+.

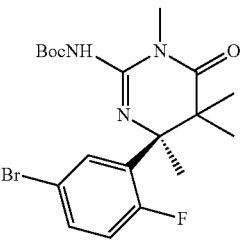

Intermediate E8

Starting from (S)-3-amino-3-(5-bromo-2-fluoro-phenyl)-2,2-dimethyl-butyric acid methyl ester and tert-butyl [(methylamino)carbonothioyl]carbamate, the product [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester was obtained as a white solid. MS (ESI): m/z=442.2 and 444.1 [M+H]+.

Synthesis of the Intermediate Anilines F
General Procedure

A suspension of the aminodihydropyrimidinone E (12.1 mmole) in ethylalcohol (100 ml) and Pd/C (10%, 400 mg) was hydrogenated at normal pressure and 22° C. for 2 h. The mixture was filtered, the filtrate evaporated and the residue was chromatographed on silica using cyclohexane/ethyl acetate (1:1) to give the pure aniline F.

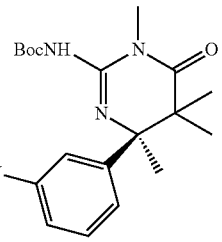

Intermediate F1

Starting from [(R)-1,4,5,5-tetramethyl-4-(3-nitro-phenyl)-6-oxo-1,4,5,6-tetrahydro-pyrimidin-2-yl]-carbamic acid tert-butyl ester, the product [(R)-4-(3-amino-phenyl)-1,4,5,5-tetramethyl-6-oxo-1,4,5,6-tetrahydro-pyrimidin-2-yl]-carbamic acid tert-butyl ester was obtained as a white solid. MS (ESI): m/z=359.2 [M−H]−.

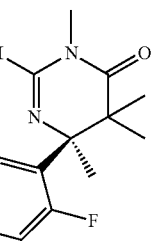

Intermediate F2

Starting from [(S)-4-(2-fluoro-5-nitro-phenyl)-1,4,5,5-tetramethyl-6-oxo-1,4,5,6-tetrahydro-pyrimidin-2-yl]-carbamic acid tert-butyl ester, the product [(S)-4-(5-amino-2-fluoro-phenyl)-1,4,5,5-tetramethyl-6-oxo-1,4,5,6-tetrahydro-pyrimidin-2-yl]-carbamic acid tert-butyl ester was obtained as a colorless oil. MS (ESI): m/z=379.3 [M+H]+.

Intermediate F3

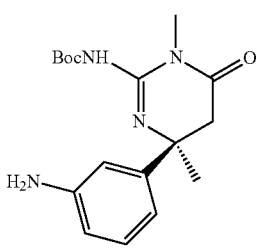

Starting from [(S)-1,4-dimethyl-4-(3-nitro-phenyl)-6-oxo-1,4,5,6-tetrahydro-pyrimidin-2-yl]-carbamic acid tert-butyl ester, the product [(S)-4-(3-amino-phenyl)-1,4-dimethyl-6-oxo-1,4,5,6-tetrahydro-pyrimidin-2-yl]-carbamic acid tert-butyl ester was obtained as a white amorphous solid. MS (ESI): m/z=331.4 [M−H]⁻.

Intermediate F4

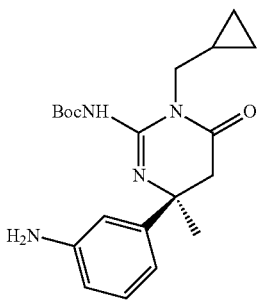

Starting from [(S)-1-c-cyclopropylmethyl-4-methyl-4-(3-nitro-phenyl)-6-oxo-1,4,5,6-tetrahydro-pyrimidin-2-yl]-carbamic acid tert-butyl ester, the product [(S)-4-(3-amino-phenyl)-1-c-cyclopropylmethyl-4-methyl-6-oxo-1,4,5,6-tetrahydro-pyrimidin-2-yl]-carbamic acid tert-butyl ester was obtained as a pale brown solid. MS (ESI): m/z=371.3 [M−H]⁻.

Intermediate F5

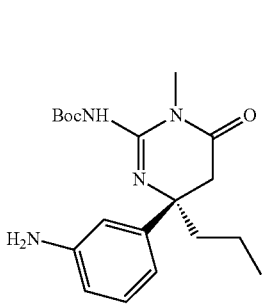

Starting from [(S)-1-methyl-4-(3-nitro-phenyl)-6-oxo-4-propyl-1,4,5,6-tetrahydro-pyrimidin-2-yl]-carbamic acid tert-butyl ester, the product [(S)-4-(3-amino-phenyl)-1-methyl-6-oxo-4-propyl-1,4,5,6-tetrahydro-pyrimidin-2-yl]-carbamic acid tert-butyl ester was obtained as a pale yellow foam. MS (ESI): m/z=361.3 [M+H]⁺.

Intermediate F6

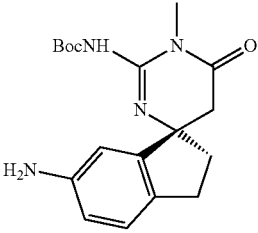

Starting from tert-butyl [(1S)-1'-methyl-6-nitro-6'-oxo-2,3,5',6'-tetrahydro-1'H-spiro[indene-1,4'-pyrimidin]-2'-yl] carbamate, the product tert-butyl [(1S)-6-amino-1'-methyl-6'-oxo-2,3,5',6'-tetrahydro-1'H-spiro[indene-1,4'-pyrimidin]-2'-yl]carbamate was obtained as a white amorphous solid. MS (ESI): m/z=343.1 [M−H]⁻.

Synthesis of the Final Product Ia Via the Intermediate G

General Procedure

To a solution of the aniline F (0.30 mmole) in DMF (2 ml) was added subsequently HATU (0.60 mmole), the carbonic acid (0.45 mmole) and DIEA (0.90 mmole) and stirring was continued at 22° C. for 16 h. The mixture was purified on prep. RP-18 HPLC using a gradient of acetonitrile and water (containing 0.1% of formic acid) to give the t-butyloxycarbonyl protected intermediate G.

The t-butyloxycarbonyl protected intermediate G was treated with a solution of CF₃COOH (1 ml) in dichloromethane (18 ml) and stirring was continued at 22° C. for 16 h. The mixture was evaporated and the residue was purified either by trituration with ethyl ether to give the pure amide Ia as the CF₃COOH salt.

Synthesis of the Final Product Ib Via Intermediates H and J

Intermediate H

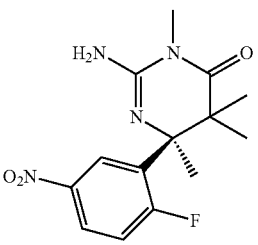

To a solution of [(S)-4-(2-fluoro-phenyl)-1,4,5,5-tetramethyl-6-oxo-1,4,5,6-tetrahydro-pyrimidin-2-yl]-carbamic acid tert-butyl ester (intermediate E7, 0.27 g) in sulfuric acid (98%, 3.1 ml) was added at 0° C. fuming nitric acid (0.05 ml) and the reaction mixture was allowed to warm to 22° over 30 min. The mixture was slowly added to 20 ml ice cold water, the pH was adjusted to 7 using aqueous 4N NaOH and extracted with ethyl acetate. The organic layer was washed with water, dried and evaporated to give crude (S)-2-amino-6-(2-fluoro-5-nitro-phenyl)-3,5,5,6-tetramethyl-5,6-dihydro-3H-pyrimidin-4-one (0.19 g) as a pale orange amorphous solid. MS (ESI): m/z=309.2 [M+H]⁺.

Intermediate J

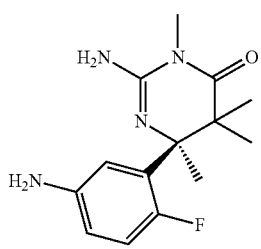

To a solution of (S)-2-amino-6-(2-fluoro-5-nitro-phenyl)-3,5,5,6-tetramethyl-5,6-dihydro-3H-pyrimidin-4-one (0.55 g) in ethanol (25 ml) and triethylamine (0.25 ml) was added Pd/C (10%, 80 mg) and the mixture was hydrogenated at atmospheric pressure for 3 h. The mixture was filtered, the filtrate evaporated and the residue purified by chromatography on silica using ethyl acetate/MeOH (1:1) to give (S)-2-amino-6-(5-amino-2-fluoro-phenyl)-3,5,5,6-tetramethyl-5,6-dihydro-3H-pyrimidin-4-one (0.49 g) as a pale yellow amorphous solid. MS (ESI): m/z=297.2 [M+H]$^+$.

General Procedure for the Conversion of Intermediate J to the Final Product Ib

To a solution of the aniline J (0.1 mmole) in dichloroethane (0.3 ml) was subsequently added at 22° C. the ketone (0.11 mmole) and acetic acid (0.2 mmole) and stirring of the mixture was continued for 1 h. Sodium triacetoxy borohydride (0.14 mmole) if not stated otherwise was added and stirring was continued for 2-16 h. The mixture was diluted with water, the organic layer was washed with saturated aqueous NaHCO$_3$, dried and evaporated. The crude material was chromatographed on NH$_2$-silica using dichloromethane to give the pure final product Ib. As an alternative to sodium triacetoxy borohydride, zinc-modified cyanoborohydride (suspension of sodium cyanoborohydride (0.14 mmole) and ZnCl$_2$ (0.07 mmole) in THF (0.2 ml)) was used. As an additional alternative to triacetoxy borohydride, decaborane (0.15 mmole) in MeOH (0.5 ml) was used at slightly elevated temperature (40° C.).

Synthesis of the Final Product Ia from Intermediate J
General Procedure

To a solution of the acid (0.12 mmole) in methanol (0.6 ml) was added at 0° C. 4-(4,6-dimethoxy-1,3,5-triazin-2-yl)-4-methyl-morpholinium chloride (0.12 mmole) and the solution was stirred for 60 min. The mixture was treated with the aniline I (0.12 mmole) and stirring was continued at 0° C. for 24 h. The mixture was evaporated and the residue partitioned between aqueous saturated Na$_2$CO$_3$ and ethyl acetate, the organic layer was dried and evaporated and the residue purified on prep. RP-18 HPLC using a gradient of acetonitrile and water (containing 0.1% of triethylamine) or NH$_2$-silica using ethyl acetate/n-heptane to give the pure final product Ia.

Synthesis of the Final Product Ib Via Intermediate K

Intermediate K

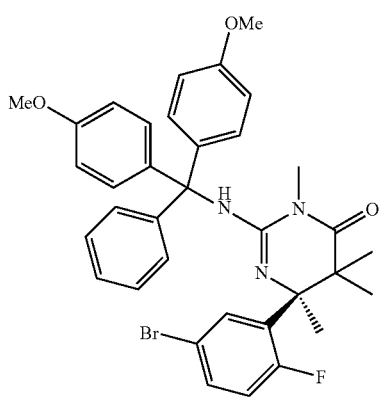

To a solution of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8, 7.0 g) in dichloromethane (100 ml) was added trifluoroacetic acid (36.3 ml) and stirring was continued at 22° C. for 4 h. The mixture was evaporated and the residue partitioned between saturated aqueous NaHCO$_3$ and dichloromethane, the organic layer was dried and evaporated and the residue triturated with n-pentane to give the intermediate (S)-2-amino-6-(5-bromo-2-fluoro-phenyl)-3,5,5,6-tetramethyl-5,6-dihydro-3H-pyrimidin-4-one (5.4 g) as a white solid. To a solution of the intermediate (0.88 g) in dichloromethane (13 ml) was added 4,4'-dimethoxytrityl chloride (0.96 g) and triethylamine (0.52 g) and stirring was continued at 22° C. for 2 h. The solution was washed with water, the organic layer was dried, evaporated and the residue was purified by chromatography over silica using AcOEt/n-heptane, gradient from 0 to 20% AcOEt) to give (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one as (1.61 g) as a pale blue solid. MS (ESI): m/z=642.3 and 644.3 [M+H]$^+$.

General Procedure A for the Synthesis of the Final Product Ib from Intermediate E or K In a microwave vial, the bromo-intermediate E or K (0.08 mmole), t-BuONa (0.16 mmole) and the amine (0.12 mmole) were charged. The tube was filled with Argon, dry toluene (1.0 ml) was added and the mixture was stirred for 2 min. Then Pd$_2$(dba)$_3$ (0.0024 mmole) and Davephos (CAS 213697-53-1) (0.016 mmole) were added and the vial was flushed with Argon and stirred for 2 min. The vial was sealed and run in the microwave at 110° C. for 15-45 min. The mixture was concentrated in vacuo and purified by flash chromatography on silica using ethyl actetate/n-heptane. To a solution of the purified product in dichloromethane (0.5 ml) was added TFA (0.4 mmole) and the mixture was stirred at room temperature for 30 min. The mixture was diluted with dichloromethane and the organic layer was washed with saturated aqueous NaHCO$_3$, dried and evaporated. The crude material was purified by chromatography on NH$_2$-silica using dichloromethane to give the pure final product Ib. In case of using intermediate E, the coupling product was deprotected using CF$_3$COOH as described above to give the pure final product Ib.

General Procedure B for the Synthesis of the Final Product Ib from Intermediate E or K In a sealed tube, the bromo-intermediate E or K (0.08 mmole), t-BuONa (0.16 mmole) and the amine (0.16 mmole) were charged. The tube was filled with Argon, dry toluene (1.0 ml) was added and the mixture was stirred for 2 min. Then Pd$_2$(dba)$_3$ (0.0024 mmole) and t-BuXphos (0.016 mmole) were added and the vial was flushed with Argon and stirred for 2 min. The reaction mixture was then heated at 100° C. for 18 h. The mixture was concentrated in vacuo and purified by flash chromatography eluting with ethyl acetate/n-heptane. To a solution of the purified product in dichloromethane (0.5 ml) was added TFA (0.4 mmole) and the mixture was stirred at room temperature for 30 min. The mixture was diluted with dichloromethane and the organic layer was washed with saturated aqueous NaHCO$_3$, dried and evaporated. The crude material was purified by chromatography on NH$_2$-silica using dichloromethane to give the pure final product Ib. In case of using intermediate E, the coupling product was deprotected using CF$_3$COOH as described above to give the pure final product Ib.

Example 1

1-Cyano-cyclopropanecarboxylic acid [3-((R)-2-amino-1,4,5,5-tetramethyl-6-oxo-1,4,5,6-tetrahydro-pyrimidin-4-yl)-phenyl]-amide

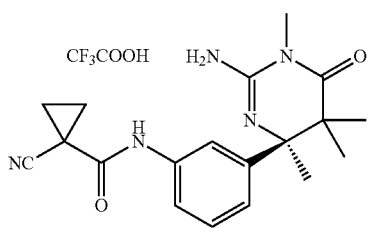 [SMILES: "CF3COOH" ; CN1C(=O)C(C)(C)[C@@](C)(c2cccc(NC(=O)C3(C#N)CC3)c2)N=C1N]

The coupling of [(R)-4-(3-amino-phenyl)-1,4,5,5-tetramethyl-6-oxo-1,4,5,6-tetrahydro-pyrimidin-2-yl]-carbamic acid tert-butyl ester (intermediate F1) and 1-cyano-cyclopropanecarboxylic acid followed by deprotection of the intermediate yielded the title compound as a white solid. MS (ESI): m/z=354.3 [M+H]$^+$.

Example 2

1-Trifluoromethyl-cyclopropanecarboxylic acid [3-((R)-2-amino-1,4,5,5-tetramethyl-6-oxo-1,4,5,6-tetrahydro-pyrimidin-4-yl)-phenyl]-amide

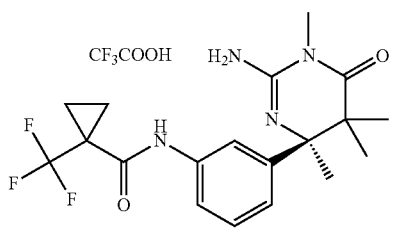 [SMILES: CN1C(=O)C(C)(C)[C@@](C)(c2cccc(NC(=O)C3(C(F)(F)F)CC3)c2)N=C1N ; "CF3COOH"]

The coupling of [(R)-4-(3-amino-phenyl)-1,4,5,5-tetramethyl-6-oxo-1,4,5,6-tetrahydro-pyrimidin-2-yl]-carbamic acid tert-butyl ester (intermediate F1) and 1-trifluoromethyl-cyclopropanecarboxylic acid followed by deprotection of the intermediate yielded the title compound as a white solid. MS (ESI): m/z=397.2 [M+H]$^+$.

Example 3

N-[3-((S)-2-Amino-1,4,5,5-tetramethyl-6-oxo-1,4,5,6-tetrahydro-pyrimidin-4-yl)-4-fluoro-phenyl]-3,3,3-trifluoro-propionamide

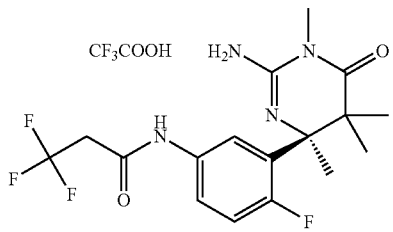 [SMILES: CN1C(=O)C(C)(C)[C@@](C)(c2cc(NC(=O)CC(F)(F)F)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 3,3,3-trifluoro-propionic acid followed by deprotection of the intermediate yielded the title compound as a white solid. MS (ESI): m/z=389.3 [M+H]$^+$.

Example 4

1-Trifluoromethyl-cyclobutanecarboxylic acid [3-((S)-2-amino-1,4,5,5-tetramethyl-6-oxo-1,4,5,6-tetrahydro-pyrimidin-4-yl)-4-fluoro-phenyl]-amide

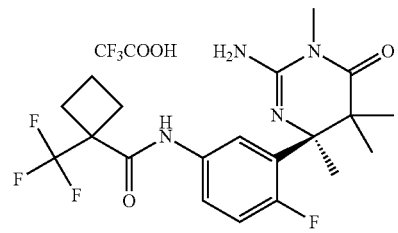 [SMILES: CN1C(=O)C(C)(C)[C@@](C)(c2cc(NC(=O)C3(C(F)(F)F)CCC3)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 1-trifluoromethyl-cyclobutanecarboxylic acid followed by deprotection of the intermediate yielded the title compound as a white solid. MS (ESI): m/z=429.3 [M+H]$^+$.

Example 5

1-Trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide

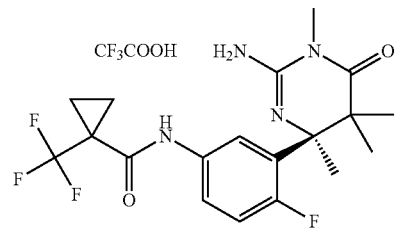 [SMILES: CN1C(=O)C(C)(C)[C@@](C)(c2cc(NC(=O)C3(C(F)(F)F)CC3)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 1-trifluoromethyl-cyclopropanecarboxylic acid followed by deprotection of the intermediate yielded the title compound as a white solid. MS (ESI): m/z=415.4 [M+H]$^+$.

Example 6

N-[3-((S)-2-Amino-1,4,5,5-tetramethyl-6-oxo-1,4,5,6-tetrahydro-pyrimidin-4-yl)-4-fluoro-phenyl]-2,2,3,3-pentafluoro-propionamide

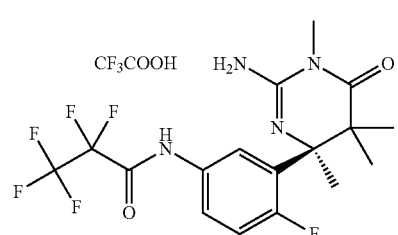

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 2,2,3,3,3-pentafluoro-propionic acid followed by deprotection of the intermediate yielded the title compound as a white solid. MS (ESI): m/z=425.2 [M+H]⁺.

Example 7

N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-trifluoromethyl-propionamide

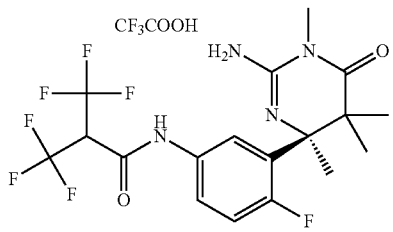 [SMILES: CN1C(=O)C(C)(C)[C@@](C)(c2cc(NC(=O)C(C(F)(F)F)C(F)(F)F)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 3,3,3-trifluoro-2-trifluoromethyl-propionic acid followed by deprotection of the intermediate yielded the title compound as a white solid. MS (ESI): m/z=457.3 [M+H]⁺.

Example 8

N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-hydroxy-propionamide

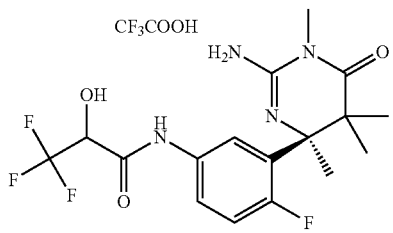 [SMILES: CN1C(=O)C(C)(C)[C@@](C)(c2cc(NC(=O)C(O)C(F)(F)F)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and rac-3,3,3-trifluoro-2-hydroxy-propionic acid followed by deprotection of the intermediate yielded the title compound as a white solid. MS (ESI): m/z=405.4 [M+H]⁺.

Examples 9 and 10

(R)-2,2-Difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide and (S)-2,2-difluoro-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide

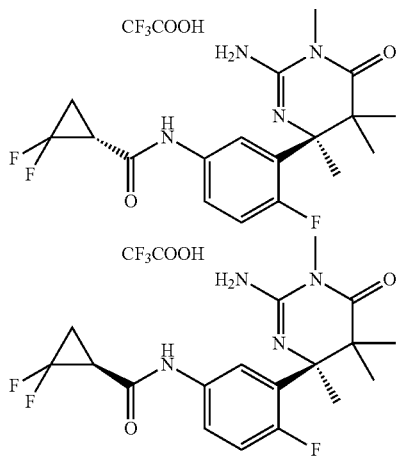

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and rac-2,2-difluoro-cyclopropanecarboxylic acid yielded a 1:1 mixture of epimers. The mixture was separated on a Chiralpack AD column using n-heptane/i-PrOH (95:5) to give ((S)-4-{5-[((R)-2,2-difluoro-cyclopropanecarbonyl)-amino]-2-fluoro-phenyl}-1,4,5,5-tetramethyl-6-oxo-1,4,5,6-tetrahydro-pyrimidin-2-yl)-carbamic acid tert-butyl ester as the faster running epimer. MS (ESI): m/z=483.4 [M+H]⁺, and ((S)-4-{5-[((S)-2,2-difluoro-cyclopropanecarbonyl)-amino]-2-fluoro-phenyl}-1,4,5,5-tetramethyl-6-oxo-1,4,5,6-tetrahydro-pyrimidin-2-yl)-carbamic acid tert-butyl ester as the slower running epimer. MS (ESI): m/z=483.4 [M+H]⁺.

The two Boc-protected isomers intermediates were deprotected to give the first title compound as a colorless solid. MS (ESI): m/z=383.2 [M+H]⁺ and the second title compound as a colorless solid. MS (ESI): m/z=383.2 [M+H]⁺.

Example 11

1-Trifluoromethyl-cyclopropanecarboxylic acid [3-((4S,5R)-2-amino-5-ethyl-1,4-dimethyl-6-oxo-1,4,5,6-tetrahydro-pyrimidin-4-yl)-phenyl]-amide

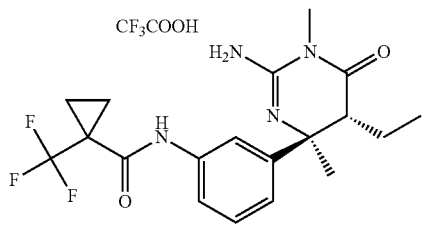 [SMILES: CC[C@H]1C(=O)N(C)C(N)=N[C@]1(C)c1cccc(NC(=O)C2(C(F)(F)F)CC2)c1 ; "CF3COOH"]

To a solution of [(S)-1,4-dimethyl-4-(3-nitro-phenyl)-6-oxo-1,4,5,6-tetrahydro-pyrimidin-2-yl]-carbamic acid tert-butyl ester (165 mg, intermediate E3) in THF (3.0 ml) was added at −78° C. a solution of LDA (3 eq., 2.8 ml) and stirring was continued for 1 h. The mixture was treated at −78° C. with a solution of iodoethane (67 µl) in THF (2.0 ml) and stirring was continued at the same temperature for 1.5 h and at −20° C. for 16 h. The mixture was quenched with saturated aqueous NH4Cl, extracted with diethyl ether, the organic layer was dried and evaporated. The residue was chromatographed on silica using n-heptane/ethyl acetate (4:1) to give [(4S,5R)-5-ethyl-1,4-dimethyl-4-(3-nitro-phenyl)-6-oxo-1,4,5,6-tetrahydro-pyrimidin-2-yl]-carbamic acid tert-butyl ester (96 mg) as a colorless foam. MS (ESI): m/z=391.3 [M+H]+.

A suspension of [(4S,5R)-5-ethyl-1,4-dimethyl-4-(3-nitro-phenyl)-6-oxo-1,4,5,6-tetrahydro-pyrimidin-2-yl]-carbamic acid tert-butyl ester (90 mg) in ethyl alcohol (2 ml), NEt3 (10 mg) and Pd/C (10%, 10 mg) was hydrogenated at normal pressure and 22° C. for 2 h. The mixture was filtered and the filtrate evaporated to give [(4S,5R)-4-(3-amino-phenyl)-5-ethyl-1,4-dimethyl-6-oxo-1,4,5,6-tetrahydro-pyrimidin-2-yl]-carbamic acid tert-butyl ester (89 mg) as a colorless foam. MS (ESI): m/z=361.4 [M+H]+.

The coupling of give [(4S,5R)-4-(3-amino-phenyl)-5-ethyl-1,4-dimethyl-6-oxo-1,4,5,6-tetrahydro-pyrimidin-2-yl]-carbamic acid tert-butyl ester and 1-trifluoromethyl-cyclopropanecarboxylic acid followed by deprotection of the intermediate yielded the title compound as a white solid. MS (ESI): m/z=397.2 [M+H]+.

Example 12

1-Trifluoromethyl-cyclopropanecarboxylic acid [3-((S)-2-amino-1,4-dimethyl-6-oxo-1,4,5,6-tetrahydro-pyrimidin-4-yl)-phenyl]-amide

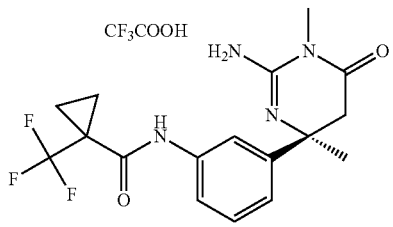 [SMILES: CN1C(=O)C[C@@](C)(c2cccc(NC(=O)C3(C(F)(F)F)CC3)c2)N=C1N ; "CF3COOH"]

The coupling of [(S)-4-(3-amino-phenyl)-1,4-dimethyl-6-oxo-1,4,5,6-tetrahydro-pyrimidin-2-yl]-carbamic acid tert-butyl ester (intermediate F3) and 1-trifluoromethyl-cyclopropanecarboxylic acid followed by deprotection of the intermediate yielded the title compound as a white solid. MS (ESI): m/z=369.2 [M+H]+.

Example 13

1-Trifluoromethyl-cyclopropanecarboxylic acid [3-((S)-2-amino-1-c-cyclopropylmethyl-4-methyl-6-oxo-1,4,5,6-tetrahydro-pyrimidin-4-yl)-phenyl]-amide

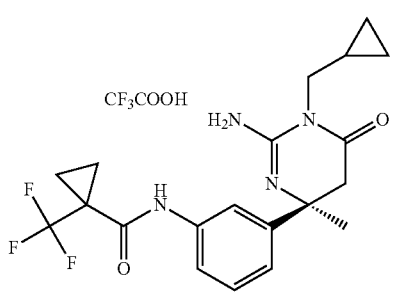 [SMILES: C[C@@]1(c2cccc(NC(=O)C3(C(F)(F)F)CC3)c2)CC(=O)N(CC2CC2)C(N)=N1 ; "CF3COOH"]

The coupling of [(S)-4-(3-amino-phenyl)-1-c-cyclopropylmethyl-4-methyl-6-oxo-1,4,5,6-tetrahydro-pyrimidin-2-yl]-carbamic acid tert-butyl ester (intermediate F4) and 1-trifluoromethyl-cyclopropanecarboxylic acid followed by deprotection of the intermediate yielded the title compound as a white solid. MS (ESI): m/z=409.3 [M+H]+.

Example 14

1-Trifluoromethyl-cyclopropanecarboxylic acid [3-((S)-2-amino-1-methyl-6-oxo-4-propyl-1,4,5,6-tetrahydro-pyrimidin-4-yl)-phenyl]-amide

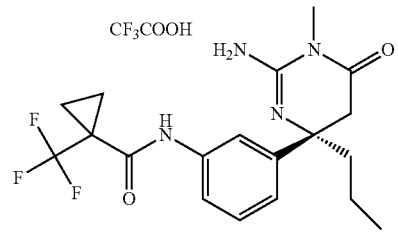 [SMILES: CCC[C@@]1(c2cccc(NC(=O)C3(C(F)(F)F)CC3)c2)CC(=O)N(C)C(N)=N1 ; "CF3COOH"]

The coupling of [(S)-4-(3-amino-phenyl)-1-methyl-6-oxo-4-propyl-1,4,5,6-tetrahydro-pyrimidin-2-yl]-carbamic acid tert-butyl ester (intermediate F5) and 1-trifluoromethyl-cyclopropanecarboxylic acid followed by deprotection of the intermediate yielded the title compound as a white solid. MS (ESI): m/z=397.2 [M+H]+.

Example 15

(S)—N-(2′-Amino-1′-methyl-6′-oxo-2,3,5′,6′-tetrahydro-1′H-spiro[indene-1,4′-pyrimidine]-6-yl)-1-(trifluoromethyl)cyclopropanecarboxamide

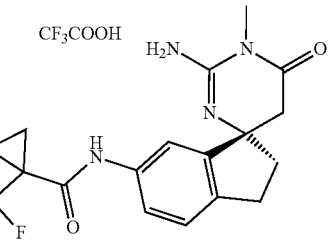

The coupling of tert-butyl [(1S)-6-amino-1′-methyl-6′-oxo-2,3,5′,6′-tetrahydro-1′H-spiro[indene-1,4′-pyrimidin]-2′-yl]carbamate (intermediate F6) and 1-trifluoromethyl-cyclopropanecarboxylic acid followed by deprotection of the intermediate yielded the title compound as a white solid. MS (ESI): m/z=381.2 [M+H]+.

Example 16

(S)—N-(3-(2-Amino-1,4,5,5-tetramethyl-6-oxo-1,4,5,6-tetrahydropyrimidin-4-yl)-4-fluorophenyl)-2-fluoro-2-methylpropanamide

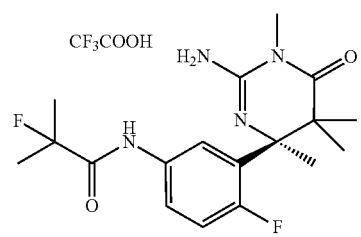 [SMILES: CN1C(=O)C(C)(C)[C@@](C)(c2cc(NC(=O)C(C)(C)F)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 2-fluoro-2-methyl-propionic acid followed by deprotection of the intermediate yielded the title compound as a colorless amorphous solid. MS (ESI): m/z=367.2 [M+H]$^+$.

Example 17

(S)—N-(3-(2-Amino-1,4,5,5-tetramethyl-6-oxo-1,4,5,6-tetrahydropyrimidin-4-yl)-4-fluorophenyl)cyclopropanecarboxamide

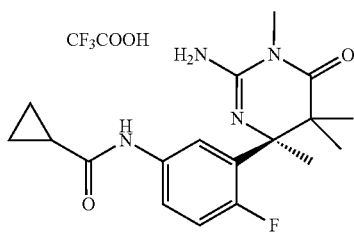 [SMILES: CN1C(=O)C(C)(C)[C@@](C)(c2cc(NC(=O)C3CC3)ccc2F)N=C1N ; "CF3COOH"]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and cyclopropanecarboxylic acid followed by deprotection of the intermediate yielded the title compound as a colorless amorphous solid. MS (ESI): m/z=347.2 [M+H]$^+$.

Example 18

(S)—N-(3-(2-Amino-1,4,5,5-tetramethyl-6-oxo-1,4,5,6-tetrahydropyrimidin-4-yl)-4-fluorophenyl)-1-methylcyclopropanecarboxamide

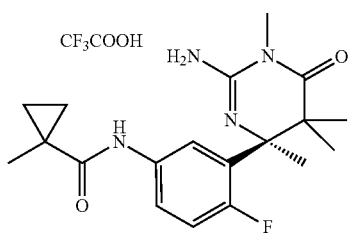

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and 1-methylcyclopropanecarboxylic acid followed by deprotection of the intermediate yielded the title compound as a colorless amorphous solid. MS (ESI): m/z=361.2 [M+H]$^+$.

Example 19

N-(3-((S)-2-Amino-1,4,5,5-tetramethyl-6-oxo-1,4,5,6-tetrahydropyrimidin-4-yl)-4-fluorophenyl)-2,2-dimethylcyclopropanecarboxamide

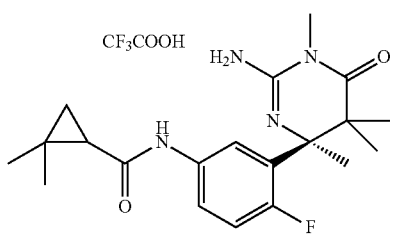

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and rac-2,2-dimethyl-cyclopropanecarboxylic acid followed by deprotection of the intermediate yielded the title compound as a colorless amorphous solid. MS (ESI): m/z=375.3 [M+H]$^+$.

Example 20

N-(3-((S)-2-Amino-1,4,5,5-tetramethyl-6-oxo-1,4,5,6-tetrahydropyrimidin-4-yl)-4-fluorophenyl)-2,3,3,3-tetrafluoro-2-methoxypropanamide

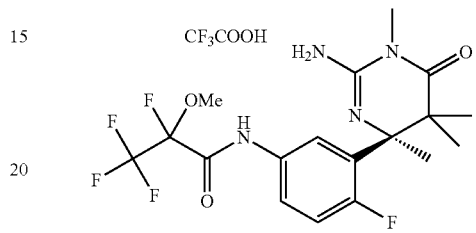

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and rac-2,3,3,3-tetrafluoro-2-methoxy-propionic acid followed by deprotection of the intermediate yielded the title compound as a colorless amorphous solid. MS (ESI): m/z=437.1 [M+H]$^+$.

Example 21

(S)-2-Amino-6-(5-(cyclopentylamino)-2-fluorophenyl)-3,5,5,6-tetramethyl-5,6-dihydropyrimidin-4(3H)-one

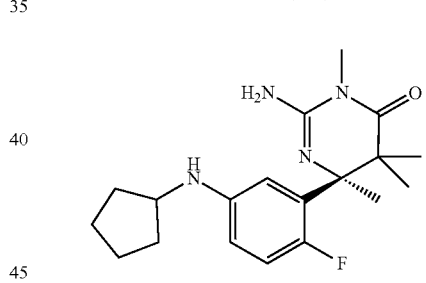

The reductive amination of (S)-2-amino-6-(5-amino-2-fluoro-phenyl)-3,5,5,6-tetramethyl-5,6-dihydro-3H-pyrimidin-4-one (intermediate J) and cyclopentanone yielded the title compound as a colorless waxy solid. MS (ESI): m/z=347.3 [M+H]$^+$.

Example 22

(S)-2-Amino-6-[2-fluoro-5-(tetrahydro-furan-3-ylamino)-phenyl]-3,5,5,6-tetramethyl-5,6-dihydro-3H-pyrimidin-4-one

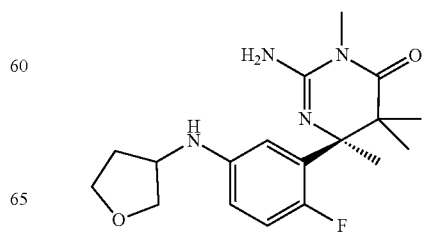

The reductive amination of (S)-2-amino-6-(5-amino-2-fluoro-phenyl)-3,5,5,6-tetramethyl-5,6-dihydro-3H-pyrimidin-4-one (intermediate J) and dihydro-furan-3-one yielded a mixture of epimers of the title compound as a colorless waxy solid. MS (ESI): m/z=349.2 [M+H]⁺.

Example 23

3-[3-((S)-2-Amino-1,4,5,5-tetramethyl-6-oxo-1,4,5,6-tetrahydro-pyrimidin-4-yl)-4-fluoro-phenylamino]-pyrrolidine-1-carboxylic acid ethyl ester

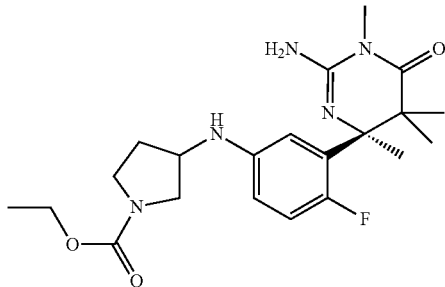 [SMILES: CCOC(=O)N1CCC(Nc2ccc(F)c([C@@]3(C)N=C(N)N(C)C(=O)C3(C)C)c2)C1]

The reductive amination of (S)-2-amino-6-(5-amino-2-fluoro-phenyl)-3,5,5,6-tetramethyl-5,6-dihydro-3H-pyrimidin-4-one (intermediate J) and 3-oxo-pyrrolidine-1-carboxylic acid ethyl ester yielded a mixture of epimers of the title compound as a colorless waxy solid. MS (ESI): m/z=420.3 [M+H]⁺.

Example 24

(S)-2-Amino-6-[2-fluoro-5-(3-methyl-cyclopentylamino)-phenyl]-3,5,5,6-tetramethyl-5,6-dihydro-3H-pyrimidin-4-one

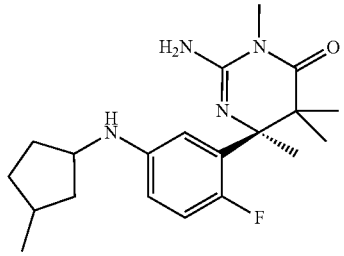 [SMILES: CC1CCC(Nc2ccc(F)c([C@@]3(C)N=C(N)N(C)C(=O)C3(C)C)c2)C1]

The reductive amination of (S)-2-amino-6-(5-amino-2-fluoro-phenyl)-3,5,5,6-tetramethyl-5,6-dihydro-3H-pyrimidin-4-one (intermediate J) and rac-3-methyl-cyclopentanone yielded a mixture of isomers of the title compound as a colorless waxy solid. MS (ESI): m/z=361.4 [M+H]⁺.

Example 25

(S)-2-Amino-6-[2-fluoro-5-(2-methyl-cyclopentylamino)-phenyl]-3,5,5,6-tetramethyl-5,6-dihydro-3H-pyrimidin-4-one

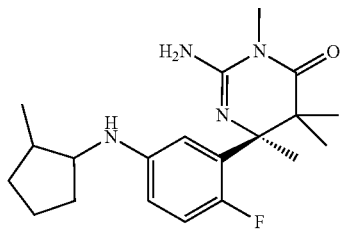 [SMILES: CC1CCCC1Nc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and rac-2-methyl-cyclopentanone yielded a mixture of isomers of the title compound as a colorless waxy solid. MS (ESI): m/z=361.4 [M+H]⁺.

Example 26

(S)—N-(3-(2-amino-1,4,5,5-tetramethyl-6-oxo-1,4,5,6-tetrahydropyrimidin-4-yl)-4-fluorophenyl)-2-cyclopentylacetamide

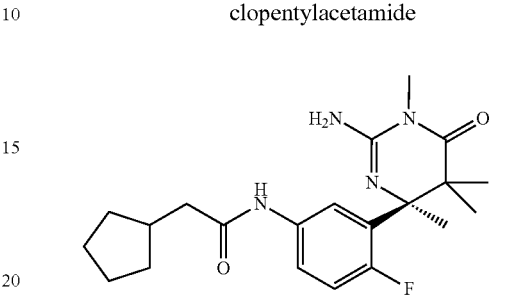

The coupling of (S)-2-amino-6-(5-amino-2-fluorophenyl)-3,5,5,6-tetramethyl-5,6-dihydropyrimidin-4(3H)-one (intermediate J) and cyclopentyl-acetic acid yielded the title compound as a white solid. MS (ESI): m/z=389.2 [M+H]⁺.

Example 27

(S)—N-(3-(2-amino-1,4,5,5-tetramethyl-6-oxo-1,4,5,6-tetrahydropyrimidin-4-yl)-4-fluorophenyl)-2-cyclobutylacetamide

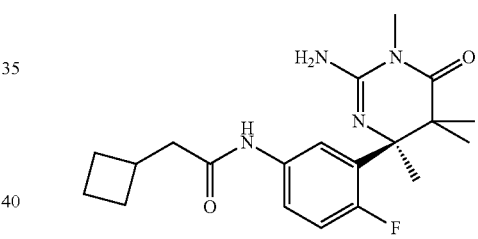

The coupling of (S)-2-amino-6-(5-amino-2-fluorophenyl)-3,5,5,6-tetramethyl-5,6-dihydropyrimidin-4(3H)-one (intermediate J) and cyclobutyl-acetic acid yielded the title compound as a white solid. MS (ESI): m/z=375.2 [M+H]⁺.

Example 28

(S)—N-(3-(2-amino-1,4,5,5-tetramethyl-6-oxo-1,4,5,6-tetrahydropyrimidin-4-yl)-4-fluorophenyl)-2-cyclopropylacetamide

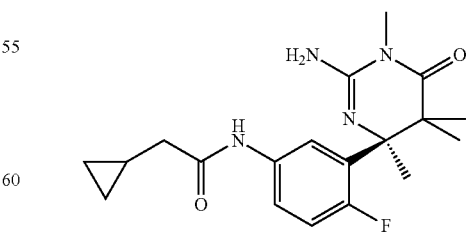

The coupling of (S)-2-amino-6-(5-amino-2-fluorophenyl)-3,5,5,6-tetramethyl-5,6-dihydropyrimidin-4(3H)-one (intermediate J) and cyclopropyl-acetic acid yielded the title compound as a white solid. MS (ESI): m/z=361.2 [M+H]⁺.

Example 29

(S)-2-Amino-6-[5-(5-chloro-indan-1-ylamino)-2-fluoro-phenyl]-3,5,5,6-tetramethyl-5,6-dihydro-3H-pyrimidin-4-one

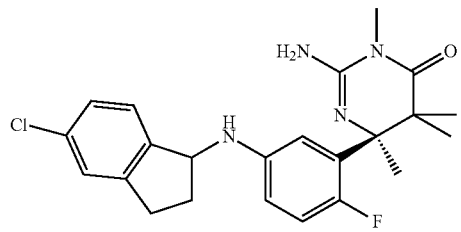 [SMILES: CN1C(=O)C(C)(C)[C@@](C)(c2cc(NC3CCc4cc(Cl)ccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 5-chloro-indan-1-one yielded a mixture of epimers of the title compound as a pale brown solid. MS (ESI): m/z=429.2 [M+H]$^+$.

Example 30

(6S)-2-Amino-6-(5-(2-chlorocyclopentylamino)-2-fluorophenyl)-3,5,5,6-tetramethyl-5,6-dihydropyrimidin-4(3H)-one

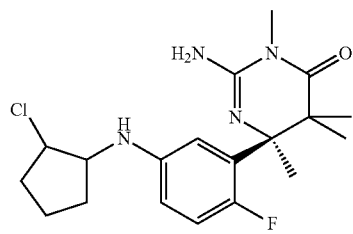 [SMILES: CN1C(=O)C(C)(C)[C@@](C)(c2cc(NC3CCCC3Cl)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and rac-2-chloro-cyclopentanone yielded a mixture of isomers of the title compound as a pale brown solid. MS (ESI): m/z=381.3 [M+H]$^+$.

Example 31

(6S)-2-Amino-6-(2-fluoro-5-(1-(4-fluorophenyl)pyrrolidin-3-ylamino)phenyl)-3,5,5,6-tetramethyl-5,6-dihydropyrimidin-4(3H)-one

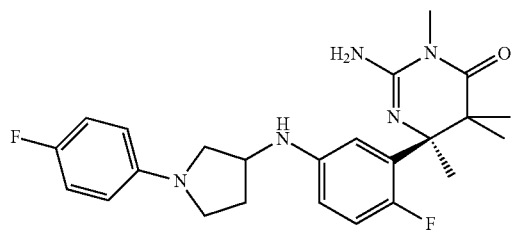 [SMILES: CN1C(=O)C(C)(C)[C@@](C)(c2cc(NC3CCN(c4ccc(F)cc4)C3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-(4-fluoro-phenyl)-pyrrolidin-3-one yielded a mixture of epimers of the title compound as a pale orange solid. MS (ESI): m/z=442.3 [M+H]$^+$.

Example 32

(6S)-2-Amino-6-(5-(1-benzylpyrrolidin-3-ylamino)-2-fluorophenyl)-3,5,5,6-tetramethyl-5,6-dihydropyrimidin-4(3H)-one

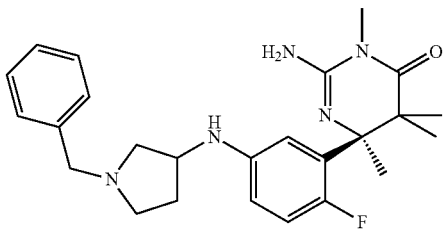 [SMILES: CN1C(=O)C(C)(C)[C@@](C)(c2cc(NC3CCN(Cc4ccccc4)C3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-benzyl-pyrrolidin-3-one yielded a mixture of epimers of the title compound as a pale brown solid. MS (ESI): m/z=438.3 [M+H]$^+$.

Example 33

(6S)-2-Amino-6-(2-fluoro-5-(3-phenylcyclopentylamino)phenyl)-3,5,5,6-tetramethyl-5,6-dihydropyrimidin-4(3H)-one

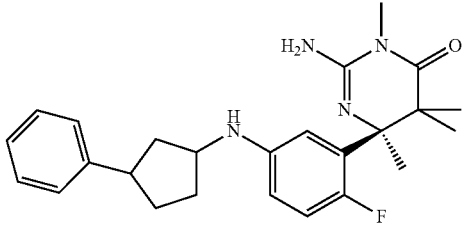 [SMILES: CN1C(=O)C(C)(C)[C@@](C)(c2cc(NC3CCC(c4ccccc4)C3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and rac-3-phenyl-cyclopentanone yielded a mixture of isomers of the title compound as a white foam. MS (ESI): m/z=423.2 [M+H]$^+$.

Example 34

(6S)-2-Amino-6-(2-fluoro-5-(2-methyltetrahydrofuran-3-ylamino)phenyl)-3,5,5,6-tetramethyl-5,6-dihydropyrimidin-4(3H)-one

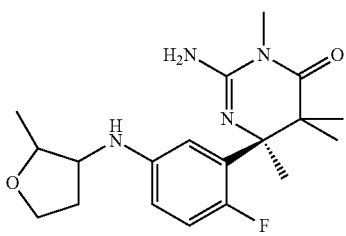 [SMILES: CC1OCCC1Nc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and rac-2-methyl-dihydro-furan-3-one yielded a mixture of isomers of the title compound as an off-white solid. MS (ESI): m/z=363.3 [M+H]$^+$.

Example 35

(6S)-2-Amino-6-(2-fluoro-5-(5-fluoro-2,3-dihydro-1H-inden-1-ylamino)phenyl)-3,5,5,6-tetramethyl-5,6-dihydropyrimidin-4(3H)-one

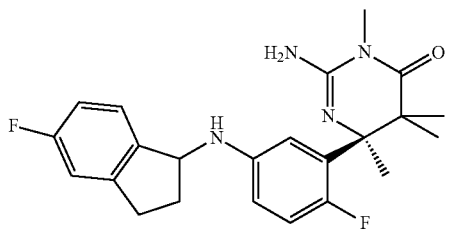 [SMILES: CN1C(=O)C(C)(C)[C@@](C)(c2cc(NC3CCc4cc(F)ccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 5-fluoro-indan-1-one yielded a mixture of epimers of the title compound as a pale brown waxy solid. MS (ESI): m/z=413.3 [M+H]+.

Example 36

(S)-2-Amino-6-[2-fluoro-5-(2-methyl-2H-pyrazol-3-ylamino)-phenyl]-3,5,5,6-tetramethyl-5,6-dihydro-3H-pyrimidin-4-one

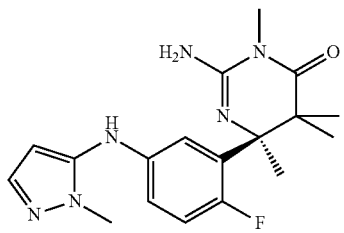 [SMILES: CN1C(=O)C(C)(C)[C@@](C)(c2cc(Nc3ccnn3C)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 2-methyl-2H-pyrazol-3-ylamine according to procedure B followed by deprotection yielded the title compound as a pale brown waxy solid. MS (ESI): m/z=359.2 [M+H]+.

Example 37

(S)-2-Amino-6-[5-(1-cyclopropyl-ethylamino)-2-fluoro-phenyl]-3,5,5,6-tetramethyl-5,6-dihydro-3H-pyrimidin-4-one

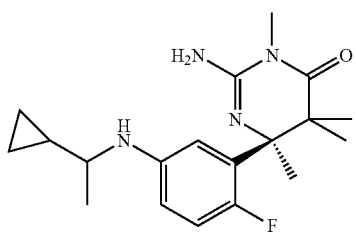 [SMILES: CC(Nc1ccc(F)c([C@@]2(C)N=C(N)N(C)C(=O)C2(C)C)c1)C1CC1]

The reductive amination of (S)-2-amino-6-(5-amino-2-fluoro-phenyl)-3,5,5,6-tetramethyl-5,6-dihydro-3H-pyrimidin-4-one (intermediate J) and 1-cyclopropyl-ethanone yielded a mixture of epimers of the title compound as a colorless foam. MS (ESI): m/z=347.3 [M+H]+.

Example 38

(S)-2-Amino-6-[2-fluoro-5-(1-phenyl-ethylamino)-phenyl]-3,5,5,6-tetramethyl-5,6-dihydro-3H-pyrimidin-4-one

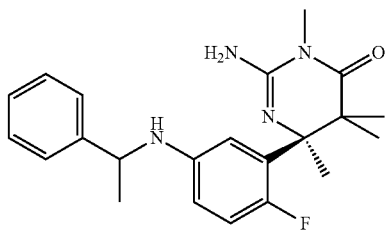 [SMILES: CC(Nc1ccc(F)c([C@@]2(C)N=C(N)N(C)C(=O)C2(C)C)c1)c1ccccc1]

The reductive amination of (S)-2-amino-6-(5-amino-2-fluoro-phenyl)-3,5,5,6-tetramethyl-5,6-dihydro-3H-pyrimidin-4-one (intermediate J) and 1-phenyl-ethanone yielded a mixture of epimers of the title compound as a colorless solid. MS (ESI): m/z=383.3 [M+H]+.

Example 39

(S)-2-Amino-6-[5-(2,5-dimethyl-2H-pyrazol-3-ylamino)-2-fluoro-phenyl]-3,5,5,6-tetramethyl-5,6-dihydro-3H-pyrimidin-4-one

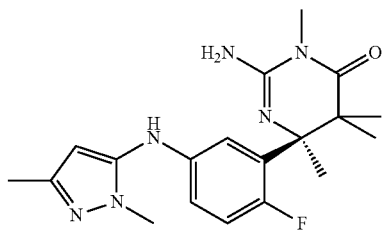

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 2,5-dimethyl-2H-pyrazol-3-ylamine according to procedure B followed by deprotection yielded the title compound as a black waxy solid. MS (ESI): m/z=373.2 [M+H]+.

Example 40

(S)-2-Amino-6-[2-fluoro-5-(1-phenyl-ethylamino)-phenyl]-3,5,5,6-tetramethyl-5,6-dihydro-3H-pyrimidin-4-one

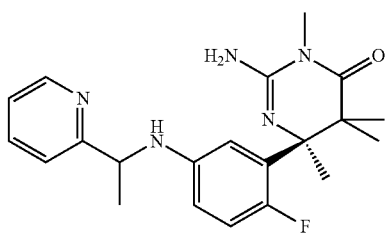

The reductive amination of (S)-2-amino-6-(5-amino-2-fluoro-phenyl)-3,5,5,6-tetramethyl-5,6-dihydro-3H-pyrimidin-4-one (intermediate J) and 1-pyridin-2-yl-ethanone yielded a mixture of epimers of the title compound as an off white foam. MS (ESI): m/z=384.3 [M+H]+.

Example 41

(S)-2-amino-6-(2-fluoro-5-(4-(trifluoromethyl)cyclohexylamino)phenyl)-3,5,5,6-tetramethyl-5,6-dihydropyrimidin-4(3H)-one

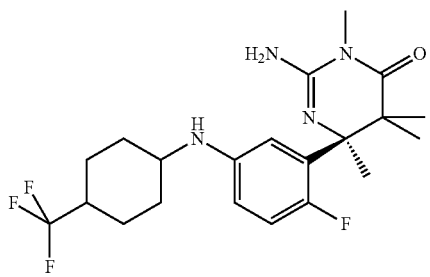 [SMILES: CN1C(=O)C(C)(C)[C@@](C)(c2cc(NC3CCC(C(F)(F)F)CC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 4-trifluoromethyl-cyclohexanone yielded a mixture of isomers of the title compound as a white solid. MS (ESI): m/z=429.2 [M+H]$^+$.

Example 42

(S)-2-Amino-6-{2-fluoro-5-[2-(4-fluoro-phenyl)-1-methyl-ethylamino]-phenyl}-3,5,5,6-tetramethyl-5,6-dihydro-3H-pyrimidin-4-one

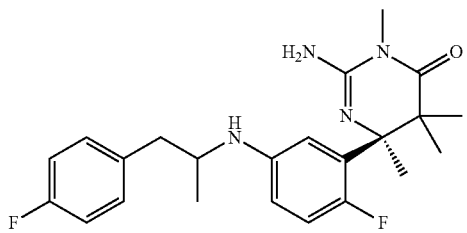 [SMILES: CC(Cc1ccc(F)cc1)Nc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and 1-(4-fluoro-phenyl)-propan-2-one yielded a mixture of epimers of the title compound as a white solid. MS (ESI): m/z=415.4 [M+H]$^+$.

Example 43

(S)-2-Amino-6-[5-(1-benzyl-piperidin-4-ylamino)-2-fluoro-phenyl]-3,5,5,6-tetramethyl-5,6-dihydro-3H-pyrimidin-4-one

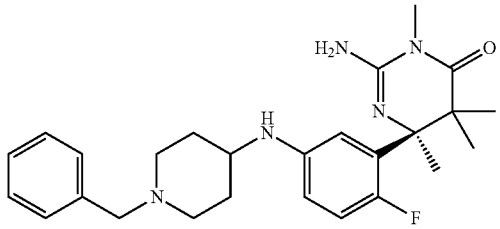 [SMILES: CN1C(=O)C(C)(C)[C@@](C)(c2cc(NC3CCN(Cc4ccccc4)CC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-benzyl-piperidin-4-one yielded the title compound as an off white solid. MS (ESI): m/z=452.3 [M+H]$^+$.

Example 44

(S)-2-Amino-6-[5-(1-benzyl-piperidin-3-ylamino)-2-fluoro-phenyl]-3,5,5,6-tetramethyl-5,6-dihydro-3H-pyrimidin-4-one

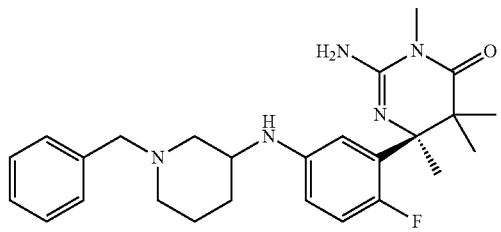 [SMILES: CN1C(=O)C(C)(C)[C@@](C)(c2cc(NC3CCCN(Cc4ccccc4)C3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-benzyl-piperidin-3-one yielded a mixture of epimers of the title compound as a pale brown foam. MS (ESI): m/z=452.2 [M+H]$^+$.

Example 45

(S)-2-Amino-6-[2-fluoro-5-(tetrahydro-pyran-3-ylamino)-phenyl]-3,5,5,6-tetramethyl-5,6-dihydro-3H-pyrimidin-4-one

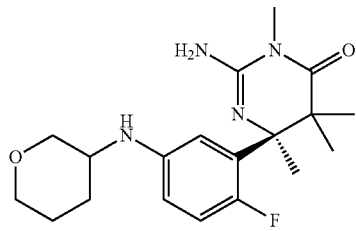 [SMILES: CN1C(=O)C(C)(C)[C@@](C)(c2cc(NC3CCCOC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and dihydro-pyran-3-one yielded a mixture of epimers of the title compound as a white solid. MS (ESI): m/z=363.3 [M+H]$^+$.

Example 46

(S)-2-Amino-6-[2-fluoro-5-(3,3,6-trimethyl-indan-1-ylamino)-phenyl]-3,5,5,6-tetramethyl-5,6-dihydro-3H-pyrimidin-4-one

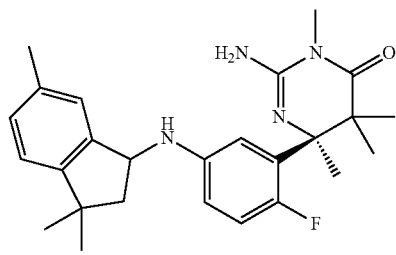 [SMILES: Cc1ccc2c(c1)C(Nc1ccc(F)c([C@@]3(C)N=C(N)N(C)C(=O)C3(C)C)c1)CC2(C)C]

The reductive amination of (S)-2-amino-6-(5-amino-2-fluoro-phenyl)-3,5,5,6-tetramethyl-5,6-dihydro-3H-pyrimidin-4-one (intermediate J) and 3,3,6-trimethyl-indan-1-one (prepared according to Vogt P. F. et al, Synth. Commun., 31(5), 679, 2001) yielded a mixture of epimers of the title compound as a pale yellow waxy solid. MS (ESI): m/z=437.3 [M+H]$^+$.

Example 47

(S)-2-Amino-6-[2-fluoro-5-(4-methoxy-indan-1-ylamino)-phenyl]-3,5,5,6-tetramethyl-5,6-dihydro-3H-pyrimidin-4-one

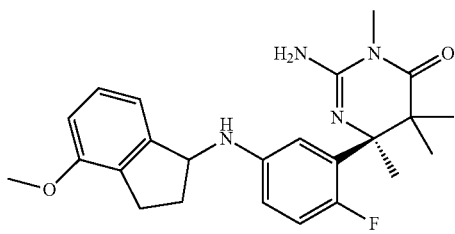

The reductive amination of (S)-2-amino-6-(5-amino-2-fluoro-phenyl)-3,5,5,6-tetramethyl-5,6-dihydro-3H-pyrimidin-4-one (intermediate J) and 4-methoxy-indan-1-one yielded a mixture of epimers of the title compound as a colorless waxy solid. MS (ESI): m/z=425.2 [M+H]$^+$.

Example 48

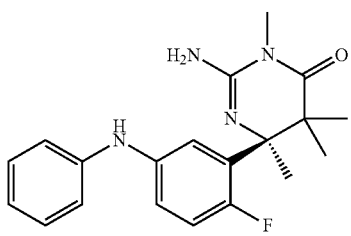 [SMILES: CN1C(=O)C(C)(C)[C@@](C)(c2cc(Nc3ccccc3)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and phenylamine according to procedure A followed by deprotection yielded the title compound as a pale brown solid. MS (ESI): m/z=355.2 [M+H]$^+$.

Example 49

(S)-2-Amino-6-[5-(7-chloro-indan-1-ylamino)-2-fluoro-phenyl]-3,5,5,6-tetramethyl-5,6-dihydro-3H-pyrimidin-4-one

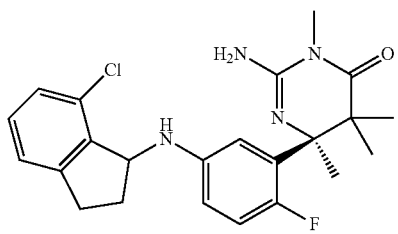 [SMILES: CN1C(=O)C(C)(C)[C@@](C)(c2cc(NC3CCc4cccc(Cl)c43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 7-chloro-indan-1-one using decaborane yielded a mixture of epimers of the title compound as a white foam. MS (ESI): m/z=429.3 [M+H]$^+$.

Example 50

(S)-2-Amino-6-[2-fluoro-5-(tetrahydro-pyran-4-ylamino)-phenyl]-3,5,5,6-tetramethyl-5,6-dihydro-3H-pyrimidin-4-one

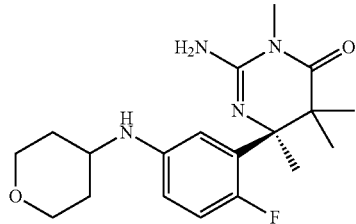 [SMILES: CN1C(=O)C(C)(C)[C@@](C)(c2cc(NC3CCOCC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and tetrahydro-pyran-4-one yielded the title compound as a colorless waxy solid. MS (ESI): m/z=363.3 [M+H]$^+$.

Example 51

(6S)-2-amino-6-(5-(2,3-dihydrobenzofuran-3-ylamino)-2-fluorophenyl)-3,5,5,6-tetramethyl-5,6-dihydropyrimidin-4(3H)-one

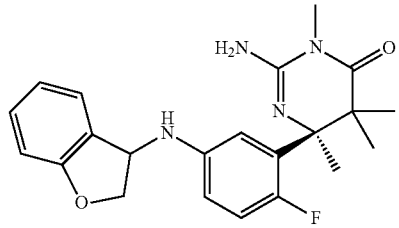 [SMILES: CN1C(=O)C(C)(C)[C@@](C)(c2cc(NC3COc4ccccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 2,3-dihydrobenzofuran-3-one using decaborane yielded a mixture of epimers of the title compound as a colorless waxy solid. MS (ESI): m/z=397.2 [M+H]$^+$.

Example 52

(S)-2-Amino-6-(5-(C-cyclopropylmethylamino)-2-fluorophenyl)-3,5,5,6-tetramethyl-5,6-dihydropyrimidin-4(3H)-one

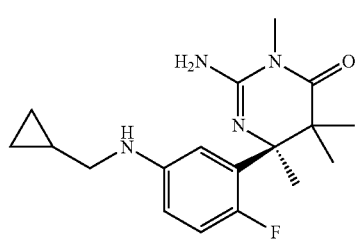 [SMILES: CN1C(=O)C(C)(C)[C@@](C)(c2cc(NCC3CC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and cyclopropanecarbaldehyde yielded the title compound as a colorless solid. MS (ESI): m/z=333.4 [M+H]$^+$.

Example 53

(S)-2-Amino-6-{2-fluoro-5-[(1-phenyl-cyclopropyl-methyl)-amino]-phenyl}-3,5,5,6-tetramethyl-5,6-dihydro-3H-pyrimidin-4-one

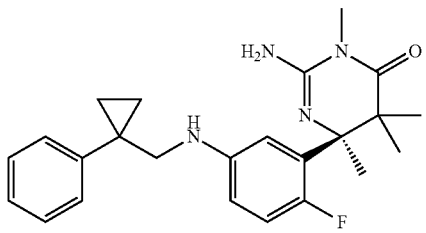 [SMILES: CN1C(=O)C(C)(C)[C@@](C)(c2cc(NCC3(c4ccccc4)CC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-phenyl-cyclopropanecarbaldehyde yielded the title compound as a colorless solid. MS (ESI): m/z=409.4 [M+H]$^+$.

Example 54

(S)-2-Amino-6-(2-fluoro-5-(3,3,3-trifluoropropylamino)phenyl)-3,5,5,6-tetramethyl-5,6-dihydropyrimidin-4(3H)-one

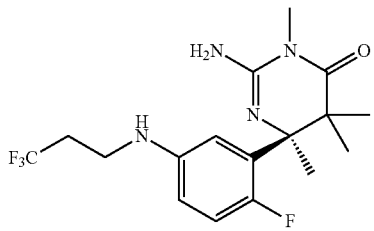 [SMILES: CN1C(=O)C(C)(C)[C@@](C)(c2cc(NCCC(F)(F)F)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 3,3,3-trifluoro-propionaldehyde yielded the title compound as a pale yellow oil. MS (ESI): m/z=375.3 [M+H]$^+$.

Example 55

(S)-2-Amino-6-(2-fluoro-5-(o-tolylamino)phenyl)-3,5,5,6-tetramethyl-5,6-dihydro-pyrimidin-4(3H)-one

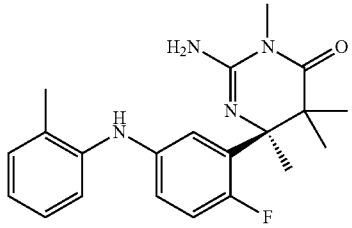 [SMILES: Cc1ccccc1Nc1ccc(F)c([C@@]2(C)N=C(N)N(C)C(=O)C2(C)C)c1]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and o-tolylamine according to procedure A followed by deprotection yielded the title compound as a white solid. MS (ESI): m/z=369.2 [M+H]$^+$.

Example 56

(S)-2-Amino-6-(2-fluoro-5-(2-methoxyphenylamino)phenyl)-3,5,5,6-tetramethyl-5,6-dihydropyrimidin-4(3H)-one

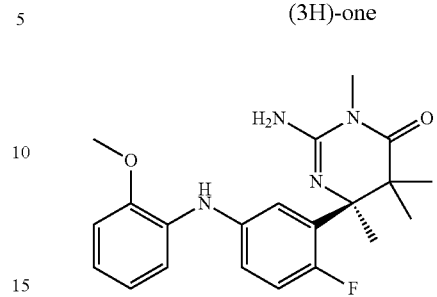

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 2-methoxyphenylamine according to procedure A followed by deprotection yielded the title compound as a white solid. MS (ESI): m/z=385.3 [M+H]$^+$.

Example 57

(S)-2-Amino-6-(2-fluoro-5-(neopentylamino)phenyl)-3,5,5,6-tetramethyl-5,6-dihydropyrimidin-4(3H)-one

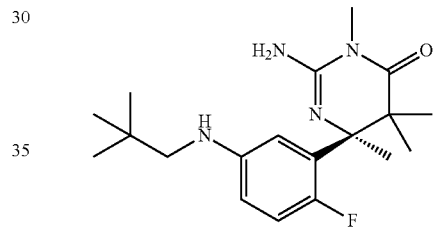

The reductive amination of (S)-2-amino-6-(5-amino-2-fluoro-phenyl)-3,5,5,6-tetramethyl-5,6-dihydro-3H-pyrimidin-4-one (intermediate J) and 2,2-dimethyl-propionaldehyde yielded the title compound as a white solid. MS (ESI): m/z=349.4 [M+H]$^+$.

Example 58

(S)-2-Amino-6-{5-[(2,2-difluoro-cyclopropylmethyl)-amino]-2-fluoro-phenyl}-3,5,5,6-tetramethyl-5,6-dihydro-3H-pyrimidin-4-one

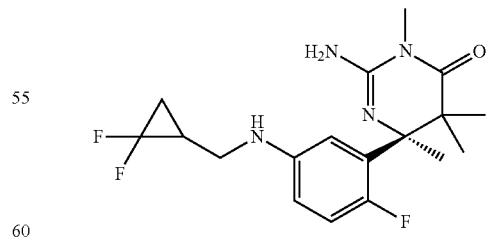

The reductive amination of (S)-2-amino-6-(5-amino-2-fluoro-phenyl)-3,5,5,6-tetramethyl-5,6-dihydro-3H-pyrimidin-4-one (intermediate J) and rac-2,2-difluoro-cyclopropanecarbaldehyde yielded a mixture of epimers of the title compound as a colorless solid. MS (ESI): m/z=369.2 [M+H]$^+$.

Example 59

(S)-2-Amino-6-{2-fluoro-5-[(pyridin-2-ylmethyl)-amino]-phenyl}-3,5,5,6-tetramethyl-5,6-dihydro-3H-pyrimidin-4-one

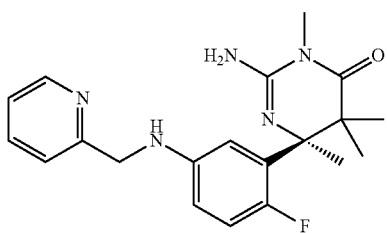 [SMILES: CN1C(=O)C(C)(C)[C@@](C)(c2cc(NCc3ccccn3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and pyridine-2-carbaldehyde yielded the title compound as a colorless solid. MS (ESI): m/z=370.3 [M+H]$^+$.

Example 60

(S)-2-Amino-6-{2-fluoro-5-[(1-methyl-1H-pyrazol-3-ylmethyl)-amino]-phenyl}-3,5,5,6-tetramethyl-5,6-dihydro-3H-pyrimidin-4-one

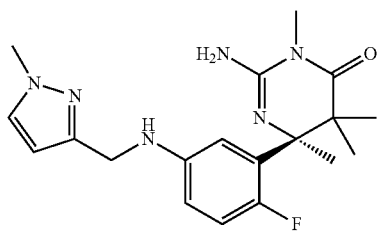 [SMILES: CN1C(=O)C(C)(C)[C@@](C)(c2cc(NCc3ccn(C)n3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-methyl-1H-pyrazole-3-carbaldehyde yielded the title compound as a colorless solid. MS (ESI): m/z=373.3 [M+H]$^+$.

Example 61

(S)-2-Amino-6-{2-fluoro-5-[(1H-pyrazol-3-ylmethyl)-amino]-phenyl}-3,5,5,6-tetramethyl-5,6-dihydro-3H-pyrimidin-4-one

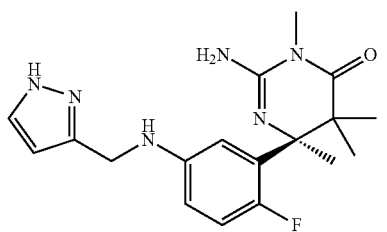 [SMILES: CN1C(=O)C(C)(C)[C@@](C)(c2cc(NCc3cc[nH]n3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1H-pyrazole-3-carbaldehyde yielded the title compound as a colorless solid. MS (ESI): m/z=359.4 [M+H]$^+$.

Example 62

(6S)-2-Amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one

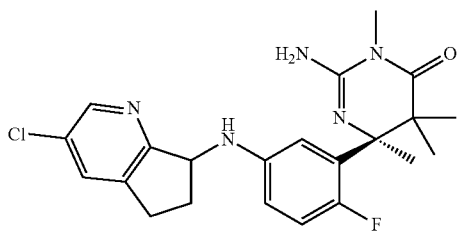 [SMILES: CN1C(=O)C(C)(C)[C@@](C)(c2cc(NC3CCc4cc(Cl)cnc43)ccc2F)N=C1N]

3-Chloro-6,7-dihydro-5H-cyclopentapyridine 1-oxide

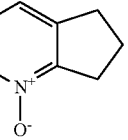

Cyclopentapyridine (3.03 g, 19.7 mmole, prepared according to Frissen, A. E. eta al., Tetrahedron, 1989, 45(16), 5151) was dissolved in acetic acid (19.7 ml) at 22° C. and H2O2 (3.45 ml, 39.5 mmole) was added slowly. The mixture was heated to 70° C. and stirred at this temperature for 20 h. After completion of the reaction, the mixture was cooled to 22° C. and evaporated. The residue was dissolved in water and evaporated again. The procedure was repeated twice. The residue was dissolved in EtOAc, washed with aqueous saturated NaHCO3 solution and brine, dried over Na2SO4 and the solvent was evaporated to give the crude title compound as dark green crystals (2.073 g, 62% yield). MS (ESI): m/z=170.1 [M+H]$^+$.

3-Chloro-6,7-dihydro-5H-cyclopentapyridin-7-yl acetate

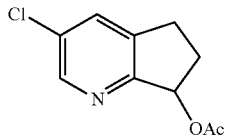 [SMILES: CC(=O)OC1CCc2cc(Cl)cnc21]

A solution of 3-chloro-6,7-dihydro-5H-cyclopentapyridine 1-oxide (1 g, 5.9 mmole) in acetic anhydride (30 ml) was heated to 110° C. and stirred at this temperature for 20 h. The solvent was evaporated and the residue was partitioned between aqueous saturated NaHCO3 solution and dichloromethane. The organic layer was dried, evaporated and the residue was purified by flash chromatography over silica using EtOAc/n-heptane (gradient from 0% to 30% EtOAc) to give the title compound as a red liquid (880 mg, 71% yield). MS (ESI): m/z=212.0 [M+H]+.

3-Chloro-6,7-dihydro-5H-cyclopentapyridin-7-ol

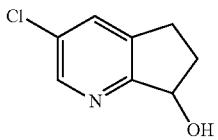 [SMILES: OC1CCc2cc(Cl)cnc21]

To a solution of 3-chloro-6,7-dihydro-5H-cyclopentapyridin-7-yl acetate (1.57 g, 7.42 mmole) in MeOH (36 ml) was added aqueous NaOH solution (1M, 8.9 ml, 8.9 mmole) and the mixture was stirred at 22° C. for 1.5 h. The mixture was diluted with water and extracted with dichloromethane, the organic layer was dried and evaporated to give the title compound as a dark red liquid which crystallized on standing. MS (ESI): m/z=170.1 [M+H]+.

3-Chloro-5H-cyclopentapyridin-7(6H)-one

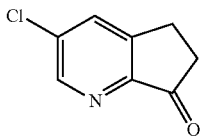 [SMILES: O=C1CCc2cc(Cl)cnc21]

To a solution of 3-chloro-6,7-dihydro-5H-cyclopentapyridin-7-ol (483 mg, 2.85 mmole) in dimethylsulfoxide (15 ml) was subsequently added at 22° C. NEt$_3$ (2.38 ml, 17.1 mmole) and pyridine.SO$_3$ complex (1.36 g, 8.54 mmole) and the solution stirred at this temperature for 1.5 h. The mixture was partitioned between water and dichloromethane, the organic layer was dried, evaporated and the residue was purified by flash chromatography over silica using EtOAc/n-heptane (gradient from 0 to 50% EtOAc) to give the title compound as a silver crystalline solid (348 mg, 73% yield). MS (ESI): m/z=168.2 [M+H]+.

The reductive amination of (S)-2-amino-6-(5-amino-2-fluoro-phenyl)-3,5,5,6-tetramethyl-5,6-dihydro-3H-pyrimidin-4-one (intermediate J) and 3-chloro-5H-cyclopentapyridin-7(6H)-one using decaborane yielded (6S)-2-amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one as a white foam. MS (ESI): m/z=430.3 [M+H]+.

Example 63

(6S)-2-Amino-6-(2-fluoro-5-(7-fluoro-2,3-dihydro-1H-inden-1-ylamino)phenyl)-3,5,5,6-tetramethyl-5,6-dihydropyrimidin-4(3H)-one

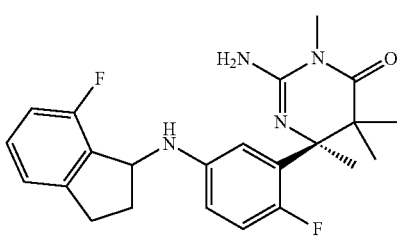 [SMILES: CN1C(=O)C(C)(C)[C@@](C)(c2cc(NC3CCc4cccc(F)c43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 7-fluoro-indan-1-one using decaborane yielded a mixture of epimers of the title compound as a white foam. MS (ESI): m/z=430.3 [M+H]+.

Example 64

(S)-2-Amino-6-[2-fluoro-5-(2,2,2-trifluoro-1-methyl-ethylamino)-phenyl]-3,5,5,6-tetramethyl-5,6-dihydro-3H-pyrimidin-4-one

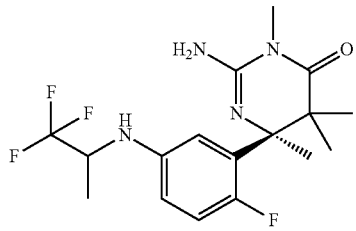 [SMILES: CC(Nc1ccc(F)c([C@@]2(C)N=C(N)N(C)C(=O)C2(C)C)c1)C(F)(F)F]

The reductive amination of (S)-2-amino-6-(5-amino-2-fluoro-phenyl)-3,5,5,6-tetramethyl-5,6-dihydro-3H-pyrimidin-4-one (intermediate J) and 1,1,1-trifluoro-propan-2-one using decaborane yielded a mixture of epimers of the title compound as a white foam. MS (ESI): m/z=375.3 [M+H]+.

Example 65

2-(3-(3-((S)-2-Amino-1,4,5,5-tetramethyl-6-oxo-1,4,5,6-tetrahydropyrimidin-4-yl)-4-fluorophenylamino)-2,3-dihydro-1H-inden-1-yl)acetic acid

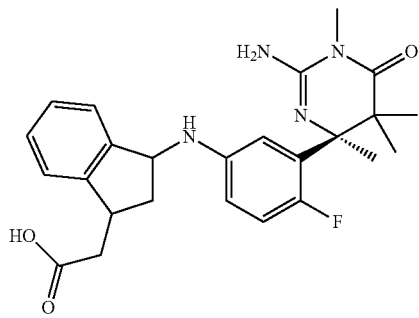 [SMILES: CN1C(=O)C(C)(C)[C@@](C)(c2cc(NC3CC(CC(=O)O)c4ccccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and rac-(3-oxo-indan-1-yl)-acetic acid yielded a mixture of isomers of the title compound as a colorless waxy solid. MS (ESI): m/z=453.2 [M+H]+.

Example 66

(S)-2-Amino-6-(2-fluoro-5-(p-tolylamino)phenyl)-3,5,5,6-tetramethyl-5,6-dihydropyrimidin-4(3H)-one

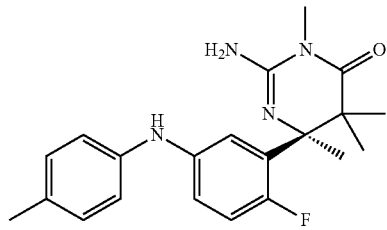

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and p-tolylamine according to procedure A followed by deprotection yielded the title compound as an off white solid. MS (ESI): m/z=369.2 [M+H]+.

Example 67

(6S)-2-Amino-6-(2-fluoro-5-(7-methyl-2,3-dihydro-1H-inden-1-ylamino)phenyl)-3,5,5,6-tetramethyl-5,6-dihydropyrimidin-4(3H)-one

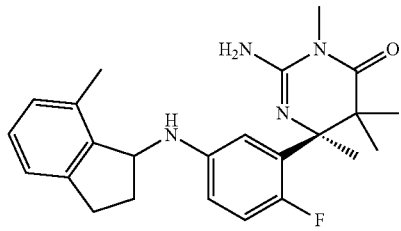 [SMILES: Cc1cccc2c1C(Nc1ccc(F)c([C@@]3(C)N=C(N)N(C)C(=O)C3(C)C)c1)CC2]

The reductive amination of (S)-2-amino-6-(5-amino-2-fluoro-phenyl)-3,5,5,6-tetramethyl-5,6-dihydro-3H-pyrimidin-4-one (intermediate J) and 7-methyl-indan-1-one using decaborane yielded a mixture of epimers of the title compound as a colorless waxy solid. MS (ESI): m/z=409.3 [M+H]$^+$.

Example 68

(S)-2-Amino-6-{5-[(2,2-difluoro-1-methyl-cyclopropylmethyl)-amino]-2-fluoro-phenyl}-3,5,5,6-tetramethyl-5,6-dihydro-3H-pyrimidin-4-one

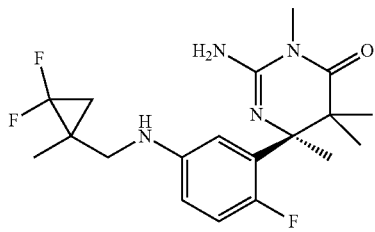 [SMILES: CN1C(=O)C(C)(C)[C@@](C)(c2cc(NCC3(C)CC3(F)F)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 2,2-difluoro-1-methyl-cyclopropanecarbaldehyde (prepared according to Gassen, K. R. et al., J. of Fluorine Chemistry 1990, 49(1), 127) yielded a mixture of isomers of the title compound as a white solid. MS (ESI): m/z=397.2 [M+H]$^+$.

Example 69

(S)-2-Amino-6-(2-fluoro-5-(2-fluorophenylamino)phenyl)-3,5,5,6-tetramethyl-5,6-dihydropyrimidin-4(3H)-one

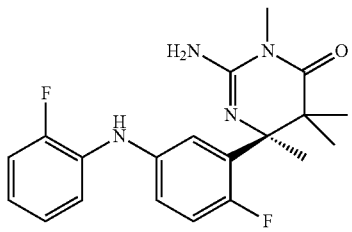 [SMILES: CN1C(=O)C(C)(C)[C@@](C)(c2cc(Nc3ccccc3F)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 2-fluorophenylamine according to procedure A followed by deprotection yielded the title compound as a white solid. MS (ESI): m/z=373.1 [M+H]$^+$.

Example 70

(S)-2-Amino-6-[5-(C-cyclobutylmethyl-amino)-2-fluoro-phenyl]-3,5,5,6-tetramethyl-5,6-dihydro-3H-pyrimidin-4-one

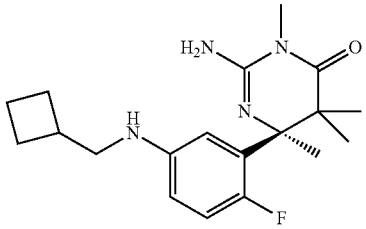 [SMILES: CN1C(=O)C(C)(C)[C@@](C)(c2cc(NCC3CCC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and cyclobutanecarbaldehyde yielded the title compound as a colorless solid. MS (ESI): m/z=347.3 [M+H]$^+$.

Example 71

(S)-2-Amino-6-{2-fluoro-5-[(3-methyl-oxetan-3-ylmethyl)-amino]-phenyl}-3,5,5,6-tetramethyl-5,6-dihydro-3H-pyrimidin-4-one

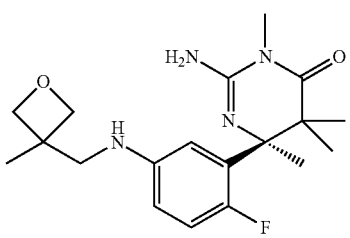

The reductive amination of (S)-2-amino-6-(5-amino-2-fluoro-phenyl)-3,5,5,6-tetramethyl-5,6-dihydro-3H-pyrimidin-4-one (intermediate J) and 3-methyl-oxetane-3-carbaldehyde (prepared according to Mccormick, K. D. et al., International patent application WO 2010/027567) yielded the title compound as a colorless solid. MS (ESI): m/z=363.4 [M+H]$^+$.

Example 72

(S)-2-Amino-6-(2-fluoro-5-(4-methoxyphenylamino)phenyl)-3,5,5,6-tetramethyl-5,6-dihydropyrimidin-4(3H)-one

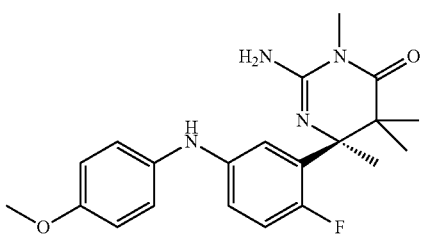

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 4-methoxyphenylamine according to procedure A followed by deprotection yielded the title compound as an off white solid. MS (ESI): m/z=385.2 [M+H]$^+$.

Example 73

(S)-2-Amino-6-(5-(2-(difluoromethoxy)phenylamino)-2-fluorophenyl)-3,5,5,6-tetramethyl-5,6-dihydropyrimidin-4(3H)-one

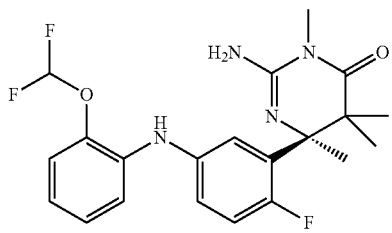 [SMILES: CN1C(=O)C(C)(C)[C@@](C)(c2cc(Nc3ccccc3OC(F)F)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and difluoromethoxy)phenylamine according to procedure A followed by deprotection yielded the title compound as a white solid. MS (ESI): m/z=421.1 [M+H]+.

Example 74

(S)-2-Amino-6-(2-fluoro-5-(2-(trifluoromethoxy)phenylamino)phenyl)-3,5,5,6-tetramethyl-5,6-dihydropyrimidin-4(3H)-one

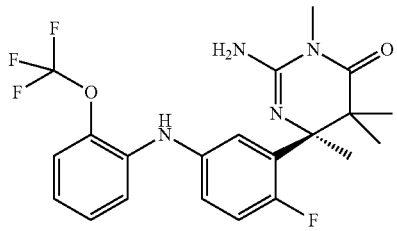 [SMILES: CN1C(=O)C(C)(C)[C@@](C)(c2cc(Nc3ccccc3OC(F)(F)F)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and o-(trifluoromethoxy)phenylamine according to procedure A followed by deprotection yielded the title compound as a white solid. MS (ESI): m/z=439.3 [M+H]+.

Example 75

(S)-2-Amino-6-(2-fluoro-5-(2,2,2-trifluoroethylamino)phenyl)-3,5,5,6-tetramethyl-5,6-dihydropyrimidin-4(3H)-one

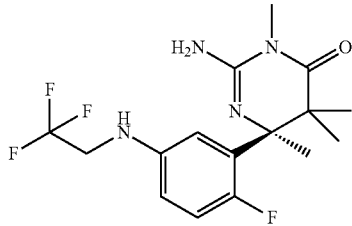 [SMILES: CN1C(=O)C(C)(C)[C@@](C)(c2cc(NCC(F)(F)F)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and trifluoro-acetaldehyde using decaborane yielded the title compound as a colorless waxy solid. MS (ESI): m/z=361.3 [M+H]+.

Example 76

(S)-2-Amino-6-{2-fluoro-5-[(tetrahydro-furan-3-ylmethyl)-amino]phenyl}-3,5,5,6-tetramethyl-5,6-dihydro-3H-pyrimidin-4-one

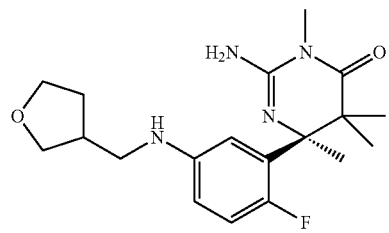 [SMILES: CN1C(=O)C(C)(C)[C@@](C)(c2cc(NCC3CCOC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and tetrahydro-furan-3-carbaldehyde using decaborane yielded a mixture of epimers of the title compound as a colorless waxy solid. MS (ESI): m/z=363.4 [M+H]+.

Example 77

(S)-2-Amino-6-{2-fluoro-5-[(2-methyl-3H-imidazol-4-ylmethyl)-amino]-phenyl}-3,5,5,6-tetramethyl-5,6-dihydro-3H-pyrimidin-4-one

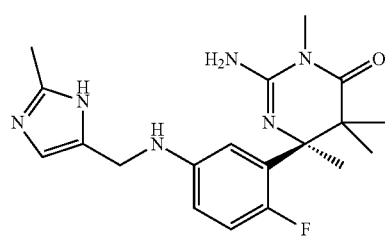 [SMILES: Cc1ncc(CNc2ccc(F)c([C@@]3(C)N=C(N)N(C)C(=O)C3(C)C)c2)[nH]1]

The reductive amination of (S)-2-amino-6-(5-amino-2-fluoro-phenyl)-3,5,5,6-tetramethyl-5,6-dihydro-3H-pyrimidin-4-one (intermediate J) and 2-methyl-3H-imidazole-4-carbaldehyde using decaborane yielded the title compound as a white solid. MS (ESI): m/z=373.2 [M+H]+.

Example 78

(S)-2-Amino-6-{2-fluoro-5-[(4-methyl-thiazol-5-ylmethyl)-amino]-phenyl}-3,5,5,6-tetramethyl-5,6-dihydro-3H-pyrimidin-4-one

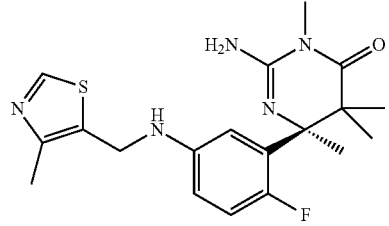 [SMILES: Cc1ncsc1CNc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and 4-methylthiazole-5-carbaldehyde using decaborane yielded the title compound as a white solid. MS (ESI): m/z=390.3 [M+H]+.

Example 79

(S)-2-Amino-6-(2-fluoro-5-(3-methoxyphenylamino)phenyl)-3,5,5,6-tetramethyl-5,6-dihydropyrimidin-4(3H)-one

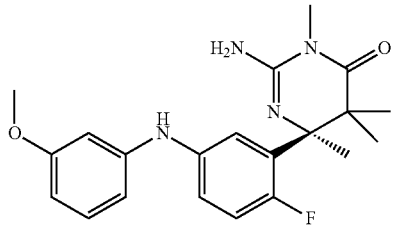 [SMILES: COc1cccc(Nc2ccc(F)c([C@@]3(C)N=C(N)N(C)C(=O)C3(C)C)c2)c1]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 3-methoxyphenylamine according to procedure A followed by deprotection yielded the title compound as an off white solid. MS (ESI): m/z=385.3 [M+H]$^+$.

Example 80

(S)-2-Amino-6-[2-fluoro-5-(1-pyrimidin-2-yl-ethylamino)-phenyl]-3,5,5,6-tetramethyl-5,6-dihydro-3H-pyrimidin-4-one

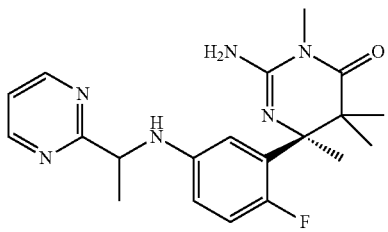 [SMILES: CC(Nc1ccc(F)c([C@@]2(C)N=C(N)N(C)C(=O)C2(C)C)c1)c1ncccn1]

The reductive amination of (S)-2-amino-6-(5-amino-2-fluoro-phenyl)-3,5,5,6-tetramethyl-5,6-dihydro-3H-pyrimidin-4-one (intermediate J) and 1-pyrimidin-2-yl-ethanone using decaborane yielded a mixture of epimers of the title compound as a yellow waxy solid. MS (ESI): m/z=385.2 [M+H]$^+$.

Example 81

(S)-2-Amino-6-(5-(2,4-difluorophenylamino)-2-fluorophenyl)-3,5,5,6-tetramethyl-5,6-dihydropyrimidin-4(3H)-one

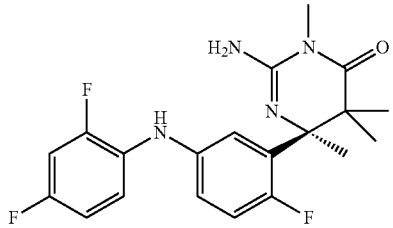 [SMILES: CN1C(=O)C(C)(C)[C@@](C)(c2cc(Nc3ccc(F)cc3F)ccc2F)N=C1N]

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 2,4-difluorophenylamine according to procedure A followed by deprotection yielded the title compound as a white solid. MS (ESI): m/z=391.2 [M+H]$^+$.

Example 82

(S)-2-Amino-6-(2-fluoro-5-(4-fluoro-2-methoxyphenylamino)phenyl)-3,5,5,6-tetramethyl-5,6-dihydropyrimidin-4(3H)-one

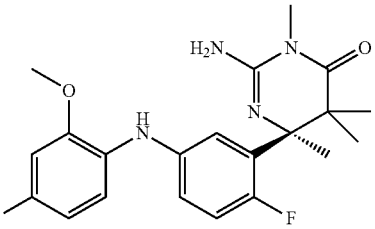

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 4-fluoro-2-methoxyphenylamine according to procedure A followed by deprotection yielded the title compound as a white solid. MS (ESI): m/z=403.4 [M+H]$^+$.

Example 83

(S)-2-Amino-6-[2-fluoro-5-(3,3,3-trifluoro-2-methyl-propylamino)-phenyl]-3,5,5,6-tetramethyl-5,6-dihydro-3H-pyrimidin-4-one

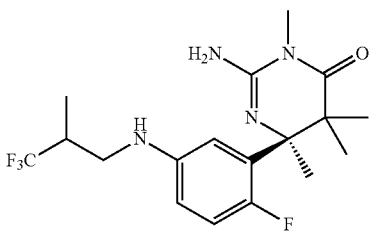 [SMILES: CC(CNc1ccc(F)c([C@@]2(C)N=C(N)N(C)C(=O)C2(C)C)c1)C(F)(F)F]

The reductive amination of (S)-2-amino-6-(5-amino-2-fluoro-phenyl)-3,5,5,6-tetramethyl-5,6-dihydro-3H-pyrimidin-4-one (intermediate J) and rac-3,3,3-trifluoro-2-methyl-propionaldehyde yielded a mixture of epimers of the title compound as a pale yellow oil. MS (ESI): m/z=389.3 [M+H]$^+$.

Example 84

(S)-2-Amino-6-(2-fluoro-5-(5-fluoro-2-methoxyphenylamino)phenyl)-3,5,5,6-tetramethyl-5,6-dihydropyrimidin-4(3H)-one

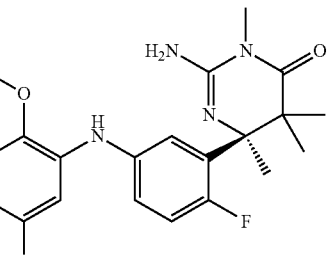

The coupling of [(S)-4-(5-bromo-2-fluoro-phenyl)-1,4,5,5-tetramethyl-6-oxo-1,4,5,6-tetrahydro-pyrimidin-2-yl]-carbamic acid tert-butyl ester (intermediate E8) and 5-fluoro-2-methoxyphenylamine according to procedure A followed by deprotection yielded the title compound as a white solid. MS (ESI): m/z=403.4 [M+H]$^+$.

Example 85

(S)-2-Amino-6-{2-fluoro-5-[(pyrimidin-2-ylmethyl)-amino]-phenyl}-3,5,5,6-tetramethyl-5,6-dihydro-3H-pyrimidin-4-one

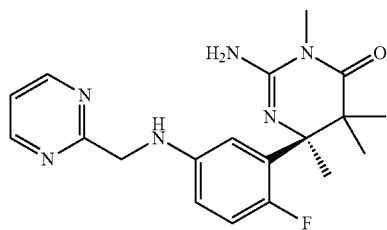 [SMILES: CN1C(=O)C(C)(C)[C@@](C)(c2cc(NCc3ncccn3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and pyrimidin-2-carbaldehyde using decaborane yielded the title compound as a white foam. MS (ESI): m/z=371.3 [M+H]$^+$.

Example 86

(S)-2-Amino-6-{2-fluoro-5-[(isoxazol-3-ylmethyl)-amino]phenyl}-3,5,5,6-tetramethyl-5,6-dihydro-3H-pyrimidin-4-one

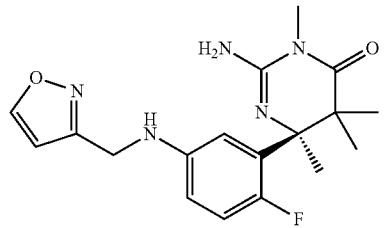 [SMILES: CN1C(=O)C(C)(C)[C@@](C)(c2cc(NCc3ccon3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and isoxazole-3-carbaldehyde using decaborane yielded the title compound as a light yellow waxy solid. MS (ESI): m/z=360.4 [M+H]$^+$.

Example 87

(S)-2-Amino-6-{2-fluoro-5-[(1-trifluoromethyl-cyclopropylmethyl)-amino]-phenyl}-3,5,5,6-tetramethyl-5,6-dihydro-3H-pyrimidin-4-one

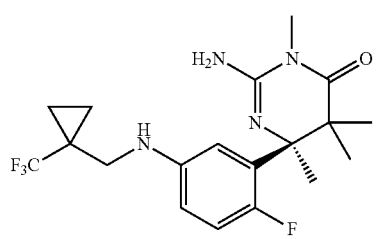 [SMILES: CN1C(=O)C(C)(C)[C@@](C)(c2cc(NCC3(C(F)(F)F)CC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-trifluoromethyl-cyclopropanecarbaldehyde (prepared according to Cotten, J. J. et al., International patent application WO 2009/005677) yielded a mixture of isomers of the title compound as a colorless solid. MS (ESI): m/z=401.4 [M+H]$^+$.

Example 88

(S)-2-Amino-6-[2-fluoro-5-(3-fluoro-phenylamino)-phenyl]-3,5,5,6-tetramethyl-5,6-dihydro-3H-pyrimidin-4-one

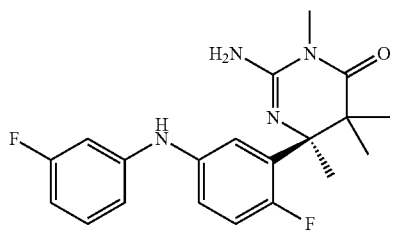 [SMILES: CN1C(=O)C(C)(C)[C@@](C)(c2cc(Nc3cccc(F)c3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 3-fluorophenylamine according to procedure A yielded the title compound as an off white solid. MS (ESI): m/z=373.3 [M+H]$^+$.

Example 89

(S)-2-Amino-6-[2-fluoro-5-(4-fluoro-phenylamino)-phenyl]-3,5,5,6-tetramethyl-5,6-dihydro-3H-pyrimidin-4-one

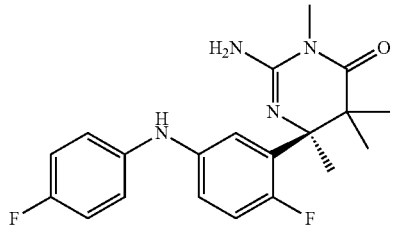 [SMILES: CN1C(=O)C(C)(C)[C@@](C)(c2cc(Nc3ccc(F)cc3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-fluoro-phenylamine according to procedure A yielded the title compound as an off white solid. MS (ESI): m/z=373.2 [M+H]$^+$.

Example 90

(S)-2-Amino-6-{2-fluoro-5-[(tetrahydro-pyran-3-ylmethyl)-amino]-phenyl}-3,5,5,6-tetramethyl-5,6-dihydro-3H-pyrimidin-4-one

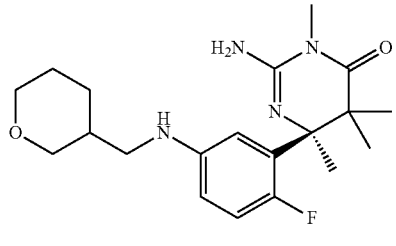 [SMILES: CN1C(=O)C(C)(C)[C@@](C)(c2cc(NCC3CCCOC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and tetrahydro-pyran-3-carbaldehyde yielded a mixture of epimers of the title compound as a white solid. MS (ESI): m/z=377.4 [M+H]$^+$.

Example 91

(S)-2-Amino-6-(5-ethylamino-2-fluoro-phenyl)-3,5,5,6-tetramethyl-5,6-dihydro-3H-pyrimidin-4-one

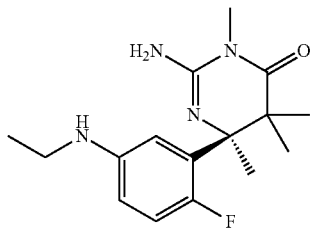 [SMILES: CCNc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and acetaldehyde yielded the title compound as a white waxy solid. MS (ESI): m/z=307.4 [M+H]⁺.

Example 92

(S)-2-Amino-6-(2-fluoro-5-((1S,2S)-2-hydroxycyclopentylamino)phenyl)-3,5,5,6-tetramethyl-5,6-dihydropyrimidin-4(3H)-one

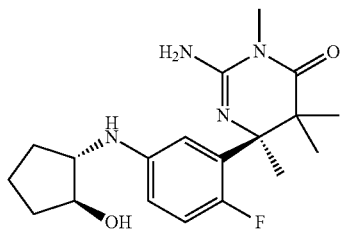 [SMILES: CN1C(=O)C(C)(C)[C@@](C)(c2cc(N[C@H]3CCC[C@@H]3O)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and (1S,2S)-2-amino-cyclopentanol according to procedure B yielded the title compound as a pale brown waxy solid. MS (ESI): m/z=363.4 [M+H]⁺.

Example 93

Acetic acid 5-[3-((S)-2-amino-1,4,5,5-tetramethyl-6-oxo-1,4,5,6-tetrahydro-pyrimidin-4-yl)-4-fluoro-phenylamino]-bicyclo[2.2.1]hept-2-yl ester

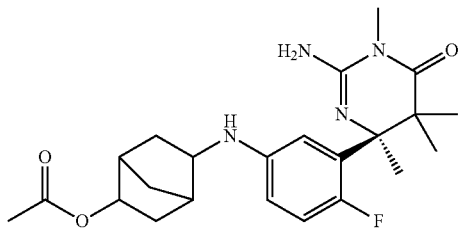 [SMILES: CC(=O)OC1CC2CC1CC2Nc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and rac-acetic acid 5-oxo-bicyclo[2.2.1]hept-2-yl ester (prepared as in J. Meinwald et al., *Tetrahedron* 1962, 18, 815-820) using decaborane yielded a mixture of isomers of the title compound as a white foam. MS (ESI): m/z=431.4 [M+H]⁺.

Example 94

(S)-2-Amino-6-[2-fluoro-5-(2-methoxy-(4-trifluoromethyl)-phenylamino)-phenyl]-3,5,5,6-tetramethyl-5,6-dihydro-3H-pyrimidin-4-one

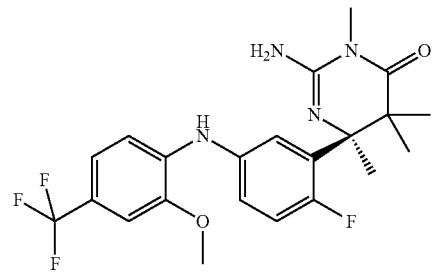 [SMILES: COc1cc(C(F)(F)F)ccc1Nc1ccc(F)c([C@@]2(C)N=C(N)N(C)C(=O)C2(C)C)c1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2-methoxy-4-trifluoromethyl-phenylamine according to procedure A yielded the title compound as an off white solid. MS (ESI): m/z=453.2 [M+H]⁺.

Example 95

{3-[3-((S)-2-Amino-1,4,5,5-tetramethyl-6-oxo-1,4,5,6-tetrahydro-pyrimidin-4-yl)-4-fluoro-phenylamino]-cyclopentyl}-acetic acid methyl ester

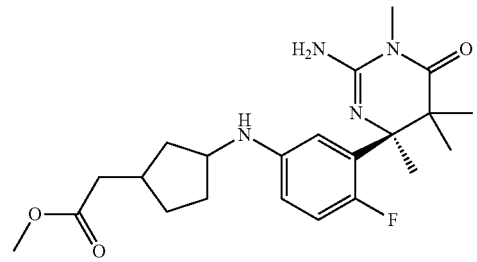

The reductive amination of (S)-2-amino-6-(5-amino-2-fluoro-phenyl)-3,5,5,6-tetramethyl-5,6-dihydro-3H-pyrimidin-4-one (intermediate J) and (3-oxo-cyclopentyl)-acetic acid methyl ester using decaborane yielded a mixture of isomers of the title compound as a white foam. MS (ESI): m/z=419.3 [M+H]⁺.

Example 96

(S)-2-Amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one

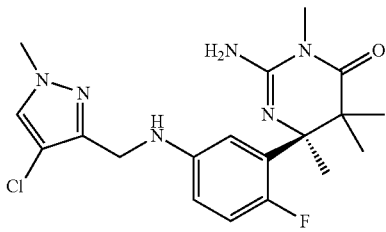 [SMILES: CN1C(=O)C(C)(C)[C@@](C)(c2cc(NCc3nn(C)cc3Cl)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 4-chloro-1-methyl-1H-pyrazole-3-carbaldehyde yielded the title compound as a colorless solid. MS (ESI): m/z=407.4 [M+H]$^+$.

Example 97

(S)-2-Amino-6-{2-fluoro-5-[((1R,2R)-2-phenyl-cyclopropylmethyl)-amino]-phenyl}-3,5,5,6-tetramethyl-5,6-dihydro-3H-pyrimidin-4-one

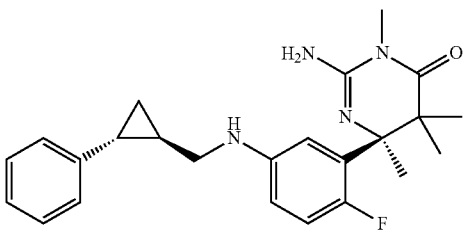 [SMILES: CN1C(=O)C(C)(C)[C@@](C)(c2cc(NC[C@@H]3C[C@H]3c3ccccc3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and (1R,2R)-2-phenyl-cyclopropane-carboxaldehyde yielded the title compound as a colorless solid. MS (ESI): m/z=409.4 [M+H]$^+$.

Example 98

{3-[3-((S)-2-Amino-1,4,5,5-tetramethyl-6-oxo-1,4,5,6-tetrahydro-pyrimidin-4-yl)-4-fluoro-phenylamino]-2,2-dimethyl-cyclopentyl}-acetic acid ethyl ester

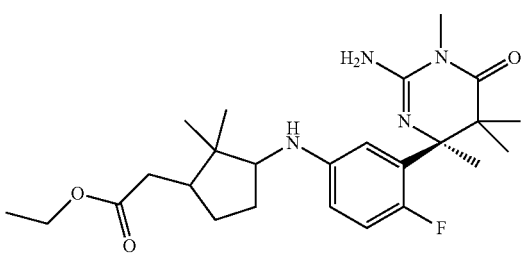 [SMILES: CCOC(=O)CC1CCC(Nc2ccc(F)c([C@@]3(C)N=C(N)N(C)C(=O)C3(C)C)c2)C1(C)C]

The reductive amination of (S)-2-amino-6-(5-amino-2-fluoro-phenyl)-3,5,5,6-tetramethyl-5,6-dihydro-3H-pyrimidin-4-one (intermediate J) and rac-(2,2-dimethyl-3-oxo-cyclopentyl)-acetic acid ethyl ester (prepared according to Bunce, R. A. et al., J. Org. Chem. 1995, 60(9), 2748) using decaborane yielded a mixture of isomers of the title compound as a white foam. MS (ESI): m/z=461.3 [M+H]$^+$.

Example 99

(S)-2-Amino-6-[2-fluoro-5-(1-methyl-1H-pyrazol-3-ylamino)-phenyl]-3,5,5,6-tetramethyl-5,6-dihydro-3H-pyrimidin-4-one

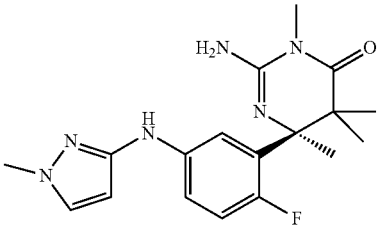

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 1-methyl-1H-pyrazol-3-ylamine according to procedure B yielded the title compound as an colorless waxy solid. MS (ESI): m/z=359.2 [M+H]$^+$.

Example 100

(1S,3R,5R,6S)-ethyl 2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylate

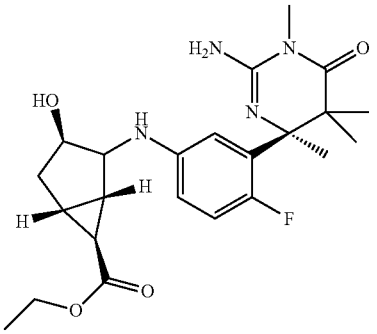 [SMILES: CCOC(=O)[C@H]1[C@@H]2C[C@@H](O)C(Nc3ccc(F)c([C@@]4(C)N=C(N)N(C)C(=O)C4(C)C)c3)[C@@H]21]

(1RS,5SR,6RS)-2-Oxo-bicyclo[3,1,0]hexane-6-carboxylic acid ethyl ester

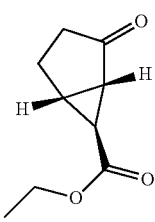

To a suspension of (ethoxycarbonylmethyl)dimethylsulfonium bromide (148.5 g, 0.648 mole) in acetonitrile (1170 ml) was added 1,8-diazabicyclo[5.4.0]undec-7-ene (97 ml, 0.648 mole) at 22° C. and stirring was continued for 45 min. The solution was treated with 2-cyclopenten-1-one (63 ml, 0.778 mole) and stirring was continued at 22° C. and light exclusion for 4 d. The mixture was evaporated to a volume of ca. 500 ml, partitioned between 1N aqueous HCl and diethylether, the organic layer was dried, evaporated and purified over silica (150 g) using cyclohexane/AcOEt (9:1). The material was dissolved in diethylether (50 ml) and n-pentane (50 ml), briefly cooled to −78° C. until the material precipitated, filtered and the residue was dried to give the title compound as white crystals.

(1RS,5SR,6RS)-2-(tert-Butyl-dimethyl-silanyloxy)-bicyclo[3.1.0]hex-2-ene-6-carboxylic acid ethyl ester

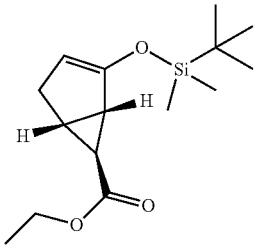 [SMILES: CCOC(=O)[C@H]1[C@@H]2CC=C(O[Si](C)(C)C(C)(C)C)[C@@H]21]

To a solution of (1RS,5SR,6RS)-2-oxo-bicyclo[3,1,0]hexane-6-carboxylic acid ethyl ester (28.93 g, 172 mmole) in dichloromethane (430 ml) was added at 22° C. NEt₃ (36.0 ml, 258 mmole), the mixture was cooled to 0° C. and treated with tert-butyldimethylsilyl triflate (43.5 ml, 189.2 mmole) keeping the temperature below 10° C. The mixture was allowed to warm to 22° C. over 2 h, washed with saturated aqueous NaHCO₃, the organic layer was dried, evaporated and the residue purified over aluminiumoxide (100 g) using cyclohexane/AcOEt (9:1) to give the title compound as a yellow oil which was used without further purification in the next step.

(1SR,3RS,5RS,6SR)-3-Hydroxy-2-oxo-bicyclo[3.1.0]hexane-6-carboxylic acid ethyl ester

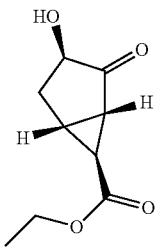

To a solution of (1RS,5SR,6RS)-2-(tert-butyl-dimethylsilanyloxy)-bicyclo[3.1.0]hex-2-ene-6-carboxylic acid ethyl ester (172 mmole) in MeOH (900 ml) was subsequently added NaHCO₃ (33.25 g) and magnesium-monoperoxyphthalate (104.5 g) and stirring was continued at ambient temperature for 1 h. The mixture was filtered, the filtrate evaporated and the residue partitioned between saturated NaHCO₃ (until gas evolution ceased) and dichloromethane. The organic layer was dried, evaporated and the residue dissolved in MeOH (750 ml). To the solution was subsequently added water (65 ml) and p-toluenesulfonic acid hydrate (3.44 g) and the mixture was stirred at 22° C. for 18 h. The mixture was evaporated, the residue partitioned between saturated NaHCO₃ and dichloromethane, the organic layer was dried, evaporated and the residue dissolved in diethylether (350 ml) at reflux temperature. The solution was treated with n-pentane until the solution became cloudy, the mixture was slowly cooled to 0° C. and stirring was continued at 0° C. for 2 h. The suspension was filtered, and the residue dried to give the title compound (15.0 g) as white crystals.

The reductive amination of (S)-2-amino-6-(5-amino-2-fluoro-phenyl)-3,5,5,6-tetramethyl-5,6-dihydro-3H-pyrimidin-4-one (intermediate J) and (1SR,3RS,5RS,6SR)-3-hydroxy-2-oxo-bicyclo[3.1.0]hexane-6-carboxylic acid ethyl ester using decaborane yielded a mixture of isomers of the title compound as a colorless waxy solid. MS (ESI): m/z=447.3 [M+H]⁺

Example 101

(6S)-2-Amino-6-(2-fluoro-5-(5-hydroxybicyclo[2.2.1]heptan-2-ylamino)phenyl)-3,5,5,6-tetramethyl-5,6-dihydropyrimidin-4(3H)-one

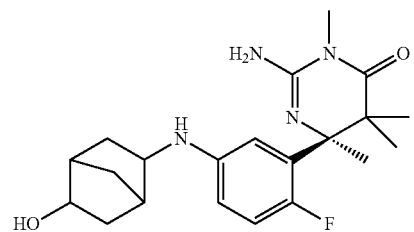 [SMILES: CN1C(=O)C(C)(C)[C@@](C)(c2cc(NC3CC4CC3CC4O)ccc2F)N=C1N]

To a solution of acetic acid 5-[3-((S)-2-amino-1,4,5,5-tetramethyl-6-oxo-1,4,5,6-tetrahydro-pyrimidin-4-yl)-4-fluoro-phenylamino]-bicyclo[2.2.1]hept-2-yl ester (example 93, 0.05 mmole) in THF (1 ml), MeOH (0.3 ml) and H₂O (0.3 ml) was added LiOH 1N (0.1 mmole) and the reaction mixture was stirred at room temperature for 4 h. The mixture was concentrated in vacuo, the residue dissolved in aqueous HCl (0.5N) until pH=5 and washed with EtOAc. The aqueous phase was basified to pH=8 with a saturated aqueous NaHCO₃ solution and extracted with EtOAc. The organic phase was separated, dried over Na₂SO₄ and evaporated to yield a mixture of isomers of the title compound as a colorless waxy solid. MS (ESI): m/z=389.3 [M+H]⁺.

Example 102

(S)-2-Amino-6-[5-(4,5-difluoro-2-methoxy-phenylamino)-2-fluoro-phenyl]-3,5,5,6-tetramethyl-5,6-dihydro-3H-pyrimidin-4-one

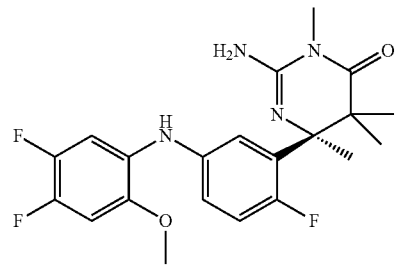 [SMILES: COc1cc(F)c(F)cc1Nc1ccc(F)c([C@@]2(C)N=C(N)N(C)C(=O)C2(C)C)c1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4,5-difluoro-2-methoxy-phenylamine according to procedure A yielded the title compound as an white solid. MS (ESI): m/z=421.2 [M+H]⁺.

Example 103

(S)-2-(3-(2-Amino-1,4,5,5-tetramethyl-6-oxo-1,4,5,6-tetrahydropyrimidin-4-yl)-4-fluorophenylamino)benzonitrile

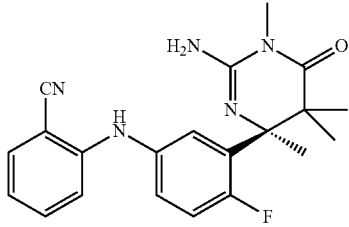 [SMILES: CN1C(=O)C(C)(C)[C@@](C)(c2cc(Nc3ccccc3C#N)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2-aminobenzonitrile according to procedure B yielded the title compound as an off-white solid. MS (ESI): m/z=380.3 [M+H]+.

Example 104

(S)-2-Amino-6-{2-fluoro-5-[(5-methyl-isoxazol-3-ylmethyl)-amino]-phenyl}-3,5,5,6-tetramethyl-5,6-dihydro-3H-pyrimidin-4-one

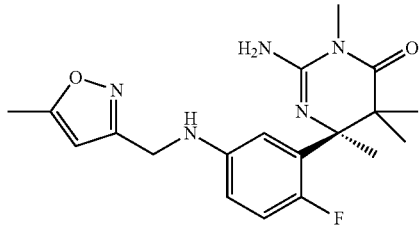

The reductive amination of (S)-2-amino-6-(5-amino-2-fluoro-phenyl)-3,5,5,6-tetramethyl-5,6-dihydro-3H-pyrimidin-4-one (intermediate J) and 5-methyl-isoxazole-3-carbaldehyde yielded the title compound as a colorless solid. MS (ESI): m/z=374.3 [M+H]+.

Example 105

(S)-2-Amino-6-(2-fluoro-5-(pyridin-2-ylamino)phenyl)-3,5,5,6-tetramethyl-5,6-dihydropyrimidin-4(3H)-one

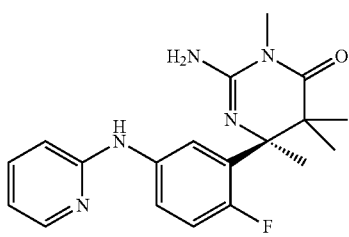 [SMILES: CN1C(=O)C(C)(C)[C@@](C)(c2cc(Nc3ccccn3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2-aminopyridine according to procedure B yielded the title compound as an off-white solid. MS (ESI): m/z=356.2 [M+H]+.

Example 106

(6S)-2-Amino-6-(5-(3,3-dimethyl-2,3-dihydro-1H-inden-1-ylamino)-2-fluorophenyl)-3,5,5,6-tetramethyl-5,6-dihydropyrimidin-4(3H)-one

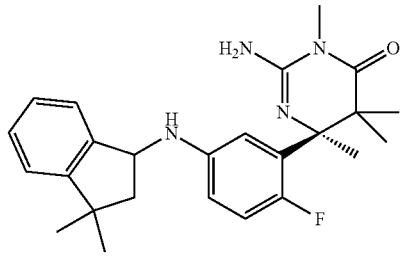 [SMILES: CN1C(=O)C(C)(C)[C@@](C)(c2cc(NC3CC(C)(C)c4ccccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 3,3-dimethyl-indan-1-one using decaborane yielded a mixture of epimers of the title compound as a white foam. MS (ESI): m/z=423.3 [M+H]+.

Example 107

(S)-2-Amino-6-(5-(1-benzyl-1H-pyrazol-5-ylamino)-2-fluorophenyl)-3,5,5,6-tetramethyl-5,6-dihydropyrimidin-4(3H)-one

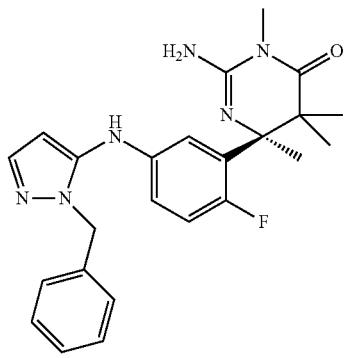 [SMILES: CN1C(=O)C(C)(C)[C@@](C)(c2cc(Nc3ccnn3Cc3ccccc3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 1-benzyl-1H-pyrazol-5-ylamine according to procedure B yielded the title compound as an light red solid. MS (ESI): m/z=435.4 [M+H]+.

Example 108

(S)-2-Amino-6-(5-(2,4-dimethoxyphenylamino)-2-fluorophenyl)-3,5,5,6-tetramethyl-5,6-dihydropyrimidin-4(3H)-one

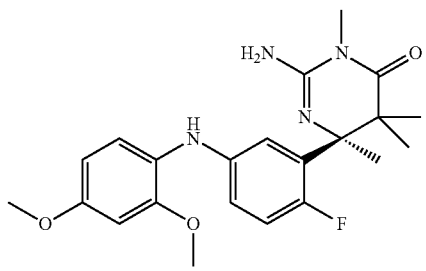

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,4-dimethoxyphenylamine according to procedure A yielded the title compound as an light red oil. MS (ESI): m/z=415.4 [M+H]+.

Example 109

(S)-2-Amino-6-{2-fluoro-5-[(2-methyl-oxazol-4-ylmethyl)-amino]-phenyl}-3,5,5,6-tetramethyl-5,6-dihydro-3H-pyrimidin-4-one

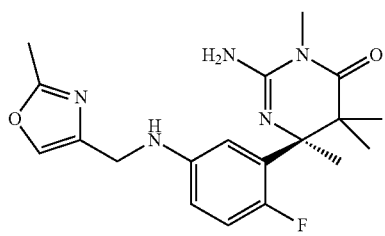 [SMILES: Cc1nc(CNc2ccc(F)c([C@@]3(C)N=C(N)N(C)C(=O)C3(C)C)c2)co1]

The reductive amination of (S)-2-amino-6-(5-amino-2-fluoro-phenyl)-3,5,5,6-tetramethyl-5,6-dihydro-3H-pyrimidin-4-one (intermediate J) and 2-methyl-oxazole-4-carbaldehyde yielded the title compound as a colorless solid. MS (ESI): m/z=374.3 [M+H]⁺.

Example 110

(S)-2-Amino-6-{2-fluoro-5-[(4-methyl-2H-pyrazol-3-ylmethyl)-amino]-phenyl}-3,5,5,6-tetramethyl-5,6-dihydro-3H-pyrimidin-4-one

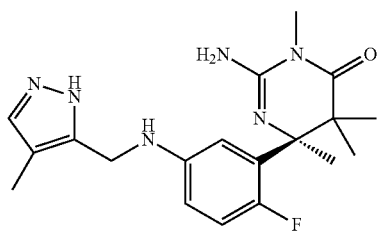 [SMILES: Cc1cn[nH]c1CNc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and 4-methyl-2H-pyrazole-3-carbaldehyde yielded the title compound as a colorless solid. MS (ESI): m/z=373.3 [M+H]⁺.

Example 111

(S)-2-Amino-6-{2-fluoro-5-[1-(2H-pyrazol-3-yl)-ethylamino]-phenyl}-3,5,5,6-tetramethyl-5,6-dihydro-3H-pyrimidin-4-one

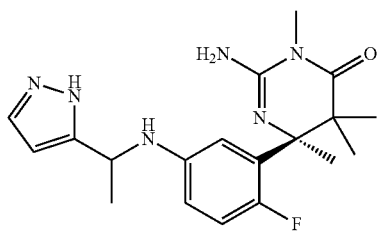 [SMILES: CC(Nc1ccc(F)c([C@@]2(C)N=C(N)N(C)C(=O)C2(C)C)c1)c1ccn[nH]1]

The reductive amination of (S)-2-amino-6-(5-amino-2-fluoro-phenyl)-3,5,5,6-tetramethyl-5,6-dihydro-3H-pyrimidin-4-one (intermediate J) and 1-(2H-pyrazol-3-yl)-ethanone yielded a mixture of epimers of the title compound as a colorless solid. MS (ESI): m/z=373.3 [M+H]⁺.

Example 112

(6S)-2-Amino-6-(5-(5-chloro-3,3-dimethyl-2,3-dihydro-1H-inden-1-ylamino)-2-fluorophenyl)-3,5,5,6-tetramethyl-5,6-dihydropyrimidin-4(3H)-one

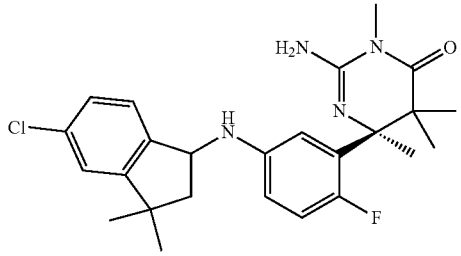 [SMILES: CN1C(=O)C(C)(C)[C@@](C)(c2cc(NC3CC(C)(C)c4cc(Cl)ccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 5-chloro-3,3-dimethyl-indan-1-one (prepared according to Claiborne, C. F. et al., Int. patent application WO 2008/019124) using decaborane yielded a mixture of epimers of the title compound as a colorless waxy solid. MS (ESI): m/z=457.4 [M+H]⁺.

Example 113

(S)-2-Amino-6-[5-(3-ethyl-indan-1-ylamino)-2-fluoro-phenyl]-3,5,5,6-tetramethyl-5,6-dihydro-3H-pyrimidin-4-one

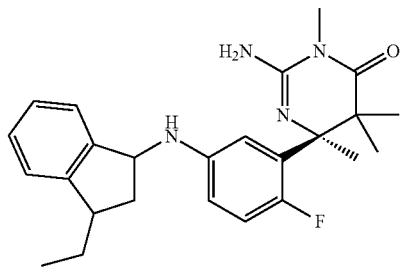 [SMILES: CCC1CC(Nc2ccc(F)c([C@@]3(C)N=C(N)N(C)C(=O)C3(C)C)c2)c2ccccc21]

The reductive amination of (S)-2-amino-6-(5-amino-2-fluoro-phenyl)-3,5,5,6-tetramethyl-5,6-dihydro-3H-pyrimidin-4-one (intermediate J) and rac-3-ethyl-indan-1-one (prepared according to Kousik K., J. Am. Chem. Soc. 2005, 127, 16042) using decaborane yielded a mixture of isomers of the title compound as a white solid. MS (ESI): m/z=423.3 [M+H]⁺.

Example 114

(6S)-2-Amino-6-(2-fluoro-5-(5-fluoro-2-methyl-2,3-dihydro-1H-inden-1-ylamino)phenyl)-3,5,5,6-tetramethyl-5,6-dihydropyrimidin-4(3H)-one

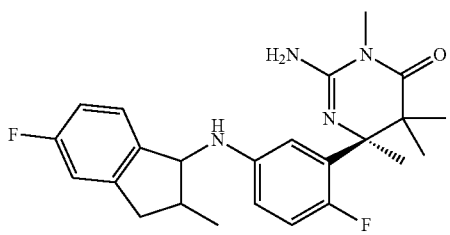 [SMILES: CC1Cc2cc(F)ccc2C1Nc1ccc(F)c([C@@]2(C)N=C(N)N(C)C(=O)C2(C)C)c1]

The reductive amination of (S)-2-amino-6-(5-amino-2-fluoro-phenyl)-3,5,5,6-tetramethyl-5,6-dihydro-3H-pyrimidin-4-one (intermediate J) and rac-5-fluoro-2-methyl-indan-1-one using decaborane yielded a mixture of isomers of the title compound as a white solid. MS (ESI): m/z=427.3 [M+H]⁺.

Example 115

2-(3-(3-((S)-2-Amino-1,4,5,5-tetramethyl-6-oxo-1,4,5,6-tetrahydropyrimidin-4-yl)-4-fluorophenylamino)cyclopentyl)acetic acid

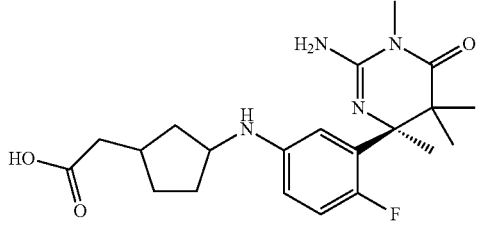 [SMILES: CN1C(=O)C(C)(C)[C@@](C)(c2cc(NC3CCC(CC(=O)O)C3)ccc2F)N=C1N]

To a solution of {3-[3-((S)-2-amino-1,4,5,5-tetramethyl-6-oxo-1,4,5,6-tetrahydro-pyrimidin-4-yl)-4-fluoro-phenylamino]-cyclopentyl}-acetic acid methyl ester (example 95, 0.05 mmol) in THF (1 ml), MeOH (0.3 ml), and H$_2$O (0.3 ml) was added LiOH (1N, 0.1 mmol) and the reaction mixture was stirred at room temperature for 4 h. The mixture was concentrated in vacuo and the residue diluted with aqueous HCl (0.5N) until pH=5 and EtOAc. The white solid which precipitate was filtered off, washed with H2O and dried. The organic phase was dried over Na$_2$SO$_4$ and evaporated to yield a white solid. The combined solid material was triturated with a mixture of dichloromethane and MeOH (10:1), filtered and the filtrate was concentrated in vacuo to yield a mixture of isomers of the title compound as a white solid. MS (ESI): m/z=405.5 [M+H]$^+$.

Example 116

2-(3-(3-((S)-2-Amino-1,4,5,5-tetramethyl-6-oxo-1,4,5,6-tetrahydropyrimidin-4-yl)-4-fluorophenylamino)-2,2-dimethylcyclopentyl)acetic acid

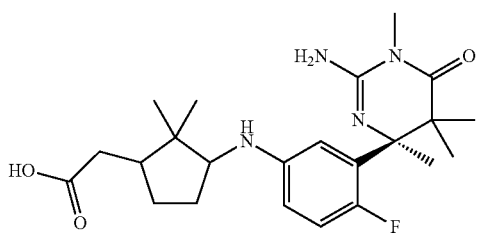 [SMILES: CN1C(=O)C(C)(C)[C@@](C)(c2cc(NC3CCC(CC(=O)O)C3(C)C)ccc2F)N=C1N]

To a solution of {3-[3-((S)-2-amino-1,4,5,5-tetramethyl-6-oxo-1,4,5,6-tetrahydro-pyrimidin-4-yl)-4-fluoro-phenylamino]-2,2-dimethyl-cyclopentyl}-acetic acid ethyl ester (example 98, 0.05 mmole) in THF (1 ml), MeOH (0.3 ml) and H$_2$O (0.3 ml) was added LiOH (1N, 0.1 mmole) and the reaction mixture was stirred at room temperature for 4 h. The mixture was concentrated in vacuo, the residue was diluted with aqueous HCl (0.5N) until pH=5 and washed with EtOAc. The aqueous phase was basified to pH=8 with a saturated aqueous NaHCO$_3$ solution and extracted with EtOAc. The organic phase was dried over Na$_2$SO$_4$ and evaporated to yield a mixture of isomers of the title compound as a white solid. MS (ESI): m/z=433.5 [M+H]$^+$.

Example 117

(1S,3R,5R,6S)-2-(3-((S)-2-amino-1,4,5,5-tetramethyl-6-oxo-1,4,5,6-tetrahydropyrimidin-4-yl)-4-fluorophenylamino)-3-hydroxybicyclo[3.1.0]hexane-6-carboxylic acid

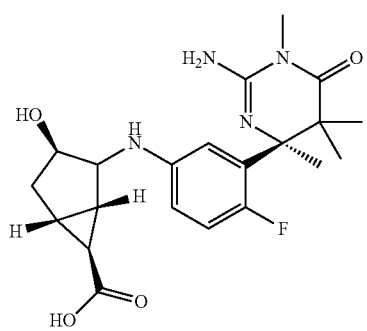 [SMILES: CN1C(=O)C(C)(C)[C@@](C)(c2cc(NC3[C@H]4[C@@H](C[C@H]3O)[C@@H]4C(=O)O)ccc2F)N=C1N]

To a solution of (1S,3R,5R,6S)-2-[3-((S)-2-Amino-1,4,5,5-tetramethyl-6-oxo-1,4,5,6-tetrahydro-pyrimidin-4-yl)-4-fluoro-phenylamino]-3-hydroxy-bicyclo[3.1.0]hexane-6-carboxylic acid ethyl ester (example 100, 0.05 mmol) in THF (1 ml), MeOH (0.3 ml) and H$_2$O (0.3 ml) was added LiOH (1N, 0.1 mmol) and the reaction mixture was stirred at room temperature for 4 h. The mixture was concentrated in vacuo, the residue diluted with aqueous HCl (0.5 N) until pH=5 and evaporated again. The solid residue was triturated with dichloromethane/MeOH (10:1), filtered and the filtrate was concentrated in vacuo to yield a mixture of isomers of the title compound as a white solid. MS (ESI): m/z=419.3 [M+H]$^+$.

Example 118

(S)-2-Amino-6-(5-(5-chloro-2-methylphenylamino)-2-fluorophenyl)-3,5,5,6-tetramethyl-5,6-dihydropyrimidin-4(3H)-one

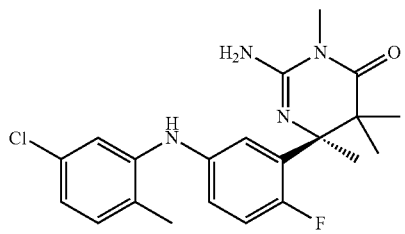 [SMILES: Cc1ccc(Cl)cc1Nc1ccc(F)c([C@@]2(C)N=C(N)N(C)C(=O)C2(C)C)c1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 5-chloro-2-methylphenylamine according to procedure A yielded the title compound as an off white solid. MS (ESI): m/z=403.2 [M+H]$^+$.

Example 119

(S)-2-Amino-6-(5-(2-chlorophenylamino)-2-fluorophenyl)-3,5,5,6-tetramethyl-5,6-dihydropyrimidin-4(3H)-one

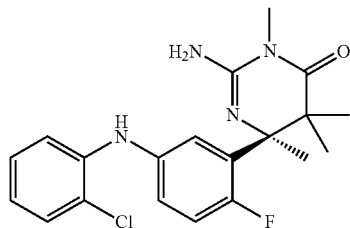 [SMILES: CN1C(=O)C(C)(C)[C@@](C)(c2cc(Nc3ccccc3Cl)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2-chlorophenylamine according to procedure A yielded the title compound as a pink solid. MS (ESI): m/z=389.3 [M+H]$^+$.

Example 120

(S)-2-Amino-6-[5-(2,5-dimethoxy-phenylamino)-2-fluoro-phenyl]-3,5,5,6-tetramethyl-5,6-dihydro-3H-pyrimidin-4-one

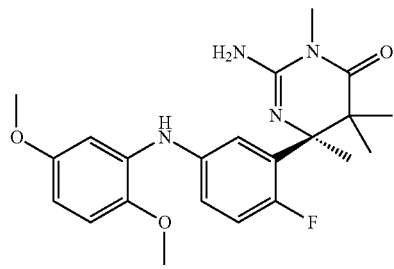 [SMILES: COc1ccc(OC)c(Nc2ccc(F)c([C@@]3(C)N=C(N)N(C)C(=O)C3(C)C)c2)c1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,5-dimethoxy-phenylamine according to procedure A yielded the title compound as an off white solid. MS (ESI): m/z=415.3 [M+H]$^+$.

Example 121

(S)-2-Amino-6-(2-fluoro-5-(2-methoxy-5-(trifluoromethyl)phenylamino)phenyl)-3,5,5,6-tetramethyl-5,6-dihydropyrimidin-4(3H)-one

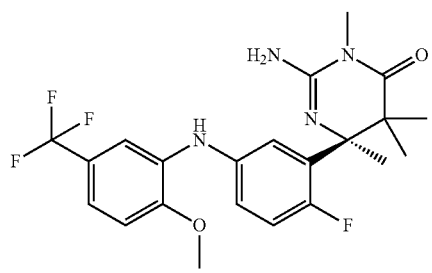

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2-methoxy-5-(trifluoromethyl)phenylamine according to procedure A yielded the title compound as an off white solid. MS (ESI): m/z=453.2 [M+H]$^+$.

Example 122

(S)-Methyl 3-(3-(2-amino-1,4,5,5-tetramethyl-6-oxo-1,4,5,6-tetrahydropyrimidin-4-yl)-4-fluorophenylamino)-4-methoxybenzoate

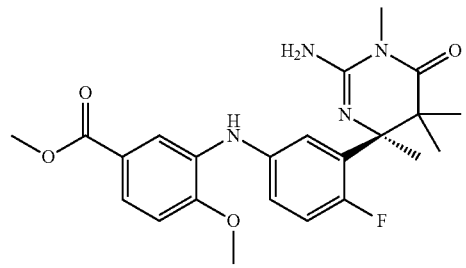

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 3-amino-4-methoxy-benzoic acid methyl ester according to procedure A yielded the title compound as a white solid. MS (ESI): m/z=443.4 [M+H]$^+$.

Example 123

(S)-Methyl-4-(3-(2-amino-1,4,5,5-tetramethyl-6-oxo-1,4,5,6-tetrahydropyrimidin-4-yl)-4-fluorophenylamino)-3-methoxybenzoate

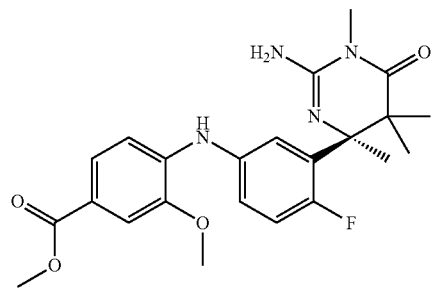 [SMILES: COC(=O)c1ccc(Nc2ccc(F)c([C@@]3(C)N=C(N)N(C)C(=O)C3(C)C)c2)c(OC)c1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-3-methoxy-benzoic acid methyl ester according to procedure A yielded the title compound as a white solid. MS (ESI): m/z=443.4 [M+H]$^+$.

Example 124

(S)-6-(5-(1H-Pyrazol-5-ylamino)-2-fluorophenyl)-2-amino-3,5,5,6-tetramethyl-5,6-dihydropyrimidin-4(3H)-one hydrochloride

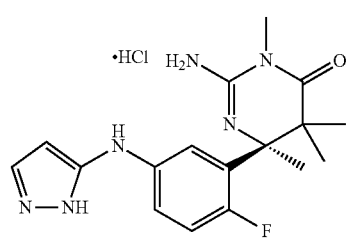 [SMILES: CN1C(=O)C(C)(C)[C@@](C)(c2cc(Nc3ccn[nH]3)ccc2F)N=C1N ; Cl]

To a solution of (S)-2-amino-6-(5-(1-benzyl-1H-pyrazol-5-ylamino)-2-fluorophenyl)-3,5,5,6-tetramethyl-5,6-dihydropyrimidin-4(3H)-one (example 107, 0.02 mmole) in methanol (1 ml) was added a solution of aqueous 4M HCl in 1,4-dioxane (0.25 ml) and Pd/C (10%, 3 mg) under argon. The reaction mixture was hydrogenated at 1 atm $H_2$ for 2 h, filtered over Decalite and the residue was washed with methanol. The filtrate was concentrated in vacuo and the residue purified by flash chromatography on $NH_2$-silica using a gradient of dichloromethane/methanol to yield the title compound as a colorless waxy solid. MS (ESI): m/z=345.2 $[M+H]^+$.

Example 125

(S)-2-Amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one

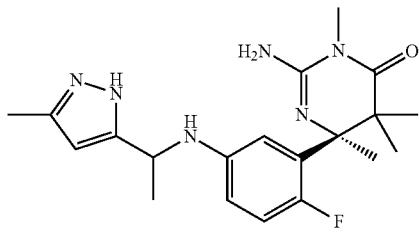

The reductive amination of (S)-2-amino-6-(5-amino-2-fluoro-phenyl)-3,5,5,6-tetramethyl-5,6-dihydro-3H-pyrimidin-4-one (intermediate J) and 1-(5-methyl-2H-pyrazol-3-yl)-ethanone with $NaBH_4$ yielded a mixture of epimers of the title compound as a colorless oil. MS (ESI): m/z=387.3 $[M+H]^+$.

Example 126

(S)-2-Amino-6-{5-[1-(4,5-dimethyl-thiazol-2-yl)-ethylamino]-2-fluoro-phenyl}-3,5,5,6-tetramethyl-5,6-dihydro-3H-pyrimidin-4-one

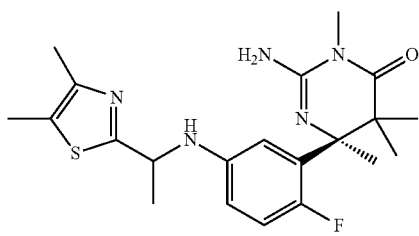

The reductive amination of (S)-2-amino-6-(5-amino-2-fluoro-phenyl)-3,5,5,6-tetramethyl-5,6-dihydro-3H-pyrimidin-4-one (intermediate J) and 1-(4,5-dimethyl-thiazol-2-yl)-ethanone with zinc-modified cyanoborohydride yielded a mixture of epimers of the title compound as a colorless solid. MS (ESI): m/z=418.4 $[M+H]^+$.

Example 127

(S)-2-Amino-6-[5-(1-benzothiazol-2-yl-ethylamino)-2-fluoro-phenyl]-3,5,5,6-tetramethyl-5,6-dihydro-3H-pyrimidin-4-one

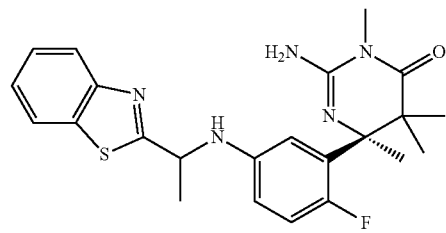 [SMILES: CC(Nc1ccc(F)c([C@@]2(C)N=C(N)N(C)C(=O)C2(C)C)c1)c1nc2ccccc2s1]

The reductive amination of (S)-2-amino-6-(5-amino-2-fluoro-phenyl)-3,5,5,6-tetramethyl-5,6-dihydro-3H-pyrimidin-4-one (intermediate J) and 1-benzothiazol-2-yl-ethanone with zinc-modified cyanoborohydride yielded a mixture of epimers of the title compound as a colorless solid. MS (ESI): m/z=440.4 $[M+H]^+$.

Example 128

(S)-2-Amino-6-{5-[(4-chloro-2H-pyrazol-3-ylmethyl)-amino]-2-fluoro-phenyl}-3,5,5,6-tetramethyl-5,6-dihydro-3H-pyrimidin-4-one

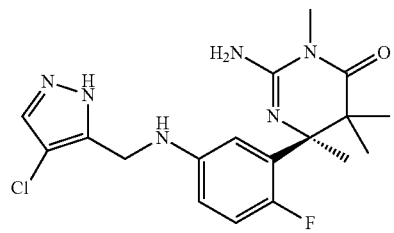 [SMILES: CN1C(=O)C(C)(C)[C@@](C)(c2cc(NCc3[nH]ncc3Cl)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 4-chloro-2H-pyrazole-3-carbaldehyde yielded the title compound as a colorless solid. MS (ESI): m/z=393.2 $[M+H]^+$.

Example 129

(S)-3-(3-(2-amino-1,4,5,5-tetramethyl-6-oxo-1,4,5,6-tetrahydropyrimidin-4-yl)-4-fluorophenylamino)-4-methoxybenzoic acid

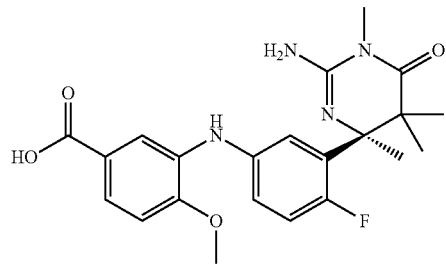 [SMILES: COc1ccc(C(=O)O)cc1Nc1ccc(F)c([C@@]2(C)N=C(N)N(C)C(=O)C2(C)C)c1]

To a solution of (S)-methyl-3-(3-(2-amino-1,4,5,5-tetramethyl-6-oxo-1,4,5,6-tetrahydropyrimidin-4-yl)-4-fluorophenylamino)-4-methoxybenzoate (example 122, 0.05 mmol) in THF (1 ml), MeOH (0.3 ml) and H₂O (0.3 ml) was added LiOH (1N, 0.1 mmole) and the reaction mixture was stirred at room temperature for 12 h. The mixture was concentrated in vacuo and the residue diluted with aqueous HCl (0.5N) until pH=5 and extracted with dichloromethane. The organic phase was dried, evaporated and the residue triturated with Et₂O to give the title compound as a white solid. MS (ESI): m/z=429.2 [M+H]⁺.

Example 130

(S)-4-(3-(2-Amino-1,4,5,5-tetramethyl-6-oxo-1,4,5,6-tetrahydropyrimidin-4-yl)-4-fluorophenylamino)-3-methoxybenzoic acid

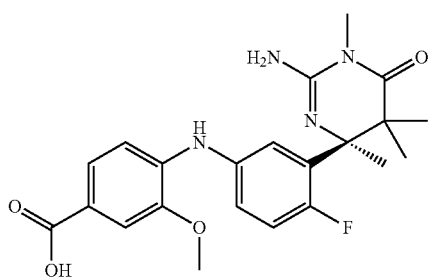 [SMILES: COc1cc(C(=O)O)ccc1Nc1ccc(F)c([C@@]2(C)N=C(N)N(C)C(=O)C2(C)C)c1]

To a solution of (S)-methyl 4-(3-(2-amino-1,4,5,5-tetramethyl-6-oxo-1,4,5,6-tetrahydropyrimidin-4-yl)-4-fluorophenylamino)-3-methoxybenzoate (example 123, 0.05 mmol) in THF (1 ml), MeOH (0.3 ml) and H₂O (0.3 ml) was added LiOH (1N, 0.1 mmole) and the reaction mixture was stirred at room temperature for 12 h. The mixture was concentrated in vacuo, the residue was dissolved in aqueous HCl (0.5N) until pH=5 and extracted with dichloromethane. The organic phase was separated, dried over Na₂SO₄ and evaporated to yield a white solid. The solid material was triturated with Et₂O, filtered and dried to yield the title compound as a white solid. MS (ESI): m/z=429.2 [M+H]⁺.

Example 131

(S)-2-Amino-6-{2-fluoro-5-[(3-methyl-oxetan-3-ylmethyl)-amino]-phenyl}-3,5,5,6-tetramethyl-5,6-dihydro-3H-pyrimidin-4-one

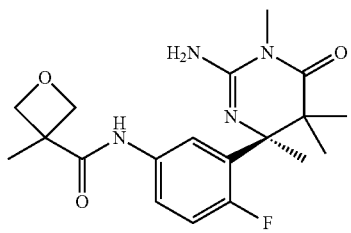

The coupling of (S)-2-amino-6-(5-amino-2-fluoro-phenyl)-3,5,5,6-tetramethyl-5,6-dihydro-3H-pyrimidin-4-one (intermediate J) and 3-methyl-oxetane-3-carboxylic acid yielded the title compound as a colorless solid. MS (ESI): m/z=377.4 [M+H]⁺.

Example 132

(S)-2-Amino-6-[2-fluoro-5-(oxetan-3-ylamino)-phenyl]-3,5,5,6-tetramethyl-5,6-dihydro-3H-pyrimidin-4-one

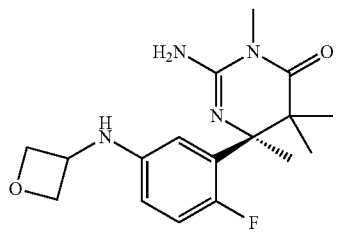 [SMILES: CN1C(=O)C(C)(C)[C@@](C)(c2cc(NC3COC3)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and oxetan-3-one yielded the title compound as a colorless oil. MS (ESI): m/z=335.4 [M+H]⁺.

Example 133

(S)-2-Amino-6-[5-(6-chloro-2,3-dihydro-benzofuran-3-ylamino)-2-fluoro-phenyl]-3,5,5,6-tetramethyl-5,6-dihydro-3H-pyrimidin-4-one

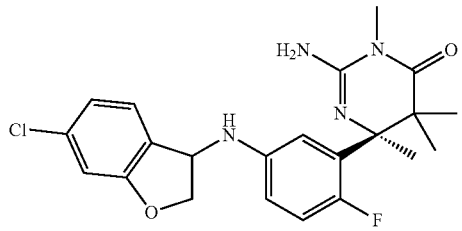 [SMILES: CN1C(=O)C(C)(C)[C@@](C)(c2cc(NC3COc4cc(Cl)ccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 6-chloro-benzofuran-3-one using decaborane yielded a mixture of epimers of the title compound as a white foam. MS (ESI): m/z=431.3 [M+H]⁺.

Example 134

1-Hydroxy-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide

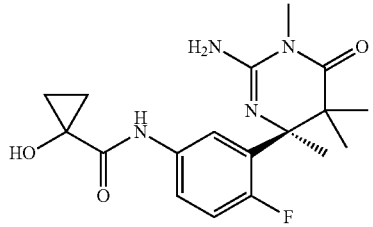 [SMILES: CN1C(=O)C(C)(C)[C@@](C)(c2cc(NC(=O)C3(O)CC3)ccc2F)N=C1N]

The coupling of (S)-2-amino-6-(5-amino-2-fluoro-phenyl)-3,5,5,6-tetramethyl-5,6-dihydro-3H-pyrimidin-4-one (intermediate J) and 1-hydroxy-cyclopropanecarboxylic acid yielded the title compound as a colorless solid. MS (ESI): m/z=363.4 [M+H]⁺.

Example 135

2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile

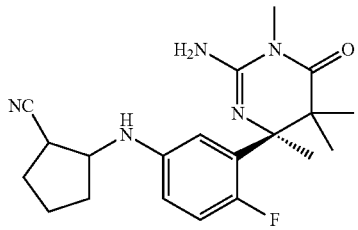 [SMILES: CN1C(=O)C(C)(C)[C@@](C)(c2cc(NC3CCCC3C#N)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and rac-2-oxo-cyclopentanecarbonitrile using decaborane yielded a mixture of epimers of the title compound as a white solid. MS (ESI): m/z=372.3 [M+H]$^+$.

Example 136

1-[3-((S)-2-Amino-1,4,5,5-tetramethyl-6-oxo-1,4,5,6-tetrahydro-pyrimidin-4-yl)-4-fluoro-phenylamino]-indan-4-carboxylic acid

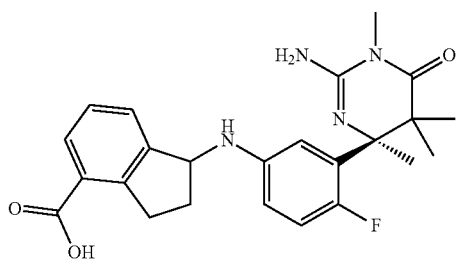 [SMILES: CN1C(=O)C(C)(C)[C@@](C)(c2cc(NC3CCc4c(C(=O)O)cccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 1-oxo-indan-4-carboxylic acid using decaborane yielded a mixture of epimers of the title compound as a light yellow foam. MS (ESI): m/z=439.3 [M+H]$^+$.

Example 137

(S)-6-[5-(1-Acetyl-6-fluoro-2,3-dihydro-1H-indol-3-ylamino)-2-fluoro-phenyl]-2-amino-3,5,5,6-tetramethyl-5,6-dihydro-3H-pyrimidin-4-one

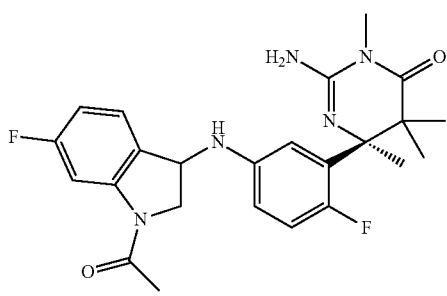 [SMILES: CC(=O)N1CC(Nc2ccc(F)c([C@@]3(C)N=C(N)N(C)C(=O)C3(C)C)c2)c2ccc(F)cc21]

The reductive amination of (S)-2-amino-6-(5-amino-2-fluoro-phenyl)-3,5,5,6-tetramethyl-5,6-dihydro-3H-pyrimidin-4-one (intermediate J) and 1-acetyl-6-fluoro-1,2-dihydro-indol-3-one using decaborane yielded a mixture of epimers of the title compound as a light red waxy solid. MS (ESI): m/z=456.4 [M+H]$^+$.

Example 138

(S)-2-Amino-6-(2-fluoro-5-(pyridin-3-ylamino)phenyl)-3,5,5,6-tetramethyl-5,6-dihydropyrimidin-4(3H)-one

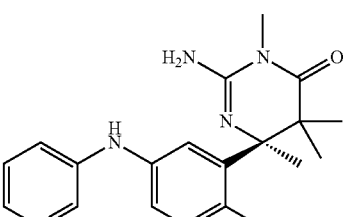

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 3-aminopyridine according to procedure B yielded the title compound as a light yellow gum. MS (ESI): m/z=356.4 [M+H]$^+$.

Example 139

N-[3-((S)-2-Amino-1,4,5,5-tetramethyl-6-oxo-1,4,5,6-tetrahydro-pyrimidin-4-yl)-4-fluoro-phenyl]-2-hydroxy-2-phenyl-propionamide

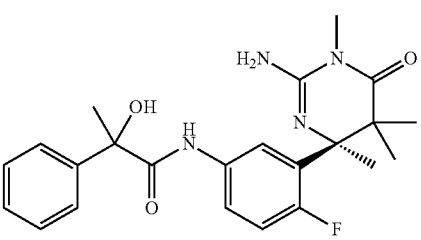 [SMILES: CN1C(=O)C(C)(C)[C@@](C)(c2cc(NC(=O)C(C)(O)c3ccccc3)ccc2F)N=C1N]

The coupling of (S)-2-amino-6-(5-amino-2-fluoro-phenyl)-3,5,5,6-tetramethyl-5,6-dihydro-3H-pyrimidin-4-one (intermediate J) and 2-hydroxy-2-phenyl-propionic acid yielded a mixture of epimers of the title compound as a white solid. MS (ESI): m/z=427.3 [M+H]$^+$.

Example 140

(S)-2-Amino-6-[2-fluoro-5-(7-fluoro-chroman-4-ylamino)-phenyl]-3,5,5,6-tetramethyl-5,6-dihydro-3H-pyrimidin-4-one

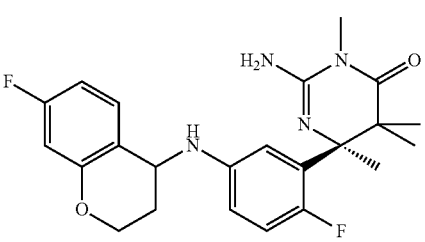 [SMILES: CN1C(=O)C(C)(C)[C@@](C)(c2cc(NC3CCOc4cc(F)ccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and 7-fluoro-chroman-4-one with decaborane yielded a mixture of epimers of the title compound as a white solid. MS (ESI): m/z=429.3 [M+H]$^+$.

Example 141

N-[3-((S)-2-Amino-1,4,5,5-tetramethyl-6-oxo-1,4,5,6-tetrahydro-pyrimidin-4-yl)-4-fluoro-phenyl]-2-(4-chloro-phenyl)-2-hydroxy-propionamide

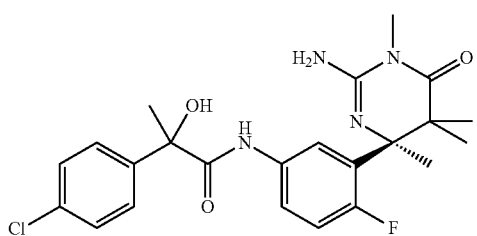 [SMILES: CN1C(=O)C(C)(C)[C@@](C)(c2cc(NC(=O)C(C)(O)c3ccc(Cl)cc3)ccc2F)N=C1N]

The coupling of (S)-2-amino-6-(5-amino-2-fluoro-phenyl)-3,5,5,6-tetramethyl-5,6-dihydro-3H-pyrimidin-4-one (intermediate J) and 2-(4-chloro-phenyl)-2-hydroxy-propionic acid yielded a mixture of epimers of the title compound as a white solid. MS (ESI): m/z=461.3 [M+H]⁺.

Example 142

(R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide

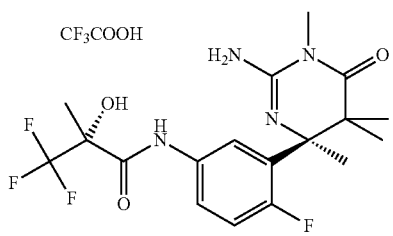

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and (R)-3,3,3-trifluoro-2-hydroxy-2-methyl-propionic acid followed by deprotection of the intermediate yielded the title compound as a white solid. MS (ESI): m/z=419.2 [M+H]⁺.

Example 143

(S)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide

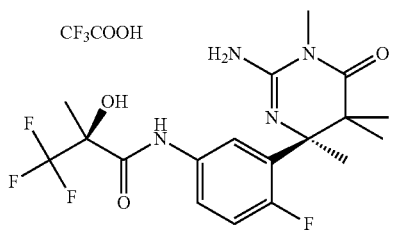 [SMILES: "CF3COOH" ; CN1C(=O)C(C)(C)[C@@](C)(c2cc(NC(=O)[C@](C)(O)C(F)(F)F)ccc2F)N=C1N]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F2) and (S)-3,3,3-trifluoro-2-hydroxy-2-methyl-propionic acid followed by deprotection of the intermediate yielded the title compound as a white solid. MS (ESI): m/z=419.2 [M+H]⁺.

Example 144

(S)-2-Amino-6-[5-(1,1-dioxo-2,3-dihydro-1H-1-benzo[b]thiophen-3-ylamino)-2-fluoro-phenyl]-3,5,5,6-tetramethyl-5,6-dihydro-3H-pyrimidin-4-one

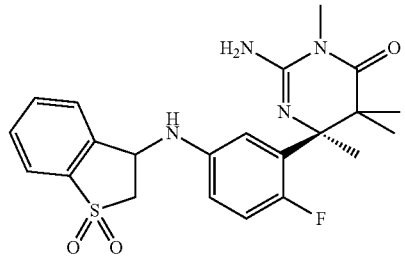 [SMILES: CN1C(=O)C(C)(C)[C@@](C)(c2cc(NC3CS(=O)(=O)c4ccccc43)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and benzo[b]thiophen-3(2H)-one-1,1-dioxide using decaborane yielded a mixture of epimers of the title compound as a colorless solid. MS (ESI): m/z=445.2 [M+H]⁺.

Example 145

(S)-2-Amino-6-[5-(2,5-difluoro-phenylamino)-2-fluoro-phenyl]-3,5,5,6-tetramethyl-5,6-dihydro-3H-pyrimidin-4-one

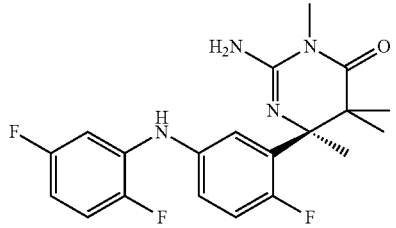 [SMILES: CN1C(=O)C(C)(C)[C@@](C)(c2cc(Nc3cc(F)ccc3F)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,5-difluoro-phenylamine according to procedure B yielded the title compound as an off white solid. MS (ESI): m/z=391.4 [M+H]⁺.

Example 146

(S)-2-Amino-6-(2-fluoro-5-(2,4,5-trimethylphenylamino)phenyl)-3,5,5,6-tetramethyl-5,6-dihydropyrimidin-4(3H)-one

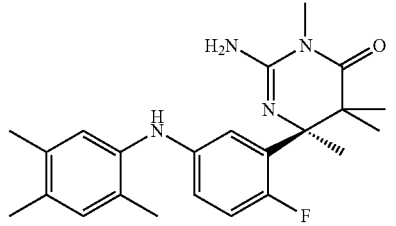

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,4,5-trimethylphenylamine according to procedure A yielded the title compound as a white solid. MS (ESI): m/z=397.2 [M+H]⁺.

Example 147

(S)—N-(3-(2-amino-1,4,5,5-tetramethyl-6-oxo-1,4,5,6-tetrahydropyrimidin-4-yl)-4-fluorophenyl)-1-hydroxycyclobutanecarboxamide

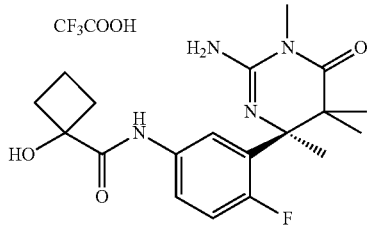 [SMILES: "CF3COOH" ; CN1C(=O)C(C)(C)[C@@](C)(c2cc(NC(=O)C3(O)CCC3)ccc2F)N=C1N]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F) and 1-hydroxycyclobutanecarboxylic acid followed by deprotection of the intermediate yielded the title compound as a colorless amorphous solid. MS (ESI): m/z=377.4 [M+H]$^+$.

Example 148

(S)—N-(3-(2-amino-1,4,5,5-tetramethyl-6-oxo-1,4,5,6-tetrahydropyrimidin-4-yl)-4-fluorophenyl)-3,3,3-trifluoro-2-hydroxy-2-(trifluoromethyl)propanamide

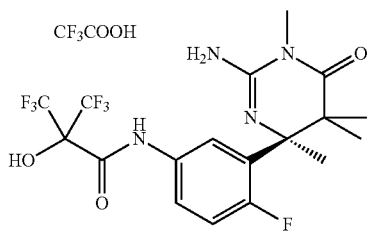 [SMILES: "CF3COOH" ; CN1C(=O)C(C)(C)[C@@](C)(c2cc(NC(=O)C(O)(C(F)(F)F)C(F)(F)F)ccc2F)N=C1N]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F) and 3,3,3-trifluoro-2-hydroxy-2-trifluoromethyl-propionic acid followed by deprotection of the intermediate yielded the title compound as a colorless amorphous solid. MS (ESI): m/z=473.3 [M+H]$^+$.

Example 149

(S)-4-(3-(2-Amino-1,4,5,5-tetramethyl-6-oxo-1,4,5,6-tetrahydropyrimidin-4-yl)-4-fluorophenylamino)-2-methylbenzonitrile

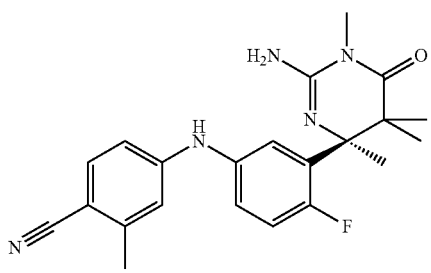 [SMILES: Cc1cc(Nc2ccc(F)c([C@@]3(C)N=C(N)N(C)C(=O)C3(C)C)c2)ccc1C#N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-2-methyl-benzonitrile according to procedure B followed by deprotection yielded the title compound as a white solid. MS (ESI): m/z=394.1 [M+H]$^+$.

Example 150

(S)-2-Amino-6-(5-(5-chloro-2-methoxyphenylamino)-2-fluorophenyl)-3,5,5,6-tetramethyl-5,6-dihydropyrimidin-4(3H)-one

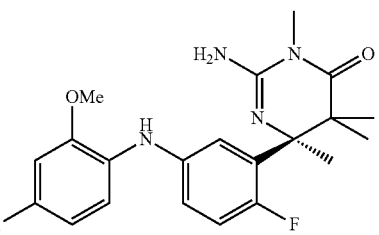

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-chloro-2-methoxy-phenylamine according to procedure A followed by deprotection yielded the title compound as a white solid. MS (ESI): m/z=419.2 [M+H]$^+$.

Example 151

N-[3-((S)-2-Amino-1,4,5,5-tetramethyl-6-oxo-1,4,5,6-tetrahydro-pyrimidin-4-yl)-4-fluoro-phenyl]-isobutyramide

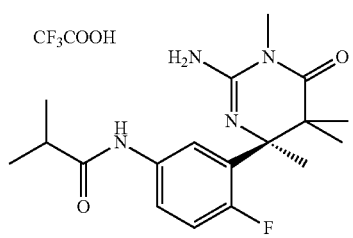 [SMILES: "CF3COOH" ; CC(C)C(=O)Nc1ccc(F)c([C@@]2(C)N=C(N)N(C)C(=O)C2(C)C)c1]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (intermediate F) and isobutyric acid followed by deprotection of the intermediate yielded the title compound as a colorless oil. MS (ESI): m/z=349.3 [M+H]$^+$.

Example 152

(S)-4-(3-(2-Amino-1,4,5,5-tetramethyl-6-oxo-1,4,5,6-tetrahydropyrimidin-4-yl)-4-fluorophenylamino)-3-fluorobenzonitrile

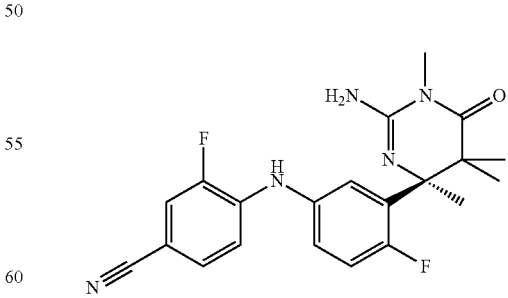

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-3-fluoro-benzonitrile according to procedure B followed by deprotection yielded the title compound as an off-white foam. MS (ESI): m/z=398.2 [M+H]$^+$.

Example 153

(S)-4-(3-(2-Amino-1,4,5,5-tetramethyl-6-oxo-1,4,5,6-tetrahydropyrimidin-4-yl)-4-fluorophenylamino)benzonitrile

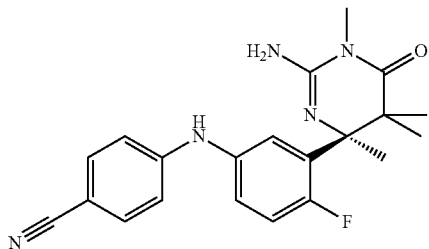 [SMILES: CN1C(=O)C(C)(C)[C@@](C)(c2cc(Nc3ccc(C#N)cc3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-benzonitrile according to procedure B followed by deprotection yielded the title compound as an off-white solid. MS (ESI): m/z=380.3 [M+H]⁺.

Example 154

(S)-2-Amino-6-(5-(4-chloro-2-methoxy-5-methylphenylamino)-2-fluorophenyl)-3,5,5,6-tetramethyl-5,6-dihydropyrimidin-4(3H)-one

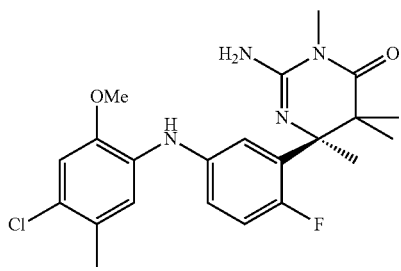 [SMILES: COc1cc(Cl)c(C)cc1Nc1ccc(F)c([C@@]2(C)N=C(N)N(C)C(=O)C2(C)C)c1]

The coupling (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-chloro-2-methoxy-5-methyl-phenylamine according to procedure B followed by deprotection yielded the title compound as an off-white solid. MS (ESI): m/z=433.3 [M+H]⁺.

Example 155

(6S)-2-Amino-6-(5-((2R,6S)-2,6-dimethyltetrahydro-2H-pyran-4-ylamino)-2-fluorophenyl)-3,5,5,6-tetramethyl-5,6-dihydropyrimidin-4(3H)-one

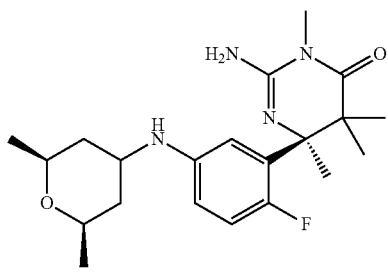

The reductive amination of (S)-2-amino-6-(5-amino-2-fluoro-phenyl)-3,5,5,6-tetramethyl-5,6-dihydro-3H-pyrimidin-4-one (intermediate J) and (2R,6S)-2,6-dimethyl-tetrahydro-pyran-4-one using decaborane yielded the title compound as a white solid. MS (ESI): m/z=391.1 [M+H]⁺.

Example 156

(S)-2-Amino-6-(5-(2,2-dimethyl-2,3-dihydrobenzofuran-7-ylamino)-2-fluorophenyl)-3,5,5,6-tetramethyl-5,6-dihydropyrimidin-4(3H)-one

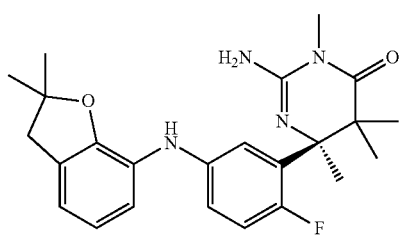

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,2-dimethyl-2,3-dihydro-benzofuran-7-ylamine according to procedure B followed by deprotection yielded the title compound as an off-white solid. MS (ESI): m/z=425.2 [M+H]⁺.

Example 157

(S)-2-Amino-6-(5-(2,3-dihydrobenzofuran-7-ylamino)-2-fluorophenyl)-3,5,5,6-tetramethyl-5,6-dihydropyrimidin-4(3H)-one

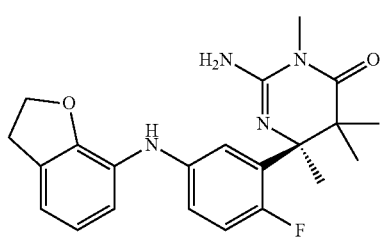 [SMILES: CN1C(=O)C(C)(C)[C@@](C)(c2cc(Nc3cccc4c3OCC4)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 2,3-dihydro-benzofuran-7-ylamine according to procedure B followed by deprotection yielded the title compound as an off-white solid. MS (ESI): m/z=397.2 [M+H]⁺.

Example 158

(S)-2-Amino-6-[2-fluoro-5-(2-hydroxy-4,4-dimethyl-cyclopentylamino)-phenyl]-3,5,5,6-tetramethyl-5,6-dihydro-3H-pyrimidin-4-one

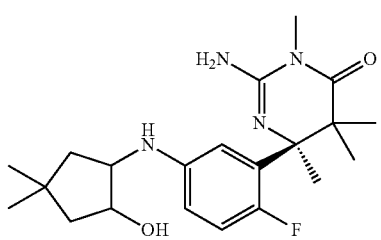

The reductive amination of (S)-2-amino-6-(5-amino-2-fluoro-phenyl)-3,5,5,6-tetramethyl-5,6-dihydro-3H-pyrimidin-4-one (intermediate J) and rac-2-hydroxy-4,4-dimethyl-cyclopentanone using decaborane yielded a mixture of epimers of the title compound as white solid. MS (ESI): m/z=391.4 [M+H]⁺.

Example 159

(S)-2-Amino-6-{2-fluoro-5-[1-(2-methyl-5-trifluoromethyl-oxazol-4-yl)-ethylamino]-phenyl}-3,5,5,6-tetramethyl-5,6-dihydro-3H-pyrimidin-4-one

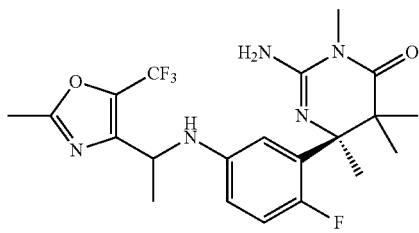

a) 2-Methyl-5-trifluoromethyl-oxazole-4-carboxylic acid methoxy-methyl-amide

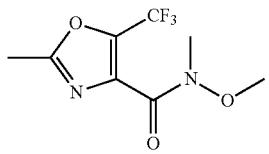

To a solution of 2-methyl-5-trifluoromethyl-oxazole-4-carboxylic acid (500 mg, 2.56 mmole) in dichloromethane (5 ml) was subsequently treated at 22° C. with N,O-dimethylhydroxylamine hydrochloride (262 mg, 2.69 mmole), N-methylmorpholine (0.29 ml, 2.69 mmole) and EDCl.HCl (516 mg, 2.69 mmole) and stirring was continued for 16 h. The mixture was washed with 1 M aqueous HCl and H2O, the organic layer was dried and evaporated to give the title compound (559 mg) as a colorless oil which was used without further purification. MS: m/z=239.0 [M]+.

b) 1-(2-Methyl-5-trifluoromethyl-oxazol-4-yl)-ethanone

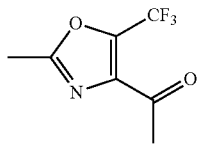

To a solution of MeMgBr in diethyl ether (3 M, 0.63 ml, 1.89 mmole) was added at 0° C. a solution of 2-methyl-5-trifluoromethyl-oxazole-4-carboxylic acid methoxy-methyl-amide (300 mg, 1.26 mmole) and stirring was continued at 22° C. for 1 h. The mixture was washed with 1 M aqueous HCl and H2O, the organic layer was dried, evaporated and the residue purified by chromatography on silica gel using cyclohexane/AcOEt (4:1) to give the title compound (155 mg) as a colorless oil. MS: m/z=193 [M]+.

The reductive amination of (S)-2-amino-6-(5-amino-2-fluoro-phenyl)-3,5,5,6-tetramethyl-5,6-dihydro-3H-pyrimidin-4-one (intermediate J) and 1-(2-methyl-5-trifluoromethyl-oxazol-4-yl)-ethanone using decaborane yielded a 1:1 epimer mixture of (S)-2-amino-6-{2-fluoro-5-[1-(2-methyl-5-trifluoromethyl-oxazol-4-yl)-ethylamino]-phenyl}-3,5,5,6-tetramethyl-5,6-dihydro-3H-pyrimidin-4-one as a colorless solid. MS (ESI): m/z=456.3 [M+H]+.

Example 160

(S)-2-Amino-6-{5-[(4-chloro-1-difluoromethyl-1H-pyrazol-3-ylmethyl)-amino]-2-fluoro-phenyl}-3,5,5,6-tetramethyl-5,6-dihydro-3H-pyrimidin-4-one

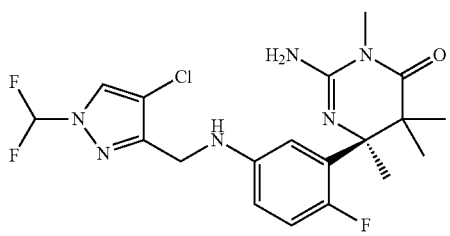 [SMILES: CN1C(=O)C(C)(C)[C@@](C)(c2cc(NCc3nn(C(F)F)cc3Cl)ccc2F)N=C1N]

a) 1-Difluoromethyl-1H-pyrazole-3-carboxylic acid methyl ester

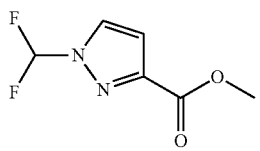

A solution of 1-difluoromethyl-1H-pyrazole-3-carboxylic acid (CAS925179-O2-8) (500 mg, 3.1 mmole) in methanol (18 ml) was cooled to 0° C. and treated with sulphuric acid (98%, 0.2 ml, 3.1 mmol). The mixture was heated to reflux for 2 hours, cooled to 22° C. and concentrated at reduced pressure. The residue was partitioned between AcOEt and water, the organic layer was washed with water until the water phase showed a neutral pH, dried and evaporated to give the title compound (535 mg) as a colorless liquid which was used without further purification. MS: m/z=177.1 [M+H]+.

b) 4-Chloro-1-difluoromethyl-1H-pyrazole-3-carboxylic acid methyl ester

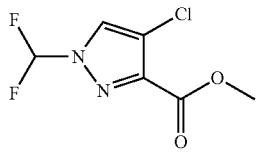

A mixture of 1-difluoromethyl-1H-pyrazole-3-carboxylic acid methyl ester (535 mg, 3 mmole) and N-chloro-succinimide (1.22 g, 9.1 mmole) in DMF (5 ml) was heated at 50° C. overnight. The reaction mixture was cooled, partitioned between AcOEt and water, the organic layer was washed with water, dried, evaporated and the residue was purified by chromatography on silica gel using cyclohexane/AcOEt (3:1) to give the title compound (540 mg) as a white solid. MS: m/z=209.9 [M]+.

c) 4-Chloro-1-difluoromethyl-1H-pyrazole-3-carboxylic acid

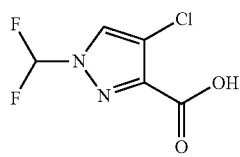

A solution of 4-chloro-1-difluoromethyl-1H-pyrazole-3-carboxylic acid methyl ester (540 mg, 2.6 mmole) in THF (18 ml) was treated at 22° C. with a solution of lithium hydroxide (135 mg, 5.6 mmole) in a 1:1-mixture of water and methanol (12 ml). After 1 hour the reaction was complete, and the solvents were evaporated at reduced pressure. The residue was partitioned between 2 M aqueous HCl and AcOEt, the organic layer was dried, evaporated, the residue was triturated with pentane and the solid was dried to give the title compound (477 mg) as a white solid. MS: m/z=195.0 [M−H]−.

d) 4-Chloro-1-difluoromethyl-1H-pyrazole-3-carboxylic acid methoxy-methyl-amide

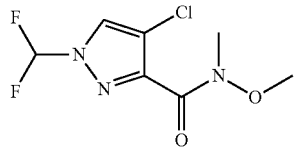

A solution of 4-chloro-1-difluoromethyl-1H-pyrazole-3-carboxylic acid (150 mg, 0.76 mmole) in dichloromethane (5 ml) was subsequently treated at 22° C. with N,O-dimethylhydroxylamine hydrochloride (78 mg, 0.80 mmole), N-methylmorpholine (0.09 ml, 0.8 mmole) and EDCI.HCl (154 mg, 0.8 mmole) and stirring was continued for 16 h. The mixture was washed with 1 M aqueous HCl and H2O, the organic layer was dried, evaporated and the residue purified by chromatography on silica gel using cyclohexane/AcOEt (2:1) to give the title compound (164 mg) as a colorless oil. MS: m/z=240.1 [M]+.

e) 4-Chloro-1-difluoromethyl-1H-pyrazole-3-carbaldehyde

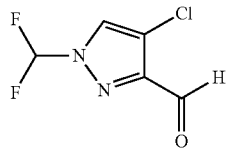

To a solution of 4-chloro-1-difluoromethyl-1H-pyrazole-3-carboxylic acid methoxy-methyl-amide (164 mg, 0.68 mmole) in THF (5 ml) was added at 0° C. a solution of LiAlH4 (1M in THF, 0.35 ml) and stirring was continued for 30 min. The mixture was quenched at −15° C. with saturated aqueous KHSO4, extracted with diethyl ether, the organic layer was dried, evaporated and the residue purified by chromatography on silica gel using cyclohexane/AcOEt (4:1) to give the title compound (71 mg) as a pale yellow oil.

The reductive amination of (S)-2-amino-6-(5-amino-2-fluoro-phenyl)-3,5,5,6-tetramethyl-5,6-dihydro-3H-pyrimidin-4-one (intermediate J) and 4-chloro-1-difluoromethyl-1H-pyrazole-3-carbaldehyde using decaborane yielded (S)-2-amino-6-{5-[(4-chloro-1-difluoromethyl-1H-pyrazol-3-ylmethyl)-amino]-2-fluoro-phenyl}-3,5,5,6-tetramethyl-5,6-dihydro-3H-pyrimidin-4-one as colorless solid. MS (ESI): m/z=443.4 [M+H]+.

Example 161

(S)-4-(3-(2-Amino-1,4,5,5-tetramethyl-6-oxo-1,4,5,6-tetrahydropyrimidin-4-yl)-4-fluorophenylamino)-3-(trifluoromethoxy)benzonitrile

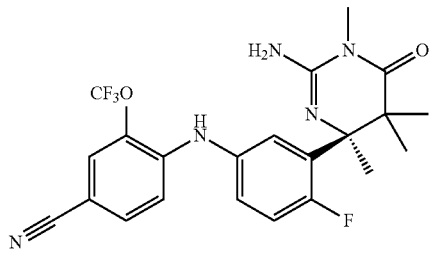

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-3-trifluoromethoxy-benzonitrile according to procedure B followed by deprotection yielded the title compound as an off-white solid. MS (ESI): m/z=464.3 [M+H]+.

Example 162

2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile

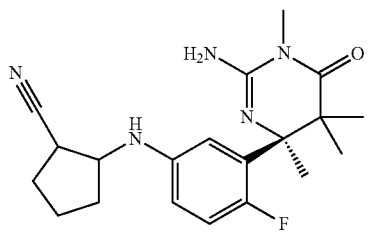 [SMILES: CN1C(=O)C(C)(C)[C@@](C)(c2cc(NC3CCCC3C#N)ccc2F)N=C1N]

The reductive amination of (S)-2-amino-6-(5-amino-2-fluoro-phenyl)-3,5,5,6-tetramethyl-5,6-dihydro-3H-pyrimidin-4-one (intermediate J) and rac-2-oxo-cyclopentanecarbonitrile using decaborane yielded a mixture of epimers of the title compound as a white foam. MS (ESI): m/z=372.2 [M+H]+.

Example 163

(S)-4-(3-(2-Amino-1,4,5,5-tetramethyl-6-oxo-1,4,5,6-tetrahydropyrimidin-4-yl)-4-fluorophenylamino)-3-(trifluoromethyl)benzonitrile

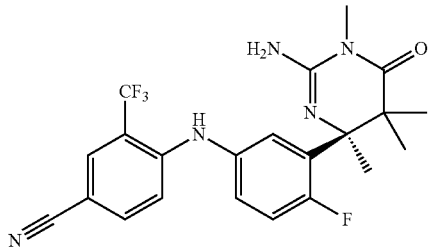 [SMILES: CN1C(=O)C(C)(C)[C@@](C)(c2cc(Nc3ccc(C#N)cc3C(F)(F)F)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-3-trifluoromethyl-benzonitrile according to procedure B followed by deprotection yielded the title compound as a pale yellow solid. MS (ESI): m/z=448.2 [M+H]$^+$.

Example 164

(S)-2-Amino-6-(2-fluoro-5-(4-(methylsulfonyl)phenylamino)phenyl)-3,5,5,6-tetramethyl-5,6-dihydropyrimidin-4(3H)-one

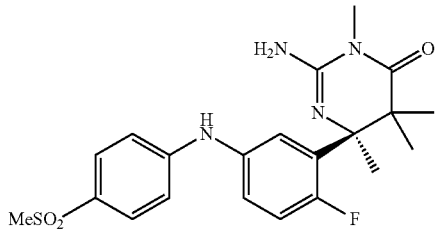

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-methanesulfonyl-phenylamine according to procedure B followed by deprotection yielded the title compound as a white solid. MS (ESI): m/z=433.3 [M+H]$^+$.

Example 165

(S)-3-(3-(2-Amino-1,4,5,5-tetramethyl-6-oxo-1,4,5,6-tetrahydropyrimidin-4-yl)-4-fluorophenylamino)-4-fluorobenzonitrile

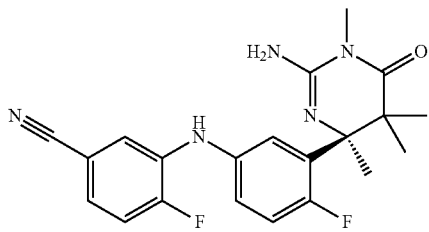 [SMILES: CN1C(=O)C(C)(C)[C@@](C)(c2cc(Nc3cc(C#N)ccc3F)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 3-amino-4-fluoro-benzonitrile according to procedure B followed by deprotection yielded the title compound as a pale yellow solid. MS (ESI): m/z=398.2 [M+H]$^+$.

Example 166

(S)-4-(3-(2-Amino-1,4,5,5-tetramethyl-6-oxo-1,4,5,6-tetrahydropyrimidin-4-yl)-4-fluorophenylamino)-2,5-difluorobenzonitrile

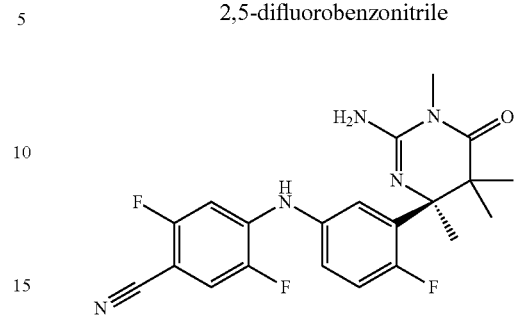

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-2,5-difluoro-benzonitrile according to procedure A followed by deprotection yielded the title compound as a white foam. MS (ESI): m/z=416.3 [M+H]$^+$.

Example 167

3-[3-((S)-2-Amino-1,4,5,5-tetramethyl-6-oxo-1,4,5,6-tetrahydro-pyrimidin-4-yl)-4-fluoro-phenylamino]-benzonitrile

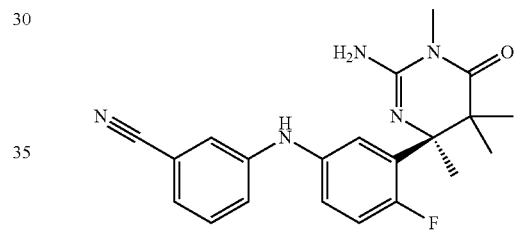

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 3-amino-benzonitrile according to procedure B followed by deprotection yielded the title compound as a pale yellow foam. MS (ESI): m/z=380.3 [M+H]$^+$.

Example 168

4-[3-((S)-2-Amino-1,4,5,5-tetramethyl-6-oxo-1,4,5,6-tetrahydro-pyrimidin-4-yl)-4-fluoro-phenylamino]-3-chloro-benzonitrile

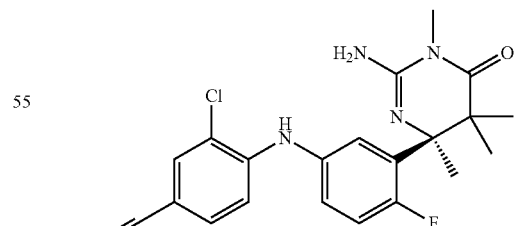

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 4-amino-3-chloro-benzonitrile according to procedure B followed by deprotection yielded the title compound as a white solid. MS (ESI): m/z=414.1 and 416.1 [M+H]$^+$.

Example 169

5-[3-((S)-2-Amino-1,4,5,5-tetramethyl-6-oxo-1,4,5,6-tetrahydro-pyrimidin-4-yl)-4-fluoro-phenylamino]-2-methyl-benzonitrile

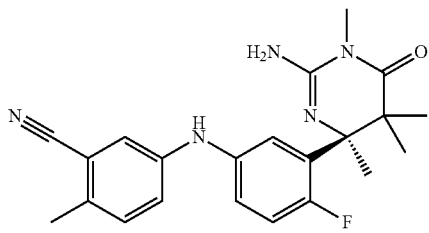 [SMILES: Cc1ccc(Nc2ccc(F)c([C@@]3(C)N=C(N)N(C)C(=O)C3(C)C)c2)cc1C#N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 5-amino-2-methyl-benzonitrile according to procedure B followed by deprotection yielded the title compound as an off-white solid. MS (ESI): m/z=394.1 [M+H]$^+$.

Example 170

(S)-2-Amino-6-(2-fluoro-5-(6-methoxypyridin-3-ylamino)phenyl)-3,5,5,6-tetramethyl-5,6-dihydropyrimidin-4(3H)-one

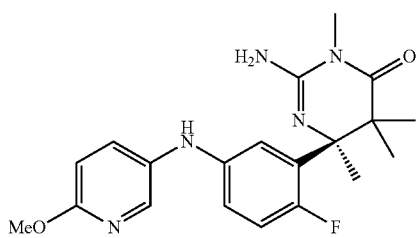 [SMILES: COc1ccc(Nc2ccc(F)c([C@@]3(C)N=C(N)N(C)C(=O)C3(C)C)c2)cn1]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 6-methoxy-pyridin-3-ylamine according to procedure B followed by deprotection yielded the title compound as an pale brown foam. MS (ESI): m/z=386.2 [M+H]$^+$.

Example 171

(S)-2-Amino-6-(2-fluoro-5-(6-methylpyridin-3-ylamino)phenyl)-3,5,5,6-tetramethyl-5,6-dihydropyrimidin-4(3H)-one

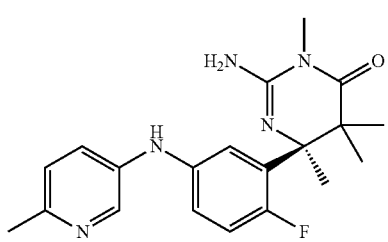

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 6-methyl-pyridin-3-ylamine according to procedure B followed by deprotection yielded the title compound as an off-white foam. MS (ESI): m/z=370.2 [M+H]$^+$.

Example 172

(S)-2-Amino-6-(2-fluoro-5-(6-(2,2,2-trifluoroethoxy)pyridin-3-ylamino)phenyl)-3,5,5,6-tetramethyl-5,6-dihydropyrimidin-4(3H)-one

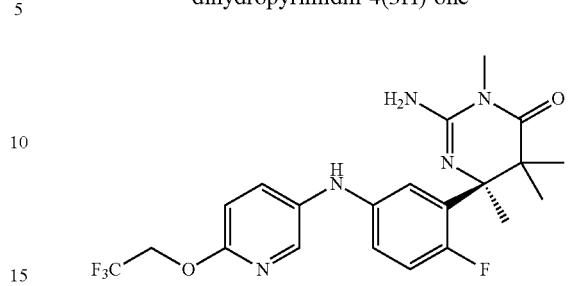

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 6-(2,2,2-trifluoro-ethoxy)-pyridin-3-ylamine according to procedure B followed by deprotection yielded the title compound as an off-white foam. MS (ESI): m/z=454.2 [M+H]$^+$.

Example 173

(S)-2-Amino-6-(2-fluoro-5-(6-(trifluoromethyl)pyridin-3-ylamino)phenyl)-3,5,5,6-tetramethyl-5,6-dihydropyrimidin-4(3H)-one

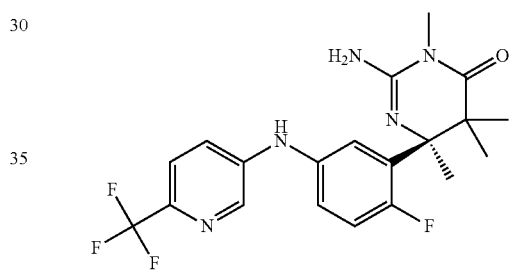

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 6-trifluoromethyl-pyridin-3-ylamine according to procedure B followed by deprotection yielded the title compound as a pale yellow foam. MS (ESI): m/z=424.2 [M+H]$^+$.

Example 174

(S)-2-Amino-6-(2-fluoro-5-(5-fluoropyridin-3-ylamino)phenyl)-3,5,5,6-tetramethyl-5,6-dihydropyrimidin-4(3H)-one

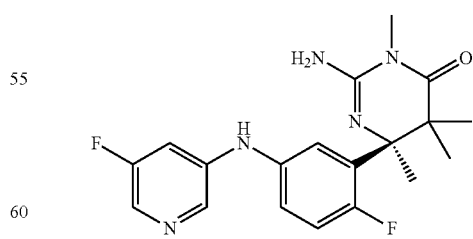

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 5-fluoro-pyridin-3-ylamine according to procedure B followed by deprotection yielded the title compound as an off-white foam. MS (ESI): m/z=374.2 [M+H]$^+$.

Example 175

(S)-2-Amino-6-(2-fluoro-5-(5-(trifluoromethyl)pyridin-3-ylamino)phenyl)-3,5,5,6-tetramethyl-5,6-dihydropyrimidin-4(3H)-one

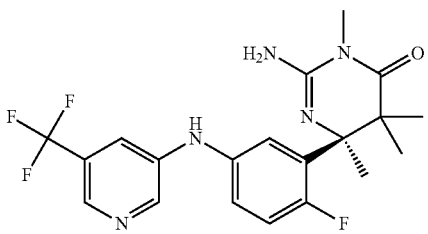 [SMILES: CN1C(=O)C(C)(C)[C@@](C)(c2cc(Nc3cncc(C(F)(F)F)c3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 5-trifluoromethyl-pyridin-3-ylamine according to procedure B followed by deprotection yielded the title compound as an off-white foam. MS (ESI): m/z=424.2 [M+H]$^+$

Example 176

(S)-2-Amino-6-(5-(6-chloropyridin-3-ylamino)-2-fluorophenyl)-3,5,5,6-tetramethyl-5,6-dihydropyrimidin-4(3H)-one

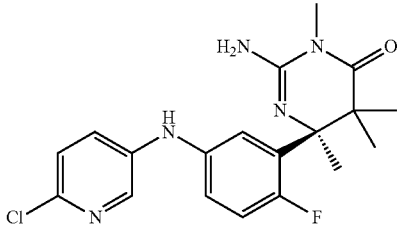 [SMILES: CN1C(=O)C(C)(C)[C@@](C)(c2cc(Nc3ccc(Cl)nc3)ccc2F)N=C1N]

The coupling of (S)-2-{[bis-(4-methoxy-phenyl)-phenyl-methyl]-amino}-6-(5-bromo-2-fluoro-phenyl)-3,5,5,6-tetramethyl-5,6-dihydro-3H-pyrimidin-4-one (intermediate K) and 5-amino-2-chloropyridine according to procedure B followed by deprotection yielded the title compound as an off-white foam. MS (ESI): m/z=390.2/392.2 [M+H]$^+$.

The invention claimed is:
1. A compound according to formula I

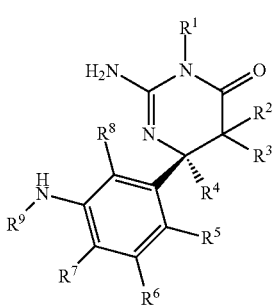

wherein
$R^1$ is selected from $C_{1-7}$-alkyl or $C_{3-7}$-cycloalkyl;
$R^2$ is selected from hydrogen, $C_{1-7}$-alkyl and $C_{3-7}$-cycloalkyl;
$R^3$ is selected from hydrogen, $C_{1-7}$-alkyl and $C_{3-7}$-cycloalkyl;
or $R^2$ and $R^3$ are independently from each other hydrogen and $C_{1-7}$-alkyl;
$R^4$ is $C_{1-7}$-alkyl or $C_{3-7}$-cycloalkyl;
$R^5$ is selected from hydrogen, $C_{1-7}$-alkyl, halogen, cyano and $C_{1-7}$-alkoxy;
or $R^4$ and $R^5$ together are —$(CH_2)_m$— with m being 2 or 3 and thus form a ring;
$R^6$, $R^7$ and $R^8$ independently from each other are selected from hydrogen and halogen; and
$R^9$ is —(CO)—$R^{10}$ or —$R^{11}$, wherein
$R^{10}$ is selected from the group consisting of
$C_{1-7}$-alkyl,
—$(CHR^{12})_m$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, benzyl and phenyl, said phenyl being unsubstituted or substituted by halogen, $R^{12}$ is hydrogen or $C_{1-7}$-alkyl, and m is 0, 1 or 2,
halogen-$C_{1-7}$-alkyl,
hydroxy-halogen-$C_{1-7}$-alkyl,
$C_{1-7}$-alkoxy-halogen-$C_{1-7}$-alkyl, and
—CH(OH)-phenyl, wherein phenyl is unsubstituted or substituted by halogen; and
$R^{11}$ is selected from the group consisting of
$C_{1-7}$-alkyl,
—$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen,
$R^{14}$ is hydrogen or $C_{1-7}$-alkyl, and p is 0, 1 or 2,
halogen-$C_{1-7}$-alkyl,
indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen,
tetrahydronaphtalenyl, being unsubstituted or substituted by one, two or three groups selected from $C_{1-7}$-alkyl and halogen,
6,7-dihydro-5H-cyclopenta[b]pyridinyl, being unsubstituted or substituted by one, two or three groups selected from $C_{1-7}$-alkyl and halogen,
hydroxy-halogen-$C_{1-7}$-alkyl,
$C_{1-7}$-alkoxy-halogen-$C_{1-7}$-alkyl,
—$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;
—$(CHR^{16})_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, —$SO_2$—$C_{1-7}$- alkyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, $C_{1-7}$-alkyl-carbonyl, oxo, $C_{3-7}$-cycloalkyl, imidazolyl, benzyl, phenylsulfanyl and phenyl, said phenyl being unsubstituted or substituted by halogen, $R^{17}$ is hydrogen or $C_{1-7}$-alkyl and t is 0, 1 or 2;

or pharmaceutically acceptable salts thereof.

2. A compound according to claim 1, wherein $R^{10}$ is selected from the group consisting of halogen-$C_{1-7}$-alkyl, hydroxy-halogen-$C_{1-7}$-alkyl, and $C_{1-7}$-alkoxy-halogen-$C_{1-7}$-alkyl.

3. A compound according to claim 1, wherein $R^{10}$ is selected from the group consisting of —$(CHR^{12})_m$—$C_{3-7}$-cycloalkyl, wherein cycloalkyl is unsubstituted or substituted by one or two halogen-$C_{1-7}$-alkyl groups, and m is 0, and hydroxy-halogen-$C_{1-7}$-alkyl.

4. A compound according to claim 3 wherein $R^{10}$ is 1-trifluoromethyl-cyclopropanyl, 2,2,2-trifluoro-1-hydroxy-ethyl or 1,1,1-trifluoro-2-hydroxy-2-methyl-ethyl.

5. A compound according to claim 1, wherein $R^9$ is $R^{11}$ and $R^{11}$ is selected from the group consisting of $C_{1-7}$-alkyl, —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, halogen-$C_{1-7}$-alkyl, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, hydroxy-halogen-$C_{1-7}$-alkyl, $C_{1-7}$-alkoxy-halogen-$C_{1-7}$-alkyl, —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—$(CHR^{16})_s$-aryl, wherein aryl is unsubstituted or substituted by one, two or three groups consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2.

6. A compound according to claim 5, wherein $R^{11}$ is selected from the group consisting of —$(CHR^{14})_p$—$C_{3-7}$-cycloalkyl, wherein cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2, indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen, tetrahydronaphtalenyl, being unsubstituted or substituted by one, two or three groups selected from $C_{1-7}$-alkyl or halogen, 6,7-dihydro-5H-cyclopenta[b]pyridinyl, being unsubstituted or substituted by one, two or three groups selected from $C_{1-7}$-alkyl or halogen, —$(CHR^{15})_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2;

—$(CHR^{16})_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2; and —$(CHR^{17})_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, and t is 0, 1 or 2.

7. A compound according to claim 5, wherein $R^{11}$ is —$(CHR^{14})_p$—$C_{3-7}$-cycloalkyl is unsubstituted or substituted by one, two or three groups selected from the group consisting of $C_{1-7}$-alkyl, hydroxy, halogen, halogen-$C_{1-7}$-alkyl, cyano, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyloxy, benzyl and phenyl, said phenyl being unsubstituted or substituted by halogen, $R^{14}$ is hydrogen or $C_{1-7}$-alkyl, and p is 0, 1 or 2.

8. A compound according to claim 5, wherein $R^{11}$ is selected from the group consisting of
  indanyl, being unsubstituted or substituted by one, two or three groups selected from the group consisting of $C_{1-7}$-alkyl, $C_{1-7}$-alkoxy, carboxyl, carboxyl-$C_{1-7}$-alkyl and halogen,
  tetrahydronaphtalenyl, being unsubstituted or substituted by one, two or three groups selected from $C_{1-7}$-alkyl and halogen,
  6,7-dihydro-5H-cyclopenta[b]pyridinyl, being unsubstituted or substituted by one, two or three groups selected from $C_{1-7}$-alkyl and halogen, and
  —(CHR$^{15}$)$_q$-heterocyclyl, wherein heterocyclyl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, carboxyl-$C_{1-7}$-alkyl, $C_{1-7}$-alkoxycarbonyl-$C_{1-7}$-alkyl, $C_{1-7}$-alkylcarbonyl, $C_{1-7}$-alkylcarbonyloxy, oxo, $C_{3-7}$-cycloalkyl, imidazolyl, benzyl, phenylsulfanyl and phenyl, said phenyl being unsubstituted or substituted by halogen, $R^{15}$ is hydrogen or $C_{1-7}$-alkyl, and q is 0, 1 or 2.

9. A compound according to claim 5, wherein $R^{11}$ is —(CHR$^{16}$)$_s$-aryl, wherein aryl is unsubstituted or substituted by one, two or three groups selected from the group consisting of $C_{1-7}$-alkyl, hydroxy, halogen, halogen-$C_{1-7}$-alkyl, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{16}$ is hydrogen or $C_{1-7}$-alkyl, and s is 0, 1 or 2.

10. A compound according to claim 5, wherein $R^{11}$ is —(CHR$^{17}$)$_t$-heteroaryl, wherein heteroaryl is unsubstituted or substituted by one, two or three groups selected from the group consisting of $C_{1-7}$-alkyl, halogen, halogen-$C_{1-7}$-alkyl, hydroxy, $C_{1-7}$-alkoxy, halogen-$C_{1-7}$-alkoxy, cyano, hydroxy-$C_{1-7}$-alkyl, carboxyl, $C_{1-7}$-alkoxycarbonyl, oxo, $C_{3-7}$-cycloalkyl, imidazolyl, benzyl, phenylsulfanyl and phenyl, said phenyl being unsubstituted or substituted by halogen, $R^{17}$ is hydrogen or $C_{1-7}$-alkyl, and t is 0, 1 or 2.

11. A compound according to claim 5, wherein $R^{11}$ is selected from the group consisting of $C_{1-7}$-alkyl, halogen-$C_{1-7}$-alkyl, hydroxy-halogen-$C_{1-7}$-alkyl and $C_{1-7}$-alkoxy-halogen-$C_{1-7}$-alkyl.

12. A compound according to claim 11, wherein $R^{11}$ is selected from group consisting of
  —(CHR$^{14}$)$_p$—$C_{3-7}$-cycloalkyl, wherein cycloalkyl is unsubstituted or substituted by one or two groups selected from the group consisting of hydroxy, halogen and cyano, $R^{14}$ is hydrogen, and p is 0 or 1,
  —(CHR$^{15}$)$_q$-heterocyclyl, wherein heterocyclyl is unsubstituted, $R^{15}$ is hydrogen, and q is 0 or 1;
  —(CHR$^{16}$)$_s$-aryl, wherein aryl is unsubstituted or substituted by one or two groups selected from the group consisting of halogen-$C_{1-7}$-alkyl, and $C_{1-7}$-alkoxy, and s is 0; and
  —(CHR$^{17}$)$_t$-heteroaryl, wherein heteroaryl is unsubstituted or substituted by one or two groups selected from the group consisting of $C_{1-7}$-alkyl, halogen, halogen-$C_{1-7}$-alkyl, $C_{1-7}$-alkoxy, and oxo, $R^{17}$ is hydrogen or $C_{1-7}$-alkyl, and t is 0 or 1.

13. A compound according to claim 12, wherein $R^{11}$ is selected from the group consisting of: tetrahydro-furyl, tetrahydro-pyranyl, 2,2-difluoro-cyclopropyl-methyl, 3-chloro-6,7-dihydro-5H-cyclopenta[b]pyridinyl, tetrahydro-furyl-methyl, 4-chloro-1-methyl-1H-pyrazolyl-methyl, 1-methyl-1H-pyrazolyl, 5-hydroxybicyclo[2.2.1]heptanyl, 5-methyl-isoxazol-3-yl-methyl, pyridinyl, 1-(2H-pyrazolyl)-ethyl, 2-methoxy-5-(trifluoromethyl)phenyl, 1-(5-methyl-2H-pyrazolyl)-ethyl, 4-chloro-2H-pyrazolyl, cyano-cyclopentyl and 1,1-dioxo-2,3-dihydro-1H-1-benzo[b]thiophenyl.

14. A compound according to claim 1, selected from the group consisting of
  salt of 1-Trifluoromethyl-cyclopropanecarboxylic acid [3-((S)-2-amino-1,4,5,5-tetramethyl-6-oxo-1,4,5,6-tetrahydro-pyrimidin-4-yl)-4-fluoro-phenyl]-amide with trifluoro-acetic acid,
  (6S)-2-Amino-6-(2-fluoro-5-(5-hydroxybicyclo[2.2.1]heptan-2-ylamino)phenyl)-3,5,5,6-tetramethyl-5,6-dihydropyrimidin-4(3H)-one,
  (6S)-2-Amino-6-(5-(3-chloro-6,7-dihydro-5H-cyclopenta[b]pyridin-7-ylamino)-2-fluorophenyl)-3,5,5,6-tetramethyl-5,6-dihydropyrimidin-4(3H)-one,
  salt of (R)—N-(3-((S)-2-amino-1,4,5,5-tetramethyl-6-oxo-1,4,5,6-tetrahydropyrimidin-4-yl)-4-fluorophenyl)-3,3,3-trifluoro-2-hydroxy-2-methylpropanamide with trifluoro-acetic acid,
  (S)-2-Amino-6-(2-fluoro-5-(2-methoxy-5-(trifluoromethyl)phenylamino)phenyl)-3,5,5,6-tetramethyl-5,6-dihydropyrimidin-4(3H)-one,
  (S)-2-Amino-6-(2-fluoro-5-(pyridin-2-ylamino)phenyl)-3,5,5,6-tetramethyl-5,6-dihydropyrimidin-4(3H)-one,
  (S)-2-Amino-6-[2-fluoro-5-(1-methyl-1H-pyrazol-3-ylamino)-phenyl]-3,5,5,6-tetramethyl-5,6-dihydro-3H-pyrimidin-4-one,
  (S)-2-Amino-6-[2-fluoro-5-(tetrahydro-furan-3-ylamino)-phenyl]-3,5,5,6-tetramethyl-5,6-dihydro-3H-pyrimidin-4-one,
  (S)-2-Amino-6-[2-fluoro-5-(tetrahydro-pyran-3-ylamino)-phenyl]-3,5,5,6-tetramethyl-5,6-dihydro-3H-pyrimidin-4-one,
  (S)-2-Amino-6-[2-fluoro-5-(tetrahydro-pyran-4-ylamino)-phenyl]-3,5,5,6-tetramethyl-5,6-dihydro-3H-pyrimidin-4-one,
  (S)-2-Amino-6-[5-(1,1-dioxo-2,3-dihydro-1H-1-benzo[b]thiophen-3-ylamino)-2-fluoro-phenyl]-3,5,5,6-tetramethyl-5,6-dihydro-3H-pyrimidin-4-one,
  (S)-2-Amino-6-{2-fluoro-5-[(5-methyl-isoxazol-3-ylmethyl)-amino]-phenyl}-3,5,5,6-tetramethyl-5,6-dihydro-3H-pyrimidin-4-one,
  (S)-2-Amino-6-{2-fluoro-5-[(tetrahydro-furan-3-ylmethyl)-amino]-phenyl}-3,5,5,6-tetramethyl-5,6-dihydro-3H-pyrimidin-4-one,
  (S)-2-Amino-6-{2-fluoro-5-[1-(2H-pyrazol-3-yl)-ethylamino]-phenyl}-3,5,5,6-tetramethyl-5,6-dihydro-3H-pyrimidin-4-one,
  (S)-2-Amino-6-{2-fluoro-5-[1-(5-methyl-2H-pyrazol-3-yl)-ethylamino]-phenyl}-3,5,5,6-tetramethyl-5,6-dihydro-3H-pyrimidin-4-one,
  (S)-2-Amino-6-{5-[(2,2-difluoro-cyclopropylmethyl)amino]-2-fluoro-phenyl}-3,5,5,6-tetramethyl-5,6-dihydro-3H-pyrimidin-4-one,
  (S)-2-Amino-6-{5-[(4-chloro-1-methyl-1H-pyrazol-3-ylmethyl)-amino]-2-fluoro-phenyl}-3,5,5,6-tetramethyl-5,6-dihydro-3H-pyrimidin-4-one,
  (S)-2-Amino-6-{5-[(4-chloro-2H-pyrazol-3-ylmethyl)-amino]-2-fluoro-phenyl}-3,5,5,6-tetramethyl-5,6-dihydro-3H-pyrimidin-4-one, 2-[3-((S)-2-Amino-1,4,5,5-tetramethyl-6-oxo-1,4,5,6-tetrahydro-pyrimidin-4-yl)-4-fluoro-phenylamino]-cyclopentanecarbonitrile, and salt of N-[3-((S)-2-Amino-1,4,5,5-tetramethyl-6-oxo-1,4,5,6-tetrahydro-pyrimidin-4-yl)-4-fluoro-phenyl]-3,3,3-trifluoro-2-hydroxy-propionamide with trifluoro-acetic acid.

* * * * *